US008206942B2

(12) United States Patent
Alessi et al.

(10) Patent No.: US 8,206,942 B2
(45) Date of Patent: *Jun. 26, 2012

(54) METHODS OF IDENTIFYING LRRK2 INHIBITORS

(75) Inventors: Dario Alessi, Dundee (GB); R. Jeremy Nichols, Dundee (GB)

(73) Assignee: Medical Research Council (GB)

( * ) Notice: Subject to any disclaimer, the term of this patent is extended or adjusted under 35 U.S.C. 154(b) by 0 days.

This patent is subject to a terminal disclaimer.

(21) Appl. No.: 12/553,932

(22) Filed: Sep. 3, 2009

(65) Prior Publication Data

US 2010/0068742 A1    Mar. 18, 2010

Related U.S. Application Data

(63) Continuation-in-part of application No. 12/244,715, filed on Oct. 2, 2008, now Pat. No. 7,947,468, and a continuation-in-part of application No. PCT/GB2009/002047, filed on Aug. 24, 2009, each of which is a continuation-in-part of application No. PCT/GB2008/001211, filed on Apr. 7, 2008.

(60) Provisional application No. 60/910,242, filed on Apr. 5, 2007.

(30) Foreign Application Priority Data

Apr. 5, 2007  (GB) ......................... 0706709
Aug. 24, 2009  (EP) ......................... 09252042

(51) Int. Cl.
*C12Q 1/48* (2006.01)
(52) U.S. Cl. ............................................. 435/15
(58) Field of Classification Search ............... 435/15
See application file for complete search history.

(56) References Cited

U.S. PATENT DOCUMENTS

| 2003/0166222 A1 | 9/2003 | Meyers |
| 2004/0265849 A1 | 12/2004 | Cargill et al. |
| 2009/0004112 A1 | 1/2009 | Abeliovich |
| 2009/0142784 A1 | 6/2009 | Alessi et al. |

FOREIGN PATENT DOCUMENTS

| WO | 2004074485 A | 9/2004 |
| WO | 2007104763 A1 | 9/2007 |
| WO | 2008091799 A2 | 7/2008 |
| WO | 2008122789 A2 | 10/2008 |

OTHER PUBLICATIONS

Giasson et al. "Mutations in LRRK2 as a cause of Parkinson's Disease." Neuro-Signals 2008, vol. 16, No. 1, Dec. 5, 2007, pp. 99-105.
Jakse et al. "Comparative Sequence and Genetic Analyses of Asparagus BACs Reveal No Microsynteny with Onion or Rice." Theoretical and Applied Genetics: International Journal of Plant Breeding Research, Springer, Berlin, vol. 114, No. 1, Sep. 22, 2006, pp. 31-39.
Telgmann-Rauber et al. "Genetic and Physical Maps Around the Sex-Determining M-Locus of the Dioecious Plant Asparagus." Molecular Genetics and Genomics, Springer, Berlin, vol. 278, No. 3, Jul. 3, 2007, pp. 221-234.
Marin, The Parkinson Disease Gene LRRK2: Evolutionary and Structural Insights, Mol. Biol. Evol., 2006, 2423-2433, 23(12), Oxford University Press on behalf of the Society for Molecular Biology and Evolution.
Goldberg et al, Identification of four candidate cGMP targets in Dictyostelium, PNAS, 2002, 6749-6754, vol. 99, No. 10, Boston Biomedical Research Institute.
West et al, Parkinson's disease-associated mutations in leucine-rich repeat kinase 2 augment kinase activity, PNAS, 2005, 16842-19847, vol. 102, No. 46, Institute for Cell Engineer ng, Departments of Neurology, Neuroscience, and Physiology.
Bosgraaf et al, A novel cGMP signalling pathway mediating myosin phosphorylation and chemotaxis in Dictyostelium, The EMBO Journal, 2002, 4560-4570, vol. 21, No. 17, Department of Biochemistry, University of Groningen.
Tran Quang et al, Ezrin function is required for ROCK-mediated fibroblast transformation by the Net and Dbl oncogenes, The EMBO Journal, 2000, 4565-4576, vol. 19, No. 17, Imperial Cancer Research Fund Laboratories.
Cohen et al, Kestrel: a powerful method for identifying the physiological substrates of protein kinases, Biochemical Journal, 2006, 1-6, 393, MRC protein Phosphorylation Unit.
Gary et al, Ezrin Self-Association Involves Binding of an N-Terminal Domain to a Normally Masked C-Terminal Domain that Includes the F-Actin Binding Site, Molecular Biology of the Cell, 1995, 1061-1075, vol. 6, The American Society for Cell Biology.
Pestonjamasp et al, Moesin, Ezrin, and p205 Are Actin-binding Proteins Associated with Neutrophil Plasma Membranes, Molecular Biology of the Cell, 1995, 247-259, vol. 6, The American Society for Cell Biology. Nakamura et al, Regulation of F-Actin Binding to Platelet Moesin In Vitro by Both Phosphorylation of Threonine 558 and Polyphosphatidylinositides, Molecular Biology of the Cell, 1999, 2669-2685, vol. 10, The American Society for Cell Biology.
Turunen et al, Ezrin Has a COOH-Terminal Actin-binding Site That Is Conserved in the Ezrin Protein Family, The Journal of Cell Biology, 1994, 1445-1453, vol. 126, No. 6, The Rockefeller University Press.
Matsui et al, Rho-Kinase Phosphorylates COOH-terminal Threonines of Ezrin/Radixin/Moesin (ERM) Proteins and Regulates Their Head-to-Tail Association, The Journal of Cell Biology, 1998, 647-657, vol. 140, No. 3, The Rockefeller University Press.

(Continued)

*Primary Examiner* — Maryam Monshipouri
(74) *Attorney, Agent, or Firm* — K&L Gates LLP; Louis C. Cullman; Michelle Glasky Bergman

(57) ABSTRACT

A method for identifying a compound expected to be useful in modulating, for example inhibiting, LRRK2 protein kinase activity, the method comprising the steps of (1) determining whether a test compound modulates, for example inhibits, the protein kinase activity of a LRRK2 polypeptide on a substrate polypeptide and (2) selecting a compound which modulates, for example inhibits, the said LRRK2 polypeptide protein kinase activity, wherein the substrate polypeptide comprises the sequence (W/F/R/K)(W/F/R/K)(R/K)(F/W/H/R)(Y/W/R)(S/T)(L/V/I) (R/K)(R/K)(A/Y) or (W/R)(X)(X)(F/Y/H/T)(Y/W/R)(T)(X)(R/T)(R)(X), where X represents any amino acid. Such a compound may be useful in treating Parkinson's Disease or Parkinsonism. The substrate polypeptide may consist or comprise the sequence RLGWWRFY TLRRARQGNTKQ.

9 Claims, 26 Drawing Sheets

OTHER PUBLICATIONS

Paglini et al, Suppression of Radixin and Moesin Alters Growth Cone Morphology, Motility, and process Formation in Primary Cultured Neurons, The Journal of Cell Biology, 1998, 443-455, vol. 143, No. 2, The Rockefeller University Press.

Huang et al, Replacement of Threonine 558, a Critical Site of Phosphorylation of Moesin in Vivo, with Aspartate Activates F-actin Binding of Moesin, The Journal of Biological Chemistry, 1999, 12803-12810, vol. 274, No. 18, The American Society for Biochemistry and Molecular Biology, Inc.

Oshiro et al, Phosphorylation of Moesin by Rho-associated Kinase (Rho-kinase) Plays a Crucial Role in the Formation of Microvilli-like Structures, The Journal of Biological Chemistry, 1998, 34663-34666, vol. 273, No. 52, The American Society for Biochemistry and Molecular Biology, Inc.

McClatchey et al, Membraine organization and tumorigenesis—the NF2 tumor suppressor, Merlin, Genes & Development, 2005, 2265-2277,19, Massachusetts General Hospital, Center for Cancer Research and Harvard Medical School, Department of Pathology, Charlestown.

West et al, Parkinson's disease-associated mutations in LRRK2 link enhanced GTP-binding and kinase activities to neuronal toxicity, Human Molecular Genetics, 2007, 223-232, vol. 16, No. 2, Oxford University Press.

Gloeckner et al, The Parkinson disease causing LRRK2 mutation I2020T is associated with increased kinase activity, Human Molecular Genetics, 2006, 223-232, vol. 15, No. 2 Oxford University Press.

Jaleel et al, LRRK2 phosphorylates moesin at threonine-558: characterization of how Parkinson's disease mutants affect kinase activity, Biochemical Journal, 2007, 307-317, 405, Biochemical Society.

Polesello et al, Small is beautiful: what flies tell us about ERM protein function in development, Trends in Cell Biology, 2004, vol. 14, No. 6, pp. 294-302, Centre de Biologie du Developpement, France.

Taylor et al, LRRK2: a common pathway for parkinsonism, pathogenesis and prevention?, Trends in Molecular Medicine, 2006, vol. 12, No. 2, pp. 76-82, Department of Neuroscience, Mayo Clinic College of Medicine, Jacksonville.

Mata et al, LRRK2 in Parkinson's disease: protein domains and functional insights, Trends in Neuroscience, 2006, vol. 29, No. 5, pp. 286-293, Department of Neuroscience, Mayo Clinic College of Medicine, Jacksonville.

Farrer et al, LRRK2 mutations in Parkinson disease, Neurology, 2005, 738-740, 65, AAN Enterprises, Inc.

Biskup et al, Localization of LRRK2 to Membranous and Vesicular Structures in Mammalian Brain, American Neurological Association, 2006, 557-569, 60.

Pearson et al, Structure of the ERM Protein Moesin Reveals the FERM Domain Fold Masked by an Extended Actin Binding Tail Domain, Cell, 2000, 259-270, vol. 101, Cell Press.

Bretscher et al, ERM Proteins and Merlin: Integrators at the Cell Cortex, Mol. Cell. Bio., 2002, 586-599, vol. 3, Nature Publishing Group.

Bosgraaf et al, Roc, a Ras/GTPase domain in complex proteins, Science Direct, 2003, 5-10, Elsevier.

MacLeod et al, The Familial Parkinsonism Gene LRRK2 Regu ates Neurite Process Morphology, Neuron, 2006, 587-593, 52, Elsevier Inc.

Troiani et al, Searching for Biomarkers of Aurora-A Kinase Activity: Identification of in Vitro Substrates through a Modified KESTREL Approach, Journal of Proteome Research, 2005, 1296-1303, 4, American Chemical Society.

Campbell et al, Identification of Protein Phosphorylation Sites by a Combination of Mass Spectrometry and Solid Phase Edman Sequencing, Journal of Biomolecular Techniques, 2002, 121-132, vol. 13, Issue 3, MRC Protein Phosphorylation Unit, University of Dundee, Scotland.

Durocher et al, High-level and high-throughput recombinanl protein production by transient transfection of suspension-growing human 293-EBNA1 cells, Nucleic Acids Research, 2002, e9, vol. 30, No. 2, Oxford University Press.

Manning et al, The Protein Kinase Complement of the Human Genome, Science, 2002, 1912-1934, vol. 298.

Zabetian et al, A clinic-based study of the LRRK2 gene in Parkinson disease yields new mutations, Neurology, 2005, 741-744, 65, AAN Enterprises, Inc.

Farrer et al, LRRK2 mutations in Parkinson disease, Neurology, 738-740, 65, AAN Enterprises, Inc.

Zimprich et al, Mutations in LRRK2 Cause Autosomal-Dominant Prkinsonism with Pleomorphic Pathology, Neuron, 2004, 601-607, vol. 44, Cell Press.

Paisan-Ruiz et al, Cloning of the Gene Containing Mutations that Cause PARK8-Linked Parkinson's Disease, Neuron, 2004, 595-600, vol. 44, Cell Press.

Boudeau et al, Emerging roles of pseudokinases, Trends in Cell Biology, vol. 16, No. 9, 443-452 MRC Protein Phosphorylation Unit, School of Life Sciences, University of Dundee, United Kingdom.

Katayama S et al. "Antisense transcription in the mammalian transcriptome" Science 309:1564-1566, 2005.

Greggio E et al. "Leucine rich repeat kinase 2 mutations and Parkinson's Disease: three questions." ASN Neuro. Apr. 14, 2009:1(1). pii: e00002. doi: 10.1042/AN20090007.

Healy DG et al. "Phenotype, genotype, and worldwide genetic penetrance of LRRK2-associated Parkinson's disease: a case-control study." Lancet Neurol 7:583-590, 2008.

Biskup, S. and West, A. B. "Zeroing in on LRRK2-linked pathogenic mechanisms in Parkinson's disease." Biochim Biophys Acta 1792:625-633, 2008.

Covy, J. P. and Giasson, B. I. "Identification of compounds that inhibit the kinase activity of leucine-rich repeat kinase 2." Biochem Biophys Res Commun 378:473-477, 2009.

Anand, V. S. et al. "Investigation of leucine-rich repeat kinase 2 enzymological properties and novel assays." FEBS J 276:466-478, 2009.

Miller, M. L. et al. "Linear motif atlas for phosphorylation-dependent signaling." Sci Signal 1:ra2, 2008.

Belkina, N. V. et al. "LOK is a major ERM kinase in resting lymphocytes and regulates cytoskeletal rearrangement through ERM phosphorylation." Proc Natl Acad Sci U S A 106:4707-4712, 2009.

ten Klooster, J. P. et al. "Mst4 and Ezrin induce brush borders downstream of the Lkb1/Strad/Mo25 polarization complex." Dev Cell 16:551-562, 2009.

Reichling, L. J. and Riddle, S. M. "Leucine-rich repeat kinase 2 mutants I2020T and G2019S exhibit altered kinase inhibitor sensitivity." Biochem Biophys Res Commun 384:255-258, 2009.

```
        W
    W   F   R   F   Y              L   R
  F   R   K   W H R   W R        V I K   R
R K                                    K A Y
-5 - 4 - 3 - 2 - 1 - P - +1 +2 +3 +4
W - W - R - F - Y - [S/T] - L - R - R - A/Y
```

Nictide      RLGWRFYTLRRARQGNTKQR
LongLRRKtide RLGRDKYKTLRQIRQGNTKQR
LRRKtide     RLGRDKYKTLRQIRQ

Figure 9

| | | |
|---|---|---|
| Moesin | 1 | ------------MPKTISVRVTTMDAELEFAIQPNTTGKQLFDQVVKTIGLREVW |
| Ezrin | 1 | ------------MPKPINVRVTTMDAELEFAIQPNTTGKQLFDQVVKTIGLREVW |
| Radixin | 1 | ------------MPKPINVRVTTMDAELEFAIQPNTTGKQLFDQVVKTIGLREVW |
| Merlin | 1 | MAGAIASRMSFSSLKRKQPKTFTVR VTMDAE EFNCEMKWKGKDLFDIVC H GLRETW |
| Moesin | 44 | FFGLQYQD KGFSTWLKINKKVTAQDVRKE SPLIFKFRAKFYPEDVSEELIQ ITQRLFF |
| Ezrin | 44 | FGLHYVDNKGFPTWLKLDKKVSAQ VRKENPLQFKFRAKFYPEDVAEELIQ ITQ LFF |
| Radixin | 44 | FFGLQYVD KG STWLKLNKKVTQQDV KENPLQFKFRAKF PEDVSEELIQ ITQRLFF |
| Merlin | 61 | FFGLQYT-IKDTVAWLK DKKVLDHDVSKEEP TFHFLAKFYPENAEEEL QITQHLFF |
| Moesin | 104 | LQVKEGILND IYCPPETAVLLASYAVQSKYGD NKEVHKSGYLAG LLPQRVLEQHKL |
| Ezrin | 104 | LQVKEGIILSDEIYCPPETAVLL SYAVQAK GDYNKEVHKSGYISS RI PQRV QHKL |
| Radixin | 104 | LQVKE ILNDEIYCPPETAVLLASYAVQAKYGDYNKE HKPGYLA RLLPQRVLEQHKI |
| Merlin | 120 | LQVKKQIID KIYCPPEASVLLASYAVQAKYGDPS VHKR LA ELLPKRV NLYQ |
| Moesin | 164 | NK QWEERIQVWHE EHRGMLR DA E YLKIAQDLEMYGVNYFSIKNKKG ELWLGVDAL |
| Ezrin | 164 | T D QWE RIQVWHA EHRGMI NAM EYLKIAQDLEMYG NYFEIKNKKGT LWLGVDAI |
| Radixin | 164 | TK QWEERIQNWHE EHRGMLR DSM YLKIAQDLEMYGVNYFEIKNKKGTELWLGVDAL |
| Merlin | 180 | TP WEERITA WYAEHRGRAR LAE EYLKIAQDLEMYGVNYFAI NKKGTEL LGVDAL |
| Moesin | 224 | GLNIYEQND LTPKIGFPWSEIRNISFNDKKFVIKPIDKKAPDFVFYAPRLRINKRIIAL |
| Ezrin | 224 | GLNIYE DD LTPKIGFPWSEIRNISFNDKKFVIKPIDKKAPDFVFYAPRLRINKRI QL |
| Radixin | 224 | GLNIYE DD LTPKIGFPWSEIRNIS FNDKKFVIKPIDKKAPDFVFYAPRLRINKRI AL |
| Merlin | 240 | GL HIY P N LTPKISFPWNEIRNIS SDKEFTIKP DKKIDV FNSS LR NKLI QL |
| Moesin | 284 | CMGNHELYMRRRKPDTIEVQQMKAQAREEKHQKQ ERAMLENEKKKRE AE IERE |
| Ezrin | 284 | CMGNHELYMRRRKPDTIEVQQMKAQAREEKHQKQ ERQQLETEKK RETVE EKEQ MRE |
| Radixin | 284 | CMGNHELYMRRRKPDTIEVQQMKAQAREEKHQKQ ERAQLENEKEKRE AE EKE IERE |
| Merlin | 300 | C GNH I MRRRKAD EVQQMKAQAREEKARKQ ERQRIAREKQMREEAE T E ER- |

*Figure 9 (cont.)*

```
Moesin  344  KEEIMERIKQIEEQTKKAQ QELEEQTRRALELE QERKRAQ SEAE IAKERQEA EEAKEA
Ezrin   344  KEEIMLRIQDYEEKTKKAE EISEQIQRAIQ EERKRAQ EEAERIEA RMAAIRAKEE
Radixin 344  KEEIMERIKQIEEQTIKAQ ELEEQTR AIEI QERKRAKEEAERIEKERRAA EEAKSA
Merlin  359  ------RTLQ KEEATMA EAIMRSEETADLI AEKAQITEEEAKLI AQKAAEA EQEMQR Moesin  404  LQASRDQK  QEQLALE AELTA ISQLEMARQ KESEAVEWQQ KAQMV QEDLEKT AEL
Ezrin   404  EQA DQ  K QEQLAAELAE TAKIALLEEAR  KE EV EWQH AKEAQ DLVKTKEEL
Radixin 404  A QA ADQ KNQEQLAAELAE TAKIALLEEA KE EATEWQHKAFAAQ EDLEKTKEEL
Merlin  413  KATA RTEEEKRL EQK LEAEVLALK AEESE AKEA QLKQDLQEAREAER AKQKL Moesin  464  KTAM TP------HVAEPAENEQDEQDENGAEAS---- A TRA AKDRSEEERTEAEK
Ezrin   464  HLVM APPPPPPPVYEPV YHVQ SLQ EGAEP G SAEISSEG RDDRNEEKR TEAEK
Radixin 464  KTVM APPPPPPPVIPP ENEHDEHDENNAEAS---- AEISNEG NHRSEEERVTETQK
Merlin  473  LE A KPTYPPMNP PAPLPP IPSFNLIGDSLS-DFKD DMKR SMEIEKE VEYMEK Moesin  515  NERVQKHIKAI SELA ARDE KKTAND HAEN--MRLGRDKYKTLRQIRQGNTKQRIDE
Ezrin   524  NERVQ QIVTLSSEISQARDENK THNDI HNEN--MRQGRDKYKTLRQIRQGNTKQRIDE
Radixin 521  NERVKQL ALSSELAQARDE KKTQND HAEN--GRDKYKTLRQIRQGNTKQRIDE
Merlin  532  SKH QEQL EIK E EAL LKE ETAIDI HNENSDR GSSKHNT K TLQSAKSR AF Moesin  574  FES
Ezrin   583  FEA
Radixin 580  FEA
Merlin  592  FEE
```

Figure 11

GPLGSMGPQDVGNDWEVLGVHQLILKMLTVHNASVNLSVIGLK
TLDLLLTSGKITLLILDEESDIFMLIFDAMHSFPANDEVQKLG
CKALHVLFERVSEEQLTEFVENKDYMILLSALTNFKDEEEIVL
HVLHCLHSLAIPCNNVEVLMSGNVRCYNIVVEAMKAFPMSERI
QEVSCCLLHRLTLGNFFNILVLNEVHEFVVKAVQQYPENAALQ
ISALSCLALLTETIFLNQDLEEKNENQENDDEGEEDKLFWLEA
CYKALTWHRKNKHVQEAACWALNNLLMYQNSLHEKIGDEDGHF
PAHREVMLSMLMHSSSKEVFQASANALSTLLEQNVNFRKILLS
KGIHLNVLELMQKHIHSPEVAESGCKMLNHLFEGSNTSLDIMA
AVVPKILTVMKRHETSL    SEQ ID NO:66

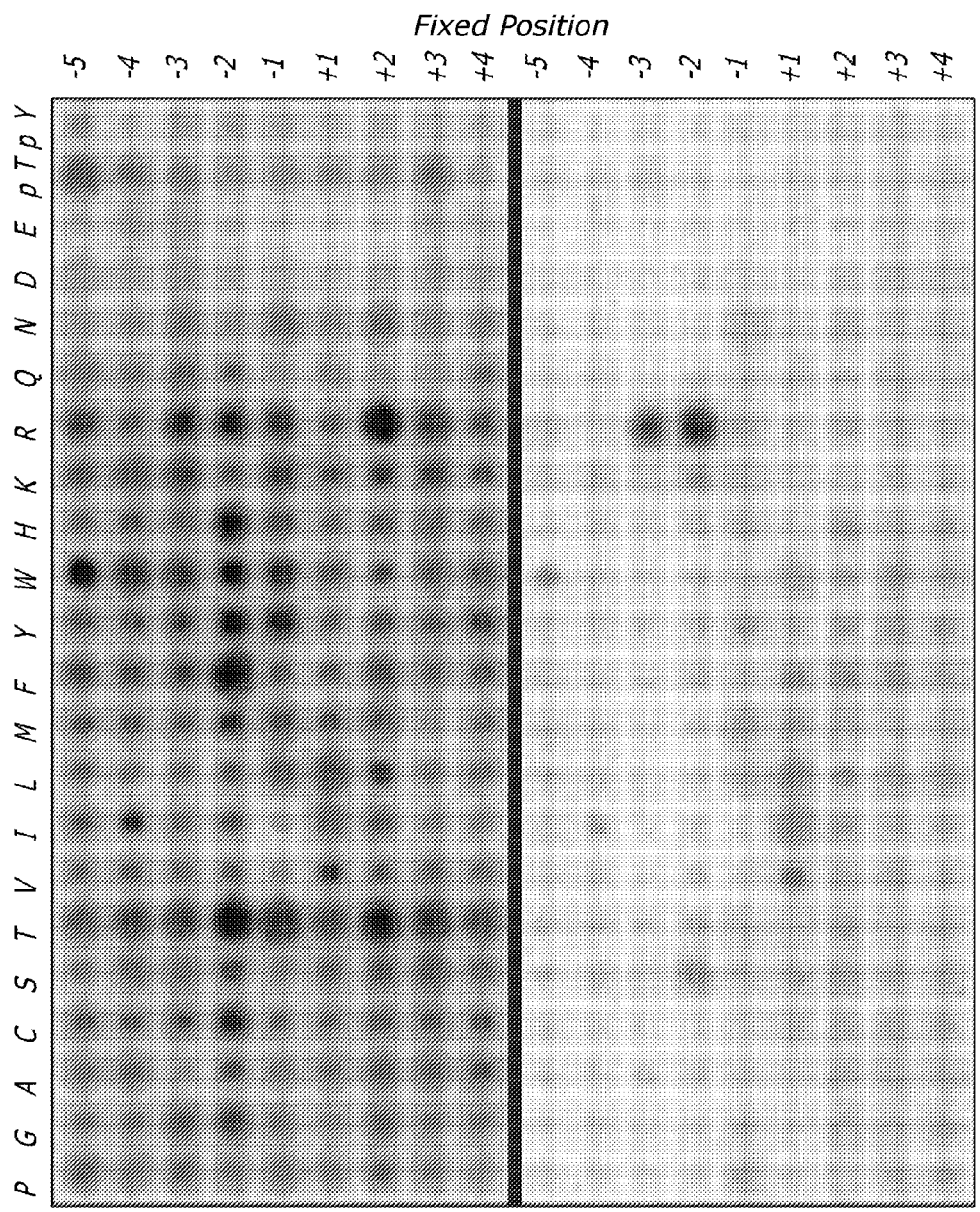

| Position | Peptide sequence | LRRK2 [G2D1953] (1326-2527) Km μM | max U/mg | LRRK2 [Wild type] (1326-2527) Km μM | Vmax U/mg |
|---|---|---|---|---|---|
| Nktide | RLGWWRFYTLRRARQGNTKQR | 10 | 26 | 9 | 16 |
| -6 | RLGAWRFYTLRRARQGNTKQR | 31 | 56 | 30 | 31 |
| -4 | RLGWARFYTLRRARQGNTKQR | 20 | 40 | 33 | 32 |
| -3 | RLGWWAFYTLRRARQGNTKQR | 10 | 11 | 9 | 5 |
| -2 | RLGWWRAYTLRRARQGNTKQR | 15 | 25 | 19 | 23 |
| -1 | RLGWWRFATLRRARQGNTKQR | 24 | 44 | 17 | 16 |
| P | RLGWWRFYALRRARQGNTKQR | NP | NP | NP | NP |
| +1 | RLGWWRFYTARRARQGNTKQR | 17 | 23 | 13 | 8 |
| +2 | RLGWWRFYTLAARQGNTKQR | 21 | 12 | 18 | 3 |
| +3 | RLGWWRFYTLAAARQGNTKQR | 18 | 18 | 10 | 5 |
| +6 | RLGWWRFYTPRAAQGNTKQR | 17 | 22 | 14 | 10 |
| +1 | RLGWWRFYTPRRARQGNTKQR | 8 | 16 | 14 | 8 |
| -5, -4 | RLGAARFATLRRARQGNTKQR | -100 | 75 | -130 | 70 |
| -5, -1 | RLGAARFYTARRARQGNTKQR | 60 | 60 | -100 | 36 |
| -5, -4, +1 | RLGAARFYTLAAARQGNTKQR | -230 | 65 | 18 | 20 |
| -2 | RLGWWRTYTLRRARQGNTKQR | 18 | 18 | 23 | 10 |
| +2 | RLGWWRFYTLTRARQGNTKQR | 25 | 16 | 31 | 9 |
| -2T, +2T | RLGWWRTYTLTRARQGNTKQR | -130 | 15 | -130 | 6 |
| T 5 | RLGWWRFYSLRRARQGNTKQR | NP | NP | NP | NP |

FIG. 14A

SEQUENCE LISTING

<160> NUMBER OF SEQ ID NOS: 74

<210> SEQ ID NO 1
<211> LENGTH: 15
<212> TYPE: PRT
<213> ORGANISM: Homo sapiens

<400> SEQUENCE: 1

Arg Leu Gly Arg Asp Lys Tyr Lys Thr Leu Arg Gln Ile Arg Gln
1               5                   10                  15

<210> SEQ ID NO 2
<211> LENGTH: 21
<212> TYPE: PRT
<213> ORGANISM: Homo sapiens

<400> SEQUENCE: 2

Arg Leu Gly Arg Asp Lys Tyr Lys Thr Leu Arg Gln Ile Arg Gln Gly
1               5                   10                  15

Asn Thr Lys Gln Arg
            20

<210> SEQ ID NO 3
<211> LENGTH: 15
<212> TYPE: PRT
<213> ORGANISM: Homo sapiens
<220> FEATURE:
<221> NAME/KEY: Variation
<222> LOCATION: (9)..(9)
<223> OTHER INFORMATION: Ser or Thr

<400> SEQUENCE: 3

Arg Leu Gly Arg Asp Lys Tyr Lys Xaa Leu Arg Gln Ile Arg Gln
1               5                   10                  15

<210> SEQ ID NO 4
<211> LENGTH: 21
<212> TYPE: PRT
<213> ORGANISM: Homo sapiens
<220> FEATURE:
<221> NAME/KEY: Variation
<222> LOCATION: (9)..(9)
<223> OTHER INFORMATION: Ser or Thr

<400> SEQUENCE: 4

Arg Leu Gly Arg Asp Lys Tyr Lys Xaa Leu Arg Gln Ile Arg Gln Gly
1               5                   10                  15

Asn Thr Lys Gln Arg
            20

<210> SEQ ID NO 5
<211> LENGTH: 13
<212> TYPE: PRT
<213> ORGANISM: Homo sapiens

<400> SEQUENCE: 5

Ile Gly Leu Gln Met Gly Thr Asn Lys Phe Ala Ser Gln
1               5                   10

<210> SEQ ID NO 6
<211> LENGTH: 13
<212> TYPE: PRT
<213> ORGANISM: Homo sapiens

<400> SEQUENCE: 6

```
Gln Met Thr Ala Tyr Gly Thr Arg Arg His Leu Tyr Asp
1               5                   10

<210> SEQ ID NO 7
<211> LENGTH: 13
<212> TYPE: PRT
<213> ORGANISM: Homo sapiens

<400> SEQUENCE: 7

Asp Arg Lys Lys Arg Tyr Thr Val Val Gln Asn Pro Tyr
1               5                   10

<210> SEQ ID NO 8
<211> LENGTH: 13
<212> TYPE: PRT
<213> ORGANISM: Homo sapiens

<400> SEQUENCE: 8

Lys Gln Gln Arg Glu Lys Thr Arg Trp Leu Asn Ser Gly
1               5                   10

<210> SEQ ID NO 9
<211> LENGTH: 13
<212> TYPE: PRT
<213> ORGANISM: Homo sapiens

<400> SEQUENCE: 9

Ser Ala Val Arg Leu Arg Ser Ser Val Pro Gly Val Pro
1               5                   10

<210> SEQ ID NO 10
<211> LENGTH: 13
<212> TYPE: PRT
<213> ORGANISM: Homo sapiens

<400> SEQUENCE: 10

Ser Val Arg Arg Ser Tyr Ser Ser Ser Gly Ser Leu
1               5                   10

<210> SEQ ID NO 11
<211> LENGTH: 13
<212> TYPE: PRT
<213> ORGANISM: Homo sapiens

<400> SEQUENCE: 11

Met Glu Arg Arg Arg Ile Thr Ser Ala Ala Arg Arg Ser
1               5                   10

<210> SEQ ID NO 12
<211> LENGTH: 13
<212> TYPE: PRT
<213> ORGANISM: Homo sapiens

<400> SEQUENCE: 12

Thr Ser Ala Ala Arg Arg Ser Tyr Val Ser Ser Gly Glu
1               5                   10

<210> SEQ ID NO 13
<211> LENGTH: 13
<212> TYPE: PRT
<213> ORGANISM: Homo sapiens

<400> SEQUENCE: 13

Gly Pro Gly Thr Arg Leu Ser Leu Ala Arg Met Pro Pro
1               5                   10
```

```
<210> SEQ ID NO 14
<211> LENGTH: 13
<212> TYPE: PRT
<213> ORGANISM: Homo sapiens

<400> SEQUENCE: 14

Asn Ile Pro Arg Arg Thr Thr Gln Arg Ile Val Ala Pro
1               5                   10

<210> SEQ ID NO 15
<211> LENGTH: 13
<212> TYPE: PRT
<213> ORGANISM: Homo sapiens

<400> SEQUENCE: 15

Ala Lys Ser Arg Leu Gln Thr Ala Pro Val Pro Met Pro
1               5                   10

<210> SEQ ID NO 16
<211> LENGTH: 13
<212> TYPE: PRT
<213> ORGANISM: Homo sapiens

<400> SEQUENCE: 16

Ile Glu Thr His Lys Leu Thr Phe Arg Glu Asn Ala Arg
1               5                   10

<210> SEQ ID NO 17
<211> LENGTH: 13
<212> TYPE: PRT
<213> ORGANISM: Homo sapiens

<400> SEQUENCE: 17

Thr Ser Pro Arg His Leu Ser Asn Val Ser Ser Ser Gly
1               5                   10

<210> SEQ ID NO 18
<211> LENGTH: 13
<212> TYPE: PRT
<213> ORGANISM: Homo sapiens

<400> SEQUENCE: 18

Ala Ser Pro Arg Arg Leu Ser Asn Val Ser Ser Ser Gly
1               5                   10

<210> SEQ ID NO 19
<211> LENGTH: 13
<212> TYPE: PRT
<213> ORGANISM: Homo sapiens

<400> SEQUENCE: 19

Gly Arg Asp Lys Tyr Lys Thr Leu Arg Gln Ile Arg Gln
1               5                   10

<210> SEQ ID NO 20
<211> LENGTH: 13
<212> TYPE: PRT
<213> ORGANISM: Homo sapiens

<400> SEQUENCE: 20

Pro Arg Glu Lys Arg Arg Ser Thr Gly Val Ser Phe Trp
1               5                   10

<210> SEQ ID NO 21
```

```
<211> LENGTH: 13
<212> TYPE: PRT
<213> ORGANISM: Homo sapiens

<400> SEQUENCE: 21

Arg Pro Gln Arg Ala Thr Ser Asn Val Phe Ala Met Phe
1               5                   10

<210> SEQ ID NO 22
<211> LENGTH: 13
<212> TYPE: PRT
<213> ORGANISM: Homo sapiens

<400> SEQUENCE: 22

Lys Lys Lys Lys Arg Phe Ser Phe Lys Lys Ser Phe Lys
1               5                   10

<210> SEQ ID NO 23
<211> LENGTH: 13
<212> TYPE: PRT
<213> ORGANISM: Homo sapiens

<400> SEQUENCE: 23

Gly Ser Ser Lys His Asn Thr Ile Lys Lys Leu Tyr Leu
1               5                   10

<210> SEQ ID NO 24
<211> LENGTH: 5
<212> TYPE: PRT
<213> ORGANISM: Homo sapiens
<220> FEATURE:
<221> NAME/KEY: Phosphorylation
<222> LOCATION: (3)..(3)
<223> OTHER INFORMATION: Phospho threonine

<400> SEQUENCE: 24

Tyr Lys Thr Leu Arg
1               5

<210> SEQ ID NO 25
<211> LENGTH: 7
<212> TYPE: PRT
<213> ORGANISM: Homo sapiens
<220> FEATURE:
<221> NAME/KEY: Phosphorylation
<222> LOCATION: (5)..(5)
<223> OTHER INFORMATION: Phospho threonine

<400> SEQUENCE: 25

Asp Lys Tyr Lys Thr Leu Arg
1               5

<210> SEQ ID NO 26
<211> LENGTH: 10
<212> TYPE: PRT
<213> ORGANISM: Homo sapiens
<220> FEATURE:
<221> NAME/KEY: Phosphorylation
<222> LOCATION: (3)..(3)
<223> OTHER INFORMATION: Phospho threonine

<400> SEQUENCE: 26

Ala Leu Thr Ser Glu Leu Ala Asn Ala Arg
1               5                   10

<210> SEQ ID NO 27
<211> LENGTH: 5
<212> TYPE: PRT
```

```
<213> ORGANISM: Homo sapiens
<220> FEATURE:
<221> NAME/KEY: Phosphorylation
<222> LOCATION: (3)..(3)
<223> OTHER INFORMATION: Phospho serine

<400> SEQUENCE: 27

Arg Pro Ser Gln Arg
1               5

<210> SEQ ID NO 28
<211> LENGTH: 8
<212> TYPE: PRT
<213> ORGANISM: Homo sapiens
<220> FEATURE:
<221> NAME/KEY: Phosphorylation
<222> LOCATION: (1)..(1)
<223> OTHER INFORMATION: Phospho threonine

<400> SEQUENCE: 28

Thr Pro Pro Pro Ser Gln Gly Lys
1               5

<210> SEQ ID NO 29
<211> LENGTH: 10
<212> TYPE: PRT
<213> ORGANISM: Homo sapiens
<220> FEATURE:
<221> NAME/KEY: Phosphorylation
<222> LOCATION: (7)..(7)
<223> OTHER INFORMATION: Phospho threonine

<400> SEQUENCE: 29

Gly His Asp Ala Gln Gly Thr Leu Ser Lys
1               5                   10

<210> SEQ ID NO 30
<211> LENGTH: 12
<212> TYPE: PRT
<213> ORGANISM: Homo sapiens
<220> FEATURE:
<221> NAME/KEY: Phosphorylation
<222> LOCATION: (7)..(7)
<223> OTHER INFORMATION: Phospho threonine

<400> SEQUENCE: 30

Tyr Leu Ala Ser Ala Ser Thr Met Asp His Ala Arg
1               5                   10

<210> SEQ ID NO 31
<211> LENGTH: 6
<212> TYPE: PRT
<213> ORGANISM: Homo sapiens
<220> FEATURE:
<221> NAME/KEY: Phosphorylation
<222> LOCATION: (4)..(4)
<223> OTHER INFORMATION: Phospho threonine

<400> SEQUENCE: 31

Asn Ile Val Thr Pro Arg
1               5

<210> SEQ ID NO 32
<211> LENGTH: 10
<212> TYPE: PRT
<213> ORGANISM: Homo sapiens
<220> FEATURE:
<221> NAME/KEY: PHOSPHORYLATION
<222> LOCATION: (1)..(1)
<223> OTHER INFORMATION: Phospho threonine
```

<400> SEQUENCE: 32

Thr Thr His Tyr Gly Ser Leu Pro Gln Lys
1               5                   10

<210> SEQ ID NO 33
<211> LENGTH: 11
<212> TYPE: PRT
<213> ORGANISM: Homo sapiens

<400> SEQUENCE: 33

Leu Met Ile Val Gly Asn Thr Gly Ser Gly Lys
1               5                   10

<210> SEQ ID NO 34
<211> LENGTH: 11
<212> TYPE: PRT
<213> ORGANISM: Homo sapiens

<400> SEQUENCE: 34

Thr Thr Leu Leu Gln Gln Leu Met Lys Thr Lys
1               5                   10

<210> SEQ ID NO 35
<211> LENGTH: 13
<212> TYPE: PRT
<213> ORGANISM: Homo sapiens
<220> FEATURE:
<221> NAME/KEY: Phosphorylation
<222> LOCATION: (4)..(4)
<223> OTHER INFORMATION: Phospho threonine

<400> SEQUENCE: 35

Leu Arg Lys Thr Ile Ile Asn Glu Ser Leu Asn Phe Lys
1               5                   10

<210> SEQ ID NO 36
<211> LENGTH: 16
<212> TYPE: PRT
<213> ORGANISM: Homo sapiens
<220> FEATURE:
<221> NAME/KEY: Phosphorylation
<222> LOCATION: (2)..(2)
<223> OTHER INFORMATION: Phospho serine

<400> SEQUENCE: 36

Gly Ser Leu Glu Val Leu Phe Gln Gly Pro Leu Gly Ser Leu Lys Lys
1               5                   10                  15

<210> SEQ ID NO 37
<211> LENGTH: 14
<212> TYPE: PRT
<213> ORGANISM: Homo sapiens
<220> FEATURE:
<221> NAME/KEY: Phosphorylation
<222> LOCATION: (12)..(12)
<223> OTHER INFORMATION: Phospho threonine

<400> SEQUENCE: 37

Glu Glu Phe Tyr Ser Thr His Pro His Phe Met Thr Gln Arg
1               5                   10

<210> SEQ ID NO 38
<211> LENGTH: 19
<212> TYPE: PRT
<213> ORGANISM: Homo sapiens

<400> SEQUENCE: 38

```
Ala Ser Ser Ser Pro Val Ile Leu Val Gly Thr His Leu Asp Val Ser
1               5                   10                  15

Asp Glu Lys
```

<210> SEQ ID NO 39
<211> LENGTH: 577
<212> TYPE: PRT
<213> ORGANISM: Homo sapiens

<400> SEQUENCE: 39

```
Met Pro Lys Thr Ile Ser Val Arg Val Thr Thr Met Asp Ala Glu Leu
1               5                   10                  15

Glu Phe Ala Ile Gln Pro Asn Thr Thr Gly Lys Gln Leu Phe Asp Gln
                20                  25                  30

Val Val Lys Thr Ile Gly Leu Arg Glu Val Trp Phe Phe Gly Leu Gln
            35                  40                  45

Tyr Gln Asp Thr Lys Gly Phe Ser Thr Trp Leu Lys Leu Asn Lys Lys
    50                  55                  60

Val Thr Ala Gln Asp Val Arg Lys Glu Ser Pro Leu Leu Phe Lys Phe
65                  70                  75                  80

Arg Ala Lys Phe Tyr Pro Glu Asp Val Ser Glu Leu Ile Gln Asp
                85                  90                  95

Ile Thr Gln Arg Leu Phe Phe Leu Gln Val Lys Glu Gly Ile Leu Asn
                100                 105                 110

Asp Asp Ile Tyr Cys Pro Pro Glu Thr Ala Val Leu Leu Ala Ser Tyr
            115                 120                 125

Ala Val Gln Ser Lys Tyr Gly Asp Phe Asn Lys Glu Val His Lys Ser
    130                 135                 140

Gly Tyr Leu Ala Gly Asp Lys Leu Leu Pro Gln Arg Val Leu Glu Gln
145                 150                 155                 160

His Lys Leu Asn Lys Asp Gln Trp Glu Glu Arg Ile Gln Val Trp His
                165                 170                 175

Glu Glu His Arg Gly Met Leu Arg Glu Asp Ala Val Leu Glu Tyr Leu
                180                 185                 190

Lys Ile Ala Gln Asp Leu Glu Met Tyr Gly Val Asn Tyr Phe Ser Ile
            195                 200                 205

Lys Asn Lys Lys Gly Ser Glu Leu Trp Leu Gly Val Asp Ala Leu Gly
    210                 215                 220

Leu Asn Ile Tyr Glu Gln Asn Asp Arg Leu Thr Pro Lys Ile Gly Phe
225                 230                 235                 240

Pro Trp Ser Glu Ile Arg Asn Ile Ser Phe Asn Asp Lys Lys Phe Val
                245                 250                 255

Ile Lys Pro Ile Asp Lys Lys Ala Pro Asp Phe Val Phe Tyr Ala Pro
                260                 265                 270

Arg Leu Arg Ile Asn Lys Arg Ile Leu Ala Leu Cys Met Gly Asn His
            275                 280                 285

Glu Leu Tyr Met Arg Arg Arg Lys Pro Asp Thr Ile Glu Val Gln Gln
    290                 295                 300

Met Lys Ala Gln Ala Arg Glu Glu Lys His Gln Lys Gln Met Glu Arg
305                 310                 315                 320

Ala Met Leu Glu Asn Glu Lys Lys Arg Glu Met Ala Glu Lys Glu
                325                 330                 335

Lys Glu Lys Ile Glu Arg Glu Lys Glu Glu Leu Met Glu Arg Leu Lys
                340                 345                 350
```

```
Gln Ile Glu Glu Gln Thr Lys Lys Ala Gln Gln Leu Glu Glu Gln
        355                 360                 365

Thr Arg Arg Ala Leu Glu Leu Glu Gln Glu Arg Lys Arg Ala Gln Ser
370                 375                 380

Glu Ala Glu Lys Leu Ala Lys Glu Arg Gln Ala Glu Glu Ala Lys
385                 390                 395                 400

Glu Ala Leu Leu Gln Ala Ser Arg Asp Gln Lys Lys Thr Gln Glu Gln
                405                 410                 415

Leu Ala Leu Glu Met Ala Glu Leu Thr Ala Arg Ile Ser Gln Leu Glu
                420                 425                 430

Met Ala Arg Gln Lys Lys Glu Ser Glu Ala Val Glu Trp Gln Gln Lys
                435                 440                 445

Ala Gln Met Val Gln Glu Asp Leu Glu Lys Thr Arg Ala Glu Leu Lys
450                 455                 460

Thr Ala Met Ser Thr Pro His Val Ala Glu Pro Ala Glu Asn Glu Gln
465                 470                 475                 480

Asp Glu Gln Asp Glu Asn Gly Ala Glu Ala Ser Ala Asp Leu Arg Ala
                485                 490                 495

Asp Ala Met Ala Lys Asp Arg Ser Glu Glu Arg Thr Thr Glu Ala
                500                 505                 510

Glu Lys Asn Glu Arg Val Gln Lys His Leu Lys Ala Leu Thr Ser Glu
515                 520                 525

Leu Ala Asn Ala Arg Asp Glu Ser Lys Lys Thr Ala Asn Asp Met Ile
530                 535                 540

His Ala Glu Asn Met Arg Leu Gly Arg Asp Lys Tyr Lys Thr Leu Arg
545                 550                 555                 560

Gln Ile Arg Gln Gly Asn Thr Lys Gln Arg Ile Asp Glu Phe Glu Ser
                565                 570                 575

Met

<210> SEQ ID NO 40
<211> LENGTH: 586
<212> TYPE: PRT
<213> ORGANISM: Homo sapiens

<400> SEQUENCE: 40

Met Pro Lys Pro Ile Asn Val Arg Val Thr Thr Met Asp Ala Glu Leu
1               5                   10                  15

Glu Phe Ala Ile Gln Pro Asn Thr Thr Gly Lys Gln Leu Phe Asp Gln
                20                  25                  30

Val Val Lys Thr Ile Gly Leu Arg Glu Val Trp Tyr Phe Gly Leu His
                35                  40                  45

Tyr Val Asp Asn Lys Gly Phe Pro Thr Trp Leu Lys Leu Asp Lys Lys
        50                  55                  60

Val Ser Ala Gln Glu Val Arg Lys Glu Asn Pro Leu Gln Phe Lys Phe
65                  70                  75                  80

Arg Ala Lys Phe Tyr Pro Glu Asp Val Ala Glu Glu Leu Ile Gln Asp
                85                  90                  95

Ile Thr Gln Lys Leu Phe Phe Leu Gln Val Lys Glu Gly Ile Leu Ser
                100                 105                 110

Asp Glu Ile Tyr Cys Pro Pro Glu Thr Ala Val Leu Leu Gly Ser Tyr
                115                 120                 125

Ala Val Gln Ala Lys Phe Gly Asp Tyr Asn Lys Glu Val His Lys Ser
                130                 135                 140

Gly Tyr Leu Ser Ser Glu Arg Leu Ile Pro Gln Arg Val Met Asp Gln
```

```
            145                 150                 155                 160
His Lys Leu Thr Arg Asp Gln Trp Glu Asp Arg Ile Gln Val Trp His
                165                 170                 175

Ala Glu His Arg Gly Met Leu Lys Asp Asn Ala Met Leu Glu Tyr Leu
            180                 185                 190

Lys Ile Ala Gln Asp Leu Glu Met Tyr Gly Ile Asn Tyr Phe Glu Ile
            195                 200                 205

Lys Asn Lys Lys Gly Thr Asp Leu Trp Leu Gly Val Asp Ala Leu Gly
            210                 215                 220

Leu Asn Ile Tyr Glu Lys Asp Asp Lys Leu Thr Pro Lys Ile Gly Phe
225                 230                 235                 240

Pro Trp Ser Glu Ile Arg Asn Ile Ser Phe Asn Asp Lys Lys Phe Val
                245                 250                 255

Ile Lys Pro Ile Asp Lys Lys Ala Pro Asp Phe Val Phe Tyr Ala Pro
                260                 265                 270

Arg Leu Arg Ile Asn Lys Arg Ile Leu Gln Leu Cys Met Gly Asn His
                275                 280                 285

Glu Leu Tyr Met Arg Arg Arg Lys Pro Asp Thr Ile Glu Val Gln Gln
            290                 295                 300

Met Lys Ala Gln Ala Arg Glu Glu Lys His Gln Lys Gln Leu Glu Arg
305                 310                 315                 320

Gln Gln Leu Glu Thr Glu Lys Lys Arg Arg Glu Thr Val Glu Arg Glu
                325                 330                 335

Lys Glu Gln Met Met Arg Glu Lys Glu Glu Leu Met Leu Arg Leu Gln
                340                 345                 350

Asp Tyr Glu Glu Lys Thr Lys Lys Ala Glu Arg Glu Leu Ser Glu Gln
                355                 360                 365

Ile Gln Arg Ala Leu Gln Leu Glu Glu Glu Arg Lys Arg Ala Gln Glu
            370                 375                 380

Glu Ala Glu Arg Leu Glu Ala Asp Arg Met Ala Ala Leu Arg Ala Lys
385                 390                 395                 400

Glu Glu Leu Glu Arg Gln Ala Val Asp Gln Ile Lys Ser Gln Glu Gln
                405                 410                 415

Leu Ala Ala Glu Leu Ala Glu Tyr Thr Ala Lys Ile Ala Leu Leu Glu
            420                 425                 430

Glu Ala Arg Arg Arg Lys Glu Asp Glu Val Glu Glu Trp Gln His Arg
            435                 440                 445

Ala Lys Glu Ala Gln Asp Asp Leu Val Lys Thr Lys Glu Glu Leu His
            450                 455                 460

Leu Val Met Thr Ala Pro Pro Pro Pro Pro Pro Val Tyr Glu Pro
465                 470                 475                 480

Val Ser Tyr His Val Gln Glu Ser Leu Gln Asp Glu Gly Ala Glu Pro
                485                 490                 495

Thr Gly Tyr Ser Ala Glu Leu Ser Ser Glu Gly Ile Arg Asp Asp Arg
            500                 505                 510

Asn Glu Glu Lys Arg Ile Thr Glu Ala Glu Lys Asn Glu Arg Val Gln
            515                 520                 525

Arg Gln Leu Val Thr Leu Ser Ser Glu Leu Ser Gln Ala Arg Asp Glu
            530                 535                 540

Asn Lys Arg Thr His Asn Asp Ile Ile His Asn Glu Asn Met Arg Gln
545                 550                 555                 560

Gly Arg Asp Lys Tyr Lys Thr Leu Arg Gln Ile Arg Gln Gly Asn Thr
                565                 570                 575
```

```
Lys Gln Arg Ile Asp Glu Phe Glu Ala Leu
                580                 585

<210> SEQ ID NO 41
<211> LENGTH: 583
<212> TYPE: PRT
<213> ORGANISM: Homo sapiens

<400> SEQUENCE: 41

Met Pro Lys Pro Ile Asn Val Arg Val Thr Thr Met Asp Ala Glu Leu
1               5                   10                  15

Glu Phe Ala Ile Gln Pro Asn Thr Thr Gly Lys Gln Leu Phe Asp Gln
                20                  25                  30

Val Val Lys Thr Val Gly Leu Arg Glu Val Trp Phe Phe Gly Leu Gln
                35                  40                  45

Tyr Val Asp Ser Lys Gly Tyr Ser Thr Trp Leu Lys Leu Asn Lys Lys
            50                  55                  60

Val Thr Gln Gln Asp Val Lys Lys Glu Asn Pro Leu Gln Phe Lys Phe
65                  70                  75                  80

Arg Ala Lys Phe Phe Pro Glu Asp Val Ser Glu Glu Leu Ile Gln Glu
                85                  90                  95

Ile Thr Gln Arg Leu Phe Phe Leu Gln Val Lys Glu Ala Ile Leu Asn
                100                 105                 110

Asp Glu Ile Tyr Cys Pro Pro Glu Thr Ala Val Leu Leu Ala Ser Tyr
                115                 120                 125

Ala Val Gln Ala Lys Tyr Gly Asp Tyr Asn Lys Glu Ile His Lys Pro
            130                 135                 140

Gly Tyr Leu Ala Asn Asp Arg Leu Leu Pro Gln Arg Val Leu Glu Gln
145                 150                 155                 160

His Lys Leu Thr Lys Glu Gln Trp Glu Glu Arg Ile Gln Asn Trp His
                165                 170                 175

Glu Glu His Arg Gly Met Leu Arg Glu Asp Ser Met Met Glu Tyr Leu
                180                 185                 190

Lys Ile Ala Gln Asp Leu Glu Met Tyr Gly Val Asn Tyr Phe Glu Ile
                195                 200                 205

Lys Asn Lys Lys Gly Thr Glu Leu Trp Leu Gly Val Asp Ala Leu Gly
            210                 215                 220

Leu Asn Ile Tyr Glu His Asp Asp Lys Leu Thr Pro Lys Ile Gly Phe
225                 230                 235                 240

Pro Trp Ser Glu Ile Arg Asn Ile Ser Phe Asn Asp Lys Lys Phe Val
                245                 250                 255

Ile Lys Pro Ile Asp Lys Lys Ala Pro Asp Phe Val Phe Tyr Ala Pro
                260                 265                 270

Arg Leu Arg Ile Asn Lys Arg Ile Leu Ala Leu Cys Met Gly Asn His
                275                 280                 285

Glu Leu Tyr Met Arg Arg Arg Lys Pro Asp Thr Ile Glu Val Gln Gln
            290                 295                 300

Met Lys Ala Gln Ala Arg Glu Glu Lys His Gln Lys Gln Leu Glu Arg
305                 310                 315                 320

Ala Gln Leu Glu Asn Glu Lys Glu Arg Glu Ile Ala Lys Glu
                325                 330                 335

Lys Glu Arg Ile Glu Arg Glu Lys Glu Glu Leu Met Glu Arg Leu Lys
                340                 345                 350

Gln Ile Glu Glu Gln Thr Ile Lys Ala Gln Lys Glu Leu Glu Glu Gln
            355                 360                 365
```

```
Thr Arg Lys Ala Leu Glu Leu Asp Gln Glu Arg Lys Arg Ala Lys Glu
        370                 375                 380

Glu Ala Glu Arg Leu Glu Lys Glu Arg Arg Ala Glu Glu Ala Glu Lys
385                 390                 395                 400

Ser Ala Ile Ala Lys Gln Ala Ala Asp Gln Met Lys Asn Gln Glu Gln
                405                 410                 415

Leu Ala Ala Glu Leu Ala Glu Phe Thr Ala Lys Ile Ala Leu Leu Glu
                420                 425                 430

Glu Ala Lys Lys Lys Lys Glu Glu Ala Thr Glu Trp Gln His Lys
                435                 440                 445

Ala Phe Ala Ala Gln Glu Asp Leu Glu Lys Thr Lys Glu Glu Leu Lys
        450                 455                 460

Thr Val Met Ser Ala Pro Pro Pro Pro Pro Pro Val Ile Pro
465                 470                 475                 480

Pro Thr Glu Asn Glu His Asp Glu His Asp Glu Asn Asn Ala Glu Ala
                485                 490                 495

Ser Ala Glu Leu Ser Asn Glu Gly Val Met Asn His Arg Ser Glu Glu
                500                 505                 510

Glu Arg Val Thr Glu Thr Gln Lys Asn Glu Arg Val Lys Lys Gln Leu
        515                 520                 525

Gln Ala Leu Ser Ser Glu Leu Ala Gln Ala Arg Asp Glu Thr Lys Lys
        530                 535                 540

Thr Gln Asn Asp Val Leu His Ala Glu Asn Val Lys Ala Gly Arg Asp
545                 550                 555                 560

Lys Tyr Lys Thr Leu Arg Gln Ile Arg Gln Gly Asn Thr Lys Gln Arg
                565                 570                 575

Ile Asp Glu Phe Glu Ala Met
                580

<210> SEQ ID NO 42
<211> LENGTH: 595
<212> TYPE: PRT
<213> ORGANISM: Homo sapiens

<400> SEQUENCE: 42

Met Ala Gly Ala Ile Ala Ser Arg Met Ser Phe Ser Ser Leu Lys Arg
1               5                   10                  15

Lys Gln Pro Lys Thr Phe Thr Val Arg Ile Val Thr Met Asp Ala Glu
                20                  25                  30

Met Glu Phe Asn Cys Glu Met Lys Trp Lys Gly Lys Asp Leu Phe Asp
            35                  40                  45

Leu Val Cys Arg Thr Leu Gly Leu Arg Glu Thr Trp Phe Phe Gly Leu
    50                  55                  60

Gln Tyr Thr Ile Lys Asp Thr Val Ala Trp Leu Lys Met Asp Lys Lys
65                  70                  75                  80

Val Leu Asp His Asp Val Ser Lys Glu Glu Pro Val Thr Phe His Phe
                85                  90                  95

Leu Ala Lys Phe Tyr Pro Glu Asn Ala Glu Glu Leu Val Gln Glu
                100                 105                 110

Ile Thr Gln His Leu Phe Phe Leu Gln Val Lys Lys Gln Ile Leu Asp
            115                 120                 125

Glu Lys Ile Tyr Cys Pro Pro Glu Ala Ser Val Leu Leu Ala Ser Tyr
    130                 135                 140

Ala Val Gln Ala Lys Tyr Gly Asp Tyr Asp Pro Ser Val His Lys Arg
145                 150                 155                 160
```

-continued

```
Gly Phe Leu Ala Gln Glu Glu Leu Leu Pro Lys Arg Val Ile Asn Leu
                165                 170                 175

Tyr Gln Met Thr Pro Glu Met Trp Glu Arg Ile Thr Ala Trp Tyr
            180                 185                 190

Ala Glu His Arg Gly Arg Ala Arg Asp Glu Ala Glu Met Glu Tyr Leu
            195                 200                 205

Lys Ile Ala Gln Asp Leu Glu Met Tyr Gly Val Asn Tyr Phe Ala Ile
            210                 215                 220

Arg Asn Lys Lys Gly Thr Glu Leu Leu Leu Gly Val Asp Ala Leu Gly
225                 230                 235                 240

Leu His Ile Tyr Asp Pro Glu Asn Arg Leu Thr Pro Lys Ile Ser Phe
                245                 250                 255

Pro Trp Asn Glu Ile Arg Asn Ile Ser Tyr Ser Asp Lys Glu Phe Thr
                260                 265                 270

Ile Lys Pro Leu Asp Lys Lys Ile Asp Val Phe Lys Phe Asn Ser Ser
            275                 280                 285

Lys Leu Arg Val Asn Lys Leu Ile Leu Gln Leu Cys Ile Gly Asn His
            290                 295                 300

Asp Leu Phe Met Arg Arg Lys Ala Asp Ser Leu Glu Val Gln Gln
305                 310                 315                 320

Met Lys Ala Gln Ala Arg Glu Glu Lys Ala Arg Lys Gln Met Glu Arg
                325                 330                 335

Gln Arg Leu Ala Arg Glu Lys Gln Met Arg Glu Ala Glu Arg Thr
            340                 345                 350

Arg Asp Glu Leu Glu Arg Arg Leu Leu Gln Met Lys Glu Glu Ala Thr
            355                 360                 365

Met Ala Asn Glu Ala Leu Met Arg Ser Glu Thr Ala Asp Leu Leu
370                 375                 380

Ala Glu Lys Ala Gln Ile Thr Glu Glu Glu Ala Lys Leu Leu Ala Gln
385                 390                 395                 400

Lys Ala Ala Glu Ala Glu Gln Glu Met Gln Arg Ile Lys Ala Thr Ala
                405                 410                 415

Ile Arg Thr Glu Glu Glu Lys Arg Leu Met Glu Gln Lys Val Leu Glu
            420                 425                 430

Ala Glu Val Leu Ala Leu Lys Met Ala Glu Glu Ser Glu Arg Arg Ala
            435                 440                 445

Lys Glu Ala Asp Gln Leu Lys Gln Asp Leu Gln Glu Ala Arg Glu Ala
            450                 455                 460

Glu Arg Arg Ala Lys Gln Lys Leu Leu Glu Ile Ala Thr Lys Pro Thr
465                 470                 475                 480

Tyr Pro Pro Met Asn Pro Ile Pro Ala Pro Leu Pro Pro Asp Ile Pro
                485                 490                 495

Ser Phe Asn Leu Ile Gly Asp Ser Leu Ser Phe Asp Phe Lys Asp Thr
            500                 505                 510

Asp Met Lys Arg Leu Ser Met Glu Ile Glu Lys Glu Lys Val Glu Tyr
            515                 520                 525

Met Glu Lys Ser Lys His Leu Gln Glu Gln Leu Asn Glu Leu Lys Thr
            530                 535                 540

Glu Ile Glu Ala Leu Lys Leu Lys Glu Arg Glu Thr Ala Leu Asp Ile
545                 550                 555                 560

Leu His Asn Glu Asn Ser Asp Arg Gly Gly Ser Ser Lys His Asn Thr
                565                 570                 575

Ile Lys Lys Leu Thr Leu Gln Ser Ala Lys Ser Arg Val Ala Phe Phe
            580                 585                 590
```

Glu Glu Leu
        595

<210> SEQ ID NO 43
<211> LENGTH: 29
<212> TYPE: PRT
<213> ORGANISM: Homo sapiens

<400> SEQUENCE: 43

Met Arg Leu Gly Arg Asp Lys Tyr Lys Thr Leu Arg Gln Ile Arg Gln
1               5                   10                  15

Gly Asn Thr Lys Gln Arg Ile Asp Glu Phe Glu Ser Met
            20                  25

<210> SEQ ID NO 44
<211> LENGTH: 29
<212> TYPE: PRT
<213> ORGANISM: Homo sapiens

<400> SEQUENCE: 44

Met Arg Gln Gly Arg Asp Lys Tyr Lys Thr Leu Arg Gln Ile Arg Gln
1               5                   10                  15

Gly Asn Thr Lys Gln Arg Ile Asp Glu Phe Glu Ala Leu
            20                  25

<210> SEQ ID NO 45
<211> LENGTH: 29
<212> TYPE: PRT
<213> ORGANISM: Homo sapiens

<400> SEQUENCE: 45

Val Lys Ala Gly Arg Asp Lys Tyr Lys Thr Leu Arg Gln Ile Arg Gln
1               5                   10                  15

Gly Asn Thr Lys Gln Arg Ile Asp Glu Phe Glu Ala Met
            20                  25

<210> SEQ ID NO 46
<211> LENGTH: 29
<212> TYPE: PRT
<213> ORGANISM: Homo sapiens

<400> SEQUENCE: 46

Asp Arg Gly Gly Ser Ser Lys His Asn Thr Ile Lys Lys Leu Thr Leu
1               5                   10                  15

Gln Ser Ala Lys Ser Arg Val Ala Phe Phe Glu Glu Leu
            20                  25

<210> SEQ ID NO 47
<211> LENGTH: 17
<212> TYPE: PRT
<213> ORGANISM: Artificial
<220> FEATURE:
<223> OTHER INFORMATION: Recombinant protein

<400> SEQUENCE: 47

Arg Leu Gly Arg Asp Lys Tyr Lys Thr Leu Arg Gln Ile Arg Gln Gly
1               5                   10                  15

Asn

<210> SEQ ID NO 48
<211> LENGTH: 10
<212> TYPE: PRT
<213> ORGANISM: Artificial

```
<220> FEATURE:
<223> OTHER INFORMATION: Recombinant protein

<400> SEQUENCE: 48

Trp Trp Arg Phe Tyr Thr Leu Arg Lys Ala
1               5                   10

<210> SEQ ID NO 49
<211> LENGTH: 21
<212> TYPE: PRT
<213> ORGANISM: Artificial
<220> FEATURE:
<223> OTHER INFORMATION: Recombinant protein

<400> SEQUENCE: 49

Arg Leu Gly Trp Trp Lys Phe Tyr Thr Leu Arg Arg Ala Arg Gln Gly
1               5                   10                  15

Asn Thr Lys Gln Arg
            20

<210> SEQ ID NO 50
<211> LENGTH: 21
<212> TYPE: PRT
<213> ORGANISM: Artificial
<220> FEATURE:
<223> OTHER INFORMATION: Recombinant protein

<400> SEQUENCE: 50

Arg Leu Gly Trp Trp Arg Phe Tyr Thr Leu Arg Lys Ala Arg Gln Gly
1               5                   10                  15

Asn Thr Lys Gln Arg
            20

<210> SEQ ID NO 51
<211> LENGTH: 21
<212> TYPE: PRT
<213> ORGANISM: Artificial
<220> FEATURE:
<223> OTHER INFORMATION: Recombinant protein

<400> SEQUENCE: 51

Arg Leu Gly Trp Trp Arg Phe Tyr Thr Leu Arg Arg Ala Arg Gln Gly
1               5                   10                  15

Asn Thr Lys Gln Arg
            20

<210> SEQ ID NO 52
<211> LENGTH: 10
<212> TYPE: PRT
<213> ORGANISM: Artificial
<220> FEATURE:
<223> OTHER INFORMATION: Recombinant protein
<220> FEATURE:
<221> NAME/KEY: Variation
<222> LOCATION: (1)..(1)
<223> OTHER INFORMATION: Trp, Phe, Arg or Lys
<220> FEATURE:
<221> NAME/KEY: Variation
<222> LOCATION: (2)..(2)
<223> OTHER INFORMATION: Trp, Phe, Arg or Lys
<220> FEATURE:
<221> NAME/KEY: Variation
<222> LOCATION: (3)..(3)
<223> OTHER INFORMATION: Arg or Lys
<220> FEATURE:
<221> NAME/KEY: Variation
<222> LOCATION: (4)..(4)
<223> OTHER INFORMATION: Phe,Trp, His or Arg
<220> FEATURE:
```

```
<221> NAME/KEY: Variation
<222> LOCATION: (5)..(5)
<223> OTHER INFORMATION: Tyr, Trp or Arg
<220> FEATURE:
<221> NAME/KEY: Variation
<222> LOCATION: (6)..(6)
<223> OTHER INFORMATION: Ser or Thr
<220> FEATURE:
<221> NAME/KEY: Variation
<222> LOCATION: (7)..(7)
<223> OTHER INFORMATION: Leu, Val or Ile
<220> FEATURE:
<221> NAME/KEY: Variation
<222> LOCATION: (8)..(8)
<223> OTHER INFORMATION: Arg or Lys
<220> FEATURE:
<221> NAME/KEY: Variation
<222> LOCATION: (9)..(9)
<223> OTHER INFORMATION: Arg or Lys
<220> FEATURE:
<221> NAME/KEY: Variation
<222> LOCATION: (10)..(10)
<223> OTHER INFORMATION: Ala or Tyr

<400> SEQUENCE: 52

Xaa Xaa Xaa Xaa Xaa Xaa Xaa Xaa Xaa Xaa
1               5                   10

<210> SEQ ID NO 53
<211> LENGTH: 21
<212> TYPE: PRT
<213> ORGANISM: Artificial
<220> FEATURE:
<223> OTHER INFORMATION: Recombinant protein

<400> SEQUENCE: 53

Arg Leu Gly Trp Trp Arg Phe Tyr Ala Leu Arg Arg Ala Arg Gln Gly
1               5                   10                  15

Asn Thr Lys Gln Arg
            20

<210> SEQ ID NO 54
<211> LENGTH: 20
<212> TYPE: PRT
<213> ORGANISM: Homo sapiens

<400> SEQUENCE: 54

Leu Lys Lys Leu Ile Val Arg Leu Asn Asn Val Gln Glu Gly Lys Gln
1               5                   10                  15

Ile Glu Thr Leu
            20

<210> SEQ ID NO 55
<211> LENGTH: 22
<212> TYPE: PRT
<213> ORGANISM: Homo sapiens

<400> SEQUENCE: 55

Lys Phe Pro Asn Glu Phe Asp Glu Leu Glu Ile Gln Gly Lys Leu Pro
1               5                   10                  15

Asp Pro Val Lys Glu Tyr
            20

<210> SEQ ID NO 56
<211> LENGTH: 18
<212> TYPE: PRT
<213> ORGANISM: Homo sapiens

<400> SEQUENCE: 56
```

Cys Ile Asn Leu Pro His Glu Val Gln Asn Leu Glu Lys His Ile Glu
1               5                   10                  15

Val Arg

<210> SEQ ID NO 57
<211> LENGTH: 20
<212> TYPE: PRT
<213> ORGANISM: Homo sapiens

<400> SEQUENCE: 57

Glu Lys His Ile Glu Val Arg Lys Glu Leu Ala Glu Lys Met Arg Arg
1               5                   10                  15

Thr Ser Val Glu
            20

<210> SEQ ID NO 58
<211> LENGTH: 14
<212> TYPE: PRT
<213> ORGANISM: Homo sapiens
<220> FEATURE:
<221> NAME/KEY: Phosphorylation
<222> LOCATION: (7)..(7)
<223> OTHER INFORMATION: Phospho serine

<400> SEQUENCE: 58

Val Lys Lys Lys Ser Asn Ser Ile Ser Val Gly Glu Phe Tyr
1               5                   10

<210> SEQ ID NO 59
<211> LENGTH: 15
<212> TYPE: PRT
<213> ORGANISM: Homo sapiens
<220> FEATURE:
<221> NAME/KEY: Phosphorylation
<222> LOCATION: (8)..(8)
<223> OTHER INFORMATION: Phospho threonine

<400> SEQUENCE: 59

Cys Leu Ala Lys Leu Arg Lys Thr Ile Ile Asn Glu Ser Leu Asn
1               5                   10                  15

<210> SEQ ID NO 60
<211> LENGTH: 15
<212> TYPE: PRT
<213> ORGANISM: Homo sapiens
<220> FEATURE:
<221> NAME/KEY: Phosphorylation
<222> LOCATION: (8)..(8)
<223> OTHER INFORMATION: Phospho threonine

<400> SEQUENCE: 60

Cys Leu Ala Lys Leu Arg Lys Thr Ile Ile Asn Glu Ser Leu Asn
1               5                   10                  15

<210> SEQ ID NO 61
<211> LENGTH: 16
<212> TYPE: PRT
<213> ORGANISM: Mus sp.

<400> SEQUENCE: 61

Cys Arg Val Glu Lys Leu His Leu Ser His Asn Lys Leu Lys Glu Ile
1               5                   10                  15

<210> SEQ ID NO 62
<211> LENGTH: 19
<212> TYPE: PRT

<210> SEQ ID NO 62
<211> LENGTH: 18
<212> TYPE: PRT
<213> ORGANISM: Mus sp.

<400> SEQUENCE: 62

Cys Phe Pro Asn Glu Phe Asp Glu Leu Ala Ile Gln Gly Lys Leu Pro
1               5                   10                  15

Asp Pro Val

<210> SEQ ID NO 63
<211> LENGTH: 19
<212> TYPE: PRT
<213> ORGANISM: Mus sp.

<400> SEQUENCE: 63

Cys Phe Pro Asn Glu Phe Asp Glu Leu Ala Ile Gln Gly Lys Leu Pro
1               5                   10                  15

Asp Pro Val

<210> SEQ ID NO 64
<211> LENGTH: 22
<212> TYPE: PRT
<213> ORGANISM: Mus sp.

<400> SEQUENCE: 64

Arg Phe Pro Asn Glu Phe Asp Glu Leu Ala Ile Gln Gly Lys Leu Pro
1               5                   10                  15

Asp Pro Val Lys Glu Tyr
            20

<210> SEQ ID NO 65
<211> LENGTH: 10
<212> TYPE: PRT
<213> ORGANISM: Artificial
<220> FEATURE:
<223> OTHER INFORMATION: Recombinant protein

<400> SEQUENCE: 65

Trp Trp Arg Phe Tyr Thr Leu Arg Arg Ala
1               5                   10

<210> SEQ ID NO 66
<211> LENGTH: 404
<212> TYPE: PRT
<213> ORGANISM: Artificial
<220> FEATURE:
<223> OTHER INFORMATION: Recombinant protein

<400> SEQUENCE: 66

Gly Pro Leu Gly Ser Met Gly Pro Gln Asp Val Gly Asn Asp Trp Glu
1               5                   10                  15

Val Leu Gly Val His Gln Leu Ile Leu Lys Met Leu Thr Val His Asn
                20                  25                  30

Ala Ser Val Asn Leu Ser Val Ile Gly Leu Lys Thr Leu Asp Leu Leu
            35                  40                  45

Leu Thr Ser Gly Lys Ile Thr Leu Leu Ile Leu Asp Glu Glu Ser Asp
        50                  55                  60

Ile Phe Met Leu Ile Phe Asp Ala Met His Ser Phe Pro Ala Asn Asp
65                  70                  75                  80

Glu Val Gln Lys Leu Gly Cys Lys Ala Leu His Val Leu Phe Glu Arg
                85                  90                  95

Val Ser Glu Glu Gln Leu Thr Gly Phe Val Glu Asn Lys Asp Tyr Met
                100                 105                 110

-continued

```
Ile Leu Leu Ser Ala Leu Thr Asn Phe Lys Asp Glu Glu Ile Val
        115                 120                 125
Leu His Val Leu His Cys Leu His Ser Leu Ala Ile Pro Cys Asn Asn
    130                 135                 140
Val Glu Val Leu Met Ser Gly Asn Val Arg Cys Tyr Asn Ile Val Val
145                 150                 155                 160
Glu Ala Met Lys Ala Phe Pro Met Ser Glu Arg Ile Gln Glu Val Ser
                165                 170                 175
Cys Cys Leu Leu His Arg Leu Thr Leu Gly Asn Phe Phe Asn Ile Leu
            180                 185                 190
Val Leu Asn Glu Val His Glu Phe Val Val Lys Ala Val Gln Gln Tyr
        195                 200                 205
Pro Glu Asn Ala Ala Leu Gln Ile Ser Ala Leu Ser Cys Leu Ala Leu
    210                 215                 220
Leu Thr Glu Thr Ile Phe Leu Asn Gln Asp Leu Glu Glu Lys Asn Glu
225                 230                 235                 240
Asn Gln Glu Asn Asp Asp Glu Gly Glu Asp Lys Leu Phe Trp Leu
                245                 250                 255
Glu Ala Cys Tyr Lys Ala Leu Thr Trp His Arg Lys Asn Lys His Val
            260                 265                 270
Gln Glu Ala Ala Cys Trp Ala Leu Asn Asn Leu Leu Met Tyr Gln Asn
        275                 280                 285
Ser Leu His Glu Lys Ile Gly Asp Glu Asp Gly His Phe Pro Ala His
    290                 295                 300
Arg Glu Val Met Leu Ser Met Leu Met His Ser Ser Lys Glu Val
305                 310                 315                 320
Phe Gln Ala Ser Ala Asn Ala Leu Ser Thr Leu Leu Glu Gln Asn Val
                325                 330                 335
Asn Phe Arg Lys Ile Leu Leu Ser Lys Gly Ile His Leu Asn Val Leu
            340                 345                 350
Glu Leu Met Gln Lys His Ile His Ser Pro Glu Val Ala Glu Ser Gly
        355                 360                 365
Cys Lys Met Leu Asn His Leu Phe Glu Gly Ser Asn Thr Ser Leu Asp
    370                 375                 380
Ile Met Ala Ala Val Val Pro Lys Ile Leu Thr Val Met Lys Arg His
385                 390                 395                 400
Glu Thr Ser Leu
```

```
<210> SEQ ID NO 67
<211> LENGTH: 10
<212> TYPE: PRT
<213> ORGANISM: Artificial
<220> FEATURE:
<223> OTHER INFORMATION: Recombinant protein

<400> SEQUENCE: 67

Trp Trp Lys Phe Tyr Thr Leu Arg Arg Ala
1               5                   10

<210> SEQ ID NO 68
<211> LENGTH: 21
<212> TYPE: PRT
<213> ORGANISM: Artificial Sequence
<220> FEATURE:
<223> OTHER INFORMATION: Recombinant protein
<220> FEATURE:
<221> NAME/KEY: VARIANT
<222> LOCATION: (9)..(9)
<223> OTHER INFORMATION: Ser or Thr
```

```
<400> SEQUENCE: 68

Arg Leu Gly Arg Asp Lys Tyr Lys Xaa Leu Arg Gln Ile Arg Gln Gly
1               5                   10                  15

Asn Thr Lys Gln Arg
            20

<210> SEQ ID NO 69
<211> LENGTH: 2527
<212> TYPE: PRT
<213> ORGANISM: Homo sapiens

<400> SEQUENCE: 69

Met Ala Ser Gly Ser Cys Gln Gly Cys Glu Glu Asp Glu Glu Thr Leu
1               5                   10                  15

Lys Lys Leu Ile Val Arg Leu Asn Asn Val Gln Glu Gly Lys Gln Ile
            20                  25                  30

Glu Thr Leu Val Gln Ile Leu Glu Asp Leu Leu Val Phe Thr Tyr Ser
        35                  40                  45

Glu His Ala Ser Lys Leu Phe Gln Gly Lys Asn Ile His Val Pro Leu
    50                  55                  60

Leu Ile Val Leu Asp Ser Tyr Met Arg Val Ala Ser Val Gln Gln Val
65                  70                  75                  80

Gly Trp Ser Leu Leu Cys Lys Leu Ile Glu Val Cys Pro Gly Thr Met
                85                  90                  95

Gln Ser Leu Met Gly Pro Gln Asp Val Gly Asn Asp Trp Glu Val Leu
            100                 105                 110

Gly Val His Gln Leu Ile Leu Lys Met Leu Thr Val His Asn Ala Ser
        115                 120                 125

Val Asn Leu Ser Val Ile Gly Leu Lys Thr Leu Asp Leu Leu Leu Thr
    130                 135                 140

Ser Gly Lys Ile Thr Leu Leu Ile Leu Asp Glu Glu Ser Asp Ile Phe
145                 150                 155                 160

Met Leu Ile Phe Asp Ala Met His Ser Phe Pro Ala Asn Asp Glu Val
                165                 170                 175

Gln Lys Leu Gly Cys Lys Ala Leu His Val Leu Phe Glu Arg Val Ser
            180                 185                 190

Glu Glu Gln Leu Thr Glu Phe Val Glu Asn Lys Asp Tyr Met Ile Leu
        195                 200                 205

Leu Ser Ala Ser Thr Asn Phe Lys Asp Glu Glu Glu Ile Val Leu His
    210                 215                 220

Val Leu His Cys Leu His Ser Leu Ala Ile Pro Cys Asn Asn Val Glu
225                 230                 235                 240

Val Leu Met Ser Gly Asn Val Arg Cys Tyr Asn Ile Val Val Glu Ala
                245                 250                 255

Met Lys Ala Phe Pro Met Ser Glu Arg Ile Gln Glu Val Ser Cys Cys
            260                 265                 270

Leu Leu His Arg Leu Thr Leu Gly Asn Phe Phe Asn Ile Leu Val Leu
        275                 280                 285

Asn Glu Val His Glu Phe Val Val Lys Ala Val Gln Gln Tyr Pro Glu
    290                 295                 300

Asn Ala Ala Leu Gln Ile Ser Ala Leu Ser Cys Leu Ala Leu Leu Thr
305                 310                 315                 320

Glu Thr Ile Phe Leu Asn Gln Asp Leu Glu Glu Lys Asn Glu Asn Gln
                325                 330                 335
```

-continued

```
Glu Asn Asp Asp Glu Gly Glu Asp Lys Leu Phe Trp Leu Glu Ala
            340                 345                 350
Cys Tyr Lys Ala Leu Thr Trp His Arg Lys Asn Lys His Val Gln Glu
            355                 360                 365
Ala Ala Cys Trp Ala Leu Asn Asn Leu Leu Met Tyr Gln Asn Ser Leu
            370                 375                 380
His Glu Lys Ile Gly Asp Glu Asp Gly His Phe Pro Ala His Arg Glu
385                 390                 395                 400
Val Met Leu Ser Met Leu Met His Ser Ser Lys Glu Val Phe Gln
            405                 410                 415
Ala Ser Ala Asn Ala Leu Ser Thr Leu Leu Glu Gln Asn Val Asn Phe
            420                 425                 430
Arg Lys Ile Leu Leu Ser Lys Gly Ile His Leu Asn Val Leu Glu Leu
            435                 440                 445
Met Gln Lys His Ile His Ser Pro Glu Val Ala Glu Ser Gly Cys Lys
            450                 455                 460
Met Leu Asn His Leu Phe Glu Gly Ser Asn Thr Ser Leu Asp Ile Met
465                 470                 475                 480
Ala Ala Val Val Pro Lys Ile Leu Thr Val Met Lys Arg His Glu Thr
            485                 490                 495
Ser Leu Pro Val Gln Leu Glu Ala Leu Arg Ala Ile Leu His Phe Ile
            500                 505                 510
Val Pro Gly Met Pro Glu Glu Ser Arg Glu Asp Thr Glu Phe His His
            515                 520                 525
Lys Leu Asn Met Val Lys Lys Gln Cys Phe Lys Asn Asp Ile His Lys
530                 535                 540
Leu Val Leu Ala Ala Leu Asn Arg Phe Ile Gly Asn Pro Gly Ile Gln
545                 550                 555                 560
Lys Cys Gly Leu Lys Val Ile Ser Ser Ile Val His Phe Pro Asp Ala
            565                 570                 575
Leu Glu Met Leu Ser Leu Glu Gly Ala Met Asp Ser Val Leu His Thr
            580                 585                 590
Leu Gln Met Tyr Pro Asp Asp Gln Glu Ile Gln Cys Leu Gly Leu Ser
            595                 600                 605
Leu Ile Gly Tyr Leu Ile Thr Lys Lys Asn Val Phe Ile Gly Thr Gly
610                 615                 620
His Leu Leu Ala Lys Ile Leu Val Ser Ser Leu Tyr Arg Phe Lys Asp
625                 630                 635                 640
Val Ala Glu Ile Gln Thr Lys Gly Phe Gln Thr Ile Leu Ala Ile Leu
            645                 650                 655
Lys Leu Ser Ala Ser Phe Ser Lys Leu Leu Val His His Ser Phe Asp
            660                 665                 670
Leu Val Ile Phe His Gln Met Ser Ser Asn Ile Met Glu Gln Lys Asp
            675                 680                 685
Gln Gln Phe Leu Asn Leu Cys Cys Lys Cys Phe Ala Lys Val Ala Met
            690                 695                 700
Asp Asp Tyr Leu Lys Asn Val Met Leu Glu Arg Ala Cys Asp Gln Asn
705                 710                 715                 720
Asn Ser Ile Met Val Glu Cys Leu Leu Leu Gly Ala Asp Ala Asn
            725                 730                 735
Gln Ala Lys Glu Gly Ser Ser Leu Ile Cys Gln Val Cys Glu Lys Glu
            740                 745                 750
Ser Ser Pro Lys Leu Val Glu Leu Leu Leu Asn Ser Gly Ser Arg Glu
            755                 760                 765
```

```
Gln Asp Val Arg Lys Ala Leu Thr Ile Ser Ile Gly Lys Gly Asp Ser
    770                 775                 780

Gln Ile Ile Ser Leu Leu Arg Arg Leu Ala Leu Asp Val Ala Asn
785                 790                 795                 800

Asn Ser Ile Cys Leu Gly Gly Phe Cys Ile Gly Lys Val Glu Pro Ser
                805                 810                 815

Trp Leu Gly Pro Leu Phe Pro Asp Lys Thr Ser Asn Leu Arg Lys Gln
            820                 825                 830

Thr Asn Ile Ala Ser Thr Leu Ala Arg Met Val Ile Arg Tyr Gln Met
                835                 840                 845

Lys Ser Ala Val Glu Glu Gly Thr Ala Ser Gly Ser Asp Gly Asn Phe
850                 855                 860

Ser Glu Asp Val Leu Ser Lys Phe Asp Glu Trp Thr Phe Ile Pro Asp
865                 870                 875                 880

Ser Ser Met Asp Ser Val Phe Ala Gln Ser Asp Asp Leu Asp Ser Glu
                885                 890                 895

Gly Ser Glu Gly Ser Phe Leu Val Lys Lys Lys Ser Asn Ser Ile Ser
                900                 905                 910

Val Gly Glu Phe Tyr Arg Asp Ala Val Leu Gln Arg Cys Ser Pro Asn
            915                 920                 925

Leu Gln Arg His Ser Asn Ser Leu Gly Pro Ile Phe Asp His Glu Asp
    930                 935                 940

Leu Leu Lys Arg Lys Arg Lys Ile Leu Ser Ser Asp Asp Ser Leu Arg
945                 950                 955                 960

Ser Ser Lys Leu Gln Ser His Met Arg His Ser Asp Ser Ile Ser Ser
                965                 970                 975

Leu Ala Ser Glu Arg Glu Tyr Ile Thr Ser Leu Asp Leu Ser Ala Asn
                980                 985                 990

Glu Leu Arg Asp Ile Asp Ala Leu  Ser Gln Lys Cys Cys  Ile Ser Val
            995                 1000                 1005

His Leu  Glu His  Leu Glu Lys  Leu Glu Leu His Gln  Asn Ala Leu
    1010                 1015                 1020

Thr Ser  Phe Pro Gln Gln Leu  Cys Glu Thr Leu Lys  Ser Leu Thr
    1025                 1030                 1035

His Leu  Asp Leu His Ser Asn  Lys Phe Thr Ser Phe  Pro Ser Tyr
    1040                 1045                 1050

Leu Leu  Lys Met Ser Cys Ile  Ala Asn Leu Asp Val  Ser Arg Asn
    1055                 1060                 1065

Asp Ile  Gly Pro Ser Val Val  Leu Asp Pro Thr Val  Lys Cys Pro
    1070                 1075                 1080

Thr Leu  Lys Gln Phe Asn Leu  Ser Tyr Asn Gln Leu  Ser Phe Val
    1085                 1090                 1095

Pro Glu  Asn Leu Thr Asp Val  Val Glu Lys Leu Glu  Gln Leu Ile
    1100                 1105                 1110

Leu Glu  Gly Asn Lys Ile Ser  Gly Ile Cys Ser Pro  Leu Arg Leu
    1115                 1120                 1125

Lys Glu  Leu Lys Ile Leu Asn  Leu Ser Lys Asn His  Ile Ser Ser
    1130                 1135                 1140

Leu Ser  Glu Asn Phe Leu Glu  Ala Cys Pro Lys Val  Glu Ser Phe
    1145                 1150                 1155

Ser Ala  Arg Met Asn Phe Leu  Ala Ala Met Pro Phe  Leu Pro Pro
    1160                 1165                 1170

Ser Met  Thr Ile Leu Lys Leu  Ser Gln Asn Lys Phe  Ser Cys Ile
```

-continued

```
            1175                1180                1185

Pro Glu Ala Ile Leu Asn Leu Pro His Leu Arg Ser Leu Asp Met
    1190                1195                1200

Ser Ser Asn Asp Ile Gln Tyr Leu Pro Gly Pro Ala His Trp Lys
    1205                1210                1215

Ser Leu Asn Leu Arg Glu Leu Leu Phe Ser His Asn Gln Ile Ser
    1220                1225                1230

Ile Leu Asp Leu Ser Glu Lys Ala Tyr Leu Trp Ser Arg Val Glu
    1235                1240                1245

Lys Leu His Leu Ser His Asn Lys Leu Lys Glu Ile Pro Pro Glu
    1250                1255                1260

Ile Gly Cys Leu Glu Asn Leu Thr Ser Leu Asp Val Ser Tyr Asn
    1265                1270                1275

Leu Glu Leu Arg Ser Phe Pro Asn Glu Met Gly Lys Leu Ser Lys
    1280                1285                1290

Ile Trp Asp Leu Pro Leu Asp Glu Leu His Leu Asn Phe Asp Phe
    1295                1300                1305

Lys His Ile Gly Cys Lys Ala Lys Asp Ile Ile Arg Phe Leu Gln
    1310                1315                1320

Gln Arg Leu Lys Lys Ala Val Pro Tyr Asn Arg Met Lys Leu Met
    1325                1330                1335

Ile Val Gly Asn Thr Gly Ser Gly Lys Thr Thr Leu Leu Gln Gln
    1340                1345                1350

Leu Met Lys Thr Lys Lys Ser Asp Leu Gly Met Gln Ser Ala Thr
    1355                1360                1365

Val Gly Ile Asp Val Lys Asp Trp Pro Ile Gln Ile Arg Asp Lys
    1370                1375                1380

Arg Lys Arg Asp Leu Val Leu Asn Val Trp Asp Phe Ala Gly Arg
    1385                1390                1395

Glu Glu Phe Tyr Ser Thr His Pro His Phe Met Thr Gln Arg Ala
    1400                1405                1410

Leu Tyr Leu Ala Val Tyr Asp Leu Ser Lys Gly Gln Ala Glu Val
    1415                1420                1425

Asp Ala Met Lys Pro Trp Leu Phe Asn Ile Lys Ala Arg Ala Ser
    1430                1435                1440

Ser Ser Pro Val Ile Leu Val Gly Thr His Leu Asp Val Ser Asp
    1445                1450                1455

Glu Lys Gln Arg Lys Ala Cys Met Ser Lys Ile Thr Lys Glu Leu
    1460                1465                1470

Leu Asn Lys Arg Gly Phe Pro Ala Ile Arg Asp Tyr His Phe Val
    1475                1480                1485

Asn Ala Thr Glu Glu Ser Asp Ala Leu Ala Lys Leu Arg Lys Thr
    1490                1495                1500

Ile Ile Asn Glu Ser Leu Asn Phe Lys Ile Arg Asp Gln Leu Val
    1505                1510                1515

Val Gly Gln Leu Ile Pro Asp Cys Tyr Val Glu Leu Glu Lys Ile
    1520                1525                1530

Ile Leu Ser Glu Arg Lys Asn Val Pro Ile Glu Phe Pro Val Ile
    1535                1540                1545

Asp Arg Lys Arg Leu Leu Gln Leu Val Arg Glu Asn Gln Leu Gln
    1550                1555                1560

Leu Asp Glu Asn Glu Leu Pro His Ala Val His Phe Leu Asn Glu
    1565                1570                1575
```

-continued

Ser Gly Val Leu Leu His Phe Gln Asp Pro Ala Leu Gln Leu Ser
1580                1585                1590

Asp Leu Tyr Phe Val Glu Pro Lys Trp Leu Cys Lys Ile Met Ala
1595                1600                1605

Gln Ile Leu Thr Val Lys Val Glu Gly Cys Pro Lys His Pro Lys
1610                1615                1620

Gly Ile Ile Ser Arg Arg Asp Val Glu Lys Phe Leu Ser Lys Lys
1625                1630                1635

Arg Lys Phe Pro Lys Asn Tyr Met Ser Gln Tyr Phe Lys Leu Leu
1640                1645                1650

Glu Lys Phe Gln Ile Ala Leu Pro Ile Gly Glu Glu Tyr Leu Leu
1655                1660                1665

Val Pro Ser Ser Leu Ser Asp His Arg Pro Val Ile Glu Leu Pro
1670                1675                1680

His Cys Glu Asn Ser Glu Ile Ile Ile Arg Leu Tyr Glu Met Pro
1685                1690                1695

Tyr Phe Pro Met Gly Phe Trp Ser Arg Leu Ile Asn Arg Leu Leu
1700                1705                1710

Glu Ile Ser Pro Tyr Met Leu Ser Gly Arg Glu Arg Ala Leu Arg
1715                1720                1725

Pro Asn Arg Met Tyr Trp Arg Gln Gly Ile Tyr Leu Asn Trp Ser
1730                1735                1740

Pro Glu Ala Tyr Cys Leu Val Gly Ser Glu Val Leu Asp Asn His
1745                1750                1755

Pro Glu Ser Phe Leu Lys Ile Thr Val Pro Ser Cys Arg Lys Gly
1760                1765                1770

Cys Ile Leu Leu Gly Gln Val Val Asp His Ile Asp Ser Leu Met
1775                1780                1785

Glu Glu Trp Phe Pro Gly Leu Leu Glu Ile Asp Ile Cys Gly Glu
1790                1795                1800

Gly Glu Thr Leu Leu Lys Lys Trp Ala Leu Tyr Ser Phe Asn Asp
1805                1810                1815

Gly Glu Glu His Gln Lys Ile Leu Leu Asp Asp Leu Met Lys Lys
1820                1825                1830

Ala Glu Glu Gly Asp Leu Leu Val Asn Pro Asp Gln Pro Arg Leu
1835                1840                1845

Thr Ile Pro Ile Ser Gln Ile Ala Pro Asp Leu Ile Leu Ala Asp
1850                1855                1860

Leu Pro Arg Asn Ile Met Leu Asn Asn Asp Glu Leu Glu Phe Glu
1865                1870                1875

Gln Ala Pro Glu Phe Leu Leu Gly Asp Gly Ser Phe Gly Ser Val
1880                1885                1890

Tyr Arg Ala Ala Tyr Glu Gly Glu Glu Val Ala Val Lys Ile Phe
1895                1900                1905

Asn Lys His Thr Ser Leu Arg Leu Leu Arg Gln Glu Leu Val Val
1910                1915                1920

Leu Cys His Leu His His Pro Ser Leu Ile Ser Leu Leu Ala Ala
1925                1930                1935

Gly Ile Arg Pro Arg Met Leu Val Met Glu Leu Ala Ser Lys Gly
1940                1945                1950

Ser Leu Asp Arg Leu Leu Gln Gln Asp Lys Ala Ser Leu Thr Arg
1955                1960                1965

Thr Leu Gln His Arg Ile Ala Leu His Val Ala Asp Gly Leu Arg
1970                1975                1980

Tyr Leu His Ser Ala Met Ile  Ile Tyr Arg Asp Leu  Lys Pro His
    1985             1990              1995

Asn Val Leu Leu Phe Thr Leu  Tyr Pro Asn Ala Ala  Ile Ile Ala
    2000             2005              2010

Lys Ile Ala Asp Tyr Gly Ile  Ala Gln Tyr Cys Cys  Arg Met Gly
    2015             2020              2025

Ile Lys Thr Ser Glu Gly Thr  Pro Gly Phe Arg Ala  Pro Glu Val
    2030             2035              2040

Ala Arg Gly Asn Val Ile Tyr  Asn Gln Gln Ala Asp  Val Tyr Ser
    2045             2050              2055

Phe Gly Leu Leu Leu Tyr Asp  Ile Leu Thr Thr Gly  Gly Arg Ile
    2060             2065              2070

Val Glu Gly Leu Lys Phe Pro  Asn Glu Phe Asp Glu  Leu Glu Ile
    2075             2080              2085

Gln Gly Lys Leu Pro Asp Pro  Val Lys Glu Tyr Gly  Cys Ala Pro
    2090             2095              2100

Trp Pro Met Val Glu Lys Leu  Ile Lys Gln Cys Leu  Lys Glu Asn
    2105             2110              2115

Pro Gln Glu Arg Pro Thr Ser  Ala Gln Val Phe Asp  Ile Leu Asn
    2120             2125              2130

Ser Ala Glu Leu Val Cys Leu  Thr Arg Arg Ile Leu  Leu Pro Lys
    2135             2140              2145

Asn Val Ile Val Glu Cys Met  Val Ala Thr His His  Asn Ser Arg
    2150             2155              2160

Asn Ala Ser Ile Trp Leu Gly  Cys Gly His Thr Asp  Arg Gly Gln
    2165             2170              2175

Leu Ser Phe Leu Asp Leu Asn  Thr Glu Gly Tyr Thr  Ser Glu Glu
    2180             2185              2190

Val Ala Asp Ser Arg Ile Leu  Cys Leu Ala Leu Val  His Leu Pro
    2195             2200              2205

Val Glu Lys Glu Ser Trp Ile  Val Ser Gly Thr Gln  Ser Gly Thr
    2210             2215              2220

Leu Leu Val Ile Asn Thr Glu  Asp Gly Lys Lys Arg  His Thr Leu
    2225             2230              2235

Glu Lys Met Thr Asp Ser Val  Thr Cys Leu Tyr Cys  Asn Ser Phe
    2240             2245              2250

Ser Lys Gln Ser Lys Gln Lys  Asn Phe Leu Leu Val  Gly Thr Ala
    2255             2260              2265

Asp Gly Lys Leu Ala Ile Phe  Glu Asp Lys Thr Val  Lys Leu Lys
    2270             2275              2280

Gly Ala Ala Pro Leu Lys Ile  Leu Asn Ile Gly Asn  Val Ser Thr
    2285             2290              2295

Pro Leu Met Cys Leu Ser Glu  Ser Thr Asn Ser Thr  Glu Arg Asn
    2300             2305              2310

Val Met Trp Gly Gly Cys Gly  Thr Lys Ile Phe Ser  Phe Ser Asn
    2315             2320              2325

Asp Phe Thr Ile Gln Lys Leu  Ile Glu Thr Arg Thr  Ser Gln Leu
    2330             2335              2340

Phe Ser Tyr Ala Ala Phe Ser  Asp Ser Asn Ile Ile  Thr Val Val
    2345             2350              2355

Val Asp Thr Ala Leu Tyr Ile  Ala Lys Gln Asn Ser  Pro Val Val
    2360             2365              2370

Glu Val Trp Asp Lys Lys Thr  Glu Lys Leu Cys Gly  Leu Ile Asp

```
                    2375                2380                2385

Cys Val His Phe Leu Arg Glu Val Met Val Lys Glu Asn Lys Glu
        2390                2395                2400

Ser Lys His Lys Met Ser Tyr Ser Gly Arg Val Lys Thr Leu Cys
        2405                2410                2415

Leu Gln Lys Asn Thr Ala Leu Trp Ile Gly Thr Gly Gly His
        2420                2425                2430

Ile Leu Leu Leu Asp Leu Ser Thr Arg Arg Leu Ile Arg Val Ile
        2435                2440                2445

Tyr Asn Phe Cys Asn Ser Val Arg Val Met Met Thr Ala Gln Leu
        2450                2455                2460

Gly Ser Leu Lys Asn Val Met Leu Val Leu Gly Tyr Asn Arg Lys
        2465                2470                2475

Asn Thr Glu Gly Thr Gln Lys Gln Lys Glu Ile Gln Ser Cys Leu
        2480                2485                2490

Thr Val Trp Asp Ile Asn Leu Pro His Glu Val Gln Asn Leu Glu
        2495                2500                2505

Lys His Ile Glu Val Arg Lys Glu Leu Ala Glu Lys Met Arg Arg
        2510                2515                2520

Thr Ser Val Glu
        2525

<210> SEQ ID NO 70
<211> LENGTH: 586
<212> TYPE: PRT
<213> ORGANISM: Homo sapiens

<400> SEQUENCE: 70

Met Pro Lys Pro Ile Asn Val Arg Val Thr Thr Met Asp Ala Glu Leu
1               5                   10                  15

Glu Phe Ala Ile Gln Pro Asn Thr Thr Gly Lys Gln Leu Phe Asp Gln
            20                  25                  30

Val Val Lys Thr Ile Gly Leu Arg Glu Val Trp Tyr Phe Gly Leu His
        35                  40                  45

Tyr Val Asp Asn Lys Gly Phe Pro Thr Trp Leu Lys Leu Asp Lys Lys
    50                  55                  60

Val Ser Ala Gln Glu Val Arg Lys Glu Asn Pro Leu Gln Phe Lys Phe
65                  70                  75                  80

Arg Ala Lys Phe Tyr Pro Glu Asp Val Ala Glu Glu Leu Ile Gln Asp
                85                  90                  95

Ile Thr Gln Lys Leu Phe Phe Leu Gln Val Lys Glu Gly Ile Leu Ser
            100                 105                 110

Asp Glu Ile Tyr Cys Pro Pro Glu Thr Ala Val Leu Leu Gly Ser Tyr
        115                 120                 125

Ala Val Gln Ala Lys Phe Gly Asp Tyr Asn Lys Glu Val His Lys Ser
    130                 135                 140

Gly Tyr Leu Ser Ser Glu Arg Leu Ile Pro Gln Arg Val Met Asp Gln
145                 150                 155                 160

His Lys Leu Thr Arg Asp Gln Trp Glu Asp Arg Ile Gln Val Trp His
                165                 170                 175

Ala Glu His Arg Gly Met Leu Lys Asp Asn Ala Met Leu Glu Tyr Leu
            180                 185                 190

Lys Ile Ala Gln Asp Leu Glu Met Tyr Gly Ile Asn Tyr Phe Glu Ile
        195                 200                 205

Lys Asn Lys Lys Gly Thr Asp Leu Trp Leu Gly Val Asp Ala Leu Gly
```

```
                    210                 215                 220
Leu Asn Ile Tyr Glu Lys Asp Asp Lys Leu Thr Pro Lys Ile Gly Phe
225                 230                 235                 240

Pro Trp Ser Glu Ile Arg Asn Ile Ser Phe Asn Asp Lys Lys Phe Val
                    245                 250                 255

Ile Lys Pro Ile Asp Lys Lys Ala Pro Asp Phe Val Phe Tyr Ala Pro
                260                 265                 270

Arg Leu Arg Ile Asn Lys Arg Ile Leu Gln Leu Cys Met Gly Asn His
                275                 280                 285

Glu Leu Tyr Met Arg Arg Lys Pro Asp Thr Ile Glu Val Gln Gln
290                 295                 300

Met Lys Ala Gln Ala Arg Glu Glu Lys His Gln Lys Gln Leu Glu Arg
305                 310                 315                 320

Gln Gln Leu Glu Thr Glu Lys Lys Arg Arg Glu Thr Val Glu Arg Glu
                325                 330                 335

Lys Glu Gln Met Met Arg Glu Lys Glu Glu Leu Met Leu Arg Leu Gln
                340                 345                 350

Asp Tyr Glu Glu Lys Thr Lys Lys Ala Glu Arg Glu Leu Ser Glu Gln
                355                 360                 365

Ile Gln Arg Ala Leu Gln Leu Glu Glu Glu Arg Lys Arg Ala Gln Glu
370                 375                 380

Glu Ala Glu Arg Leu Glu Ala Asp Arg Met Ala Ala Leu Arg Ala Lys
385                 390                 395                 400

Glu Glu Leu Glu Arg Gln Ala Val Asp Gln Ile Lys Ser Gln Glu Gln
                405                 410                 415

Leu Ala Ala Glu Leu Ala Glu Tyr Thr Ala Lys Ile Ala Leu Leu Glu
                420                 425                 430

Glu Ala Arg Arg Arg Lys Glu Asp Glu Val Glu Glu Trp Gln His Arg
435                 440                 445

Ala Lys Glu Ala Gln Asp Asp Leu Val Lys Thr Lys Glu Glu Leu His
                450                 455                 460

Leu Val Met Thr Ala Pro Pro Pro Pro Pro Pro Val Tyr Glu Pro
465                 470                 475                 480

Val Ser Tyr His Val Gln Glu Ser Leu Gln Asp Glu Gly Ala Glu Pro
                485                 490                 495

Thr Gly Tyr Ser Ala Glu Leu Ser Ser Glu Gly Ile Arg Asp Asp Arg
                500                 505                 510

Asn Glu Glu Lys Arg Ile Thr Glu Ala Glu Lys Asn Glu Arg Val Gln
                515                 520                 525

Arg Gln Leu Leu Thr Leu Ser Ser Glu Leu Ser Gln Ala Arg Asp Glu
530                 535                 540

Asn Lys Arg Thr His Asn Asp Ile Ile His Asn Glu Asn Met Arg Gln
545                 550                 555                 560

Gly Arg Asp Lys Tyr Lys Thr Leu Arg Gln Ile Arg Gln Gly Asn Thr
                565                 570                 575

Lys Gln Arg Ile Asp Glu Phe Glu Ala Leu
                580                 585

<210> SEQ ID NO 71
<211> LENGTH: 10
<212> TYPE: PRT
<213> ORGANISM: Artificial Sequence
<220> FEATURE:
<223> OTHER INFORMATION: Recombinant protein
<220> FEATURE:
<221> NAME/KEY: VARIATION
```

```
<222> LOCATION: (1)..(1)
<223> OTHER INFORMATION: Trp or Arg
<220> FEATURE:
<221> NAME/KEY: VARIATION
<222> LOCATION: (2)..(2)
<223> OTHER INFORMATION: Any amino acid
<220> FEATURE:
<221> NAME/KEY: VARIATION
<222> LOCATION: (3)..(3)
<223> OTHER INFORMATION: Any amino acid
<220> FEATURE:
<221> NAME/KEY: VARIATION
<222> LOCATION: (4)..(4)
<223> OTHER INFORMATION: Phe, Tyr, His or Thr
<220> FEATURE:
<221> NAME/KEY: VARIATION
<222> LOCATION: (5)..(5)
<223> OTHER INFORMATION: Tyr, Trp or Arg
<220> FEATURE:
<221> NAME/KEY: VARIATION
<222> LOCATION: (7)..(7)
<223> OTHER INFORMATION: Any amino acid
<220> FEATURE:
<221> NAME/KEY: VARIATION
<222> LOCATION: (8)..(8)
<223> OTHER INFORMATION: Arg or Thr
<220> FEATURE:
<221> NAME/KEY: VARIATION
<222> LOCATION: (10)..(10)
<223> OTHER INFORMATION: Any amino acid

<400> SEQUENCE: 71

Xaa Xaa Xaa Xaa Xaa Thr Xaa Xaa Arg Xaa
1               5                   10

<210> SEQ ID NO 72
<211> LENGTH: 252
<212> TYPE: PRT
<213> ORGANISM: Artificial Sequence
<220> FEATURE:
<223> OTHER INFORMATION: Recombinant protein GST-Nictide

<400> SEQUENCE: 72

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
```

```
                 180                 185                 190
Leu Lys Ser Ser Lys Tyr Ile Ala Trp Pro Leu Gln Gly Trp Gln Ala
            195                 200                 205

Thr Phe Gly Gly Gly Asp His Pro Pro Lys Ser Asp Leu Glu Val Leu
210                 215                 220

Phe Gln Gly Pro Leu Gly Ser Arg Leu Gly Trp Trp Arg Phe Tyr Thr
225                 230                 235                 240

Leu Arg Arg Ala Arg Gln Gly Asn Thr Lys Gln Arg
            245                 250

<210> SEQ ID NO 73
<211> LENGTH: 766
<212> TYPE: DNA
<213> ORGANISM: Artificial Sequence
<220> FEATURE:
<223> OTHER INFORMATION: Nucleotide sequence of GST-Nictide

<400> SEQUENCE: 73
atgtccccta tactaggtta ttggaaaatt aagggccttg tgcaacccac tcgacttctt      60
ttggaatatc ttgaagaaaa atatgaagag catttgtatg agcgcgatga aggtgataaa     120
tggcgaaaca aaaagtttga attgggtttg gagtttccca atcttcctta ttatattgat     180
ggtgatgtta aattaacaca gtctatggcc atcatacgtt atatagctga caagcacaac     240
atgttgggtg gttgtccaaa agagcgtgca gagatttcaa tgcttgaagg agcggttttg     300
gatattagat acggtgtttc gagaattgca tatagtaaag actttgaaac tctcaaagtt     360
gattttctta gcaagctacc tgaaatgctg aaaatgttcg aagatcgttt atgtcataaa     420
acatatttaa atggtgatca tgtaacccat cctgacttca tgttgtatga cgctcttgat     480
gttgttttat acatggaccc aatgtgcctg atgcgttcc caaaattagt ttgttttaaa      540
aaacgtattg aagctatccc acaaattgat aagtacttga atccagcaa gtatatagca      600 tggcctttgc agggctggca agccacgttt ggtggtggcg accatcctcc aaaatcggat     660
ctggaagttc tgttccaggg gcccctggga tccagactag gttggtggag attttataca     720
ctacgacggg ccaggcaggg caatacaaag cagagatagc ggccgc                   766

<210> SEQ ID NO 74
<211> LENGTH: 5026
<212> TYPE: DNA
<213> ORGANISM: Artificial Sequence
<220> FEATURE:
<223> OTHER INFORMATION: DNA sequence of the Gex6-GST-Nictide vector

<400> SEQUENCE: 74
acgttatcga ctgcacggtg caccaatgct tctggcgtca ggcagccatc ggaagctgtg      60
gtatggctgt gcaggtcgta atcactgca taattcgtgt cgctcaaggc gcactcccgt     120
tctggataat gttttttgcg ccgacatcat aacggttctg gcaaatattc tgaaatgagc     180
tgttgacaat taatcatcgg ctcgtataat gtgtggaatt gtgagcggat aacaatttca     240
cacaggaaac agtattcatg tcccctatac taggttattg gaaaattaag gccttgtgc      300 aacccactcg acttcttttg gaatatcttg aagaaaaata tgaagagcat ttgtatgagc     360
gcgatgaagg tgataaatgg cgaaacaaaa gtttgaattg ggtttggag tttcccaatc      420 ttccttatta tattgatggt gatgttaaat taacacagtc tatggccatc atacgttata     480
tagctgacaa gcacaacatg ttgggtggtt gtccaaaaga gcgtgcagag atttcaatgc     540
ttgaaggagc ggttttggat attagatacg gtgtttcgag aattgcatat agtaaagact     600
```

```
ttgaaactct caaagttgat tttcttagca agctacctga aatgctgaaa atgttcgaag    660
atcgtttatg tcataaaaca tatttaaatg gtgatcatgt aacccatcct gacttcatgt    720
tgtatgacgc tcttgatgtt gttttataca tggacccaat gtgcctggat gcgttcccaa    780
aattagtttg ttttaaaaaa cgtattgaag ctatcccaca aattgataag tacttgaaat    840
ccagcaagta tatagcatgg cctttgcagg gctggcaagc cacgtttggt ggtggcgacc    900
atcctccaaa atcggatctg gaagttctgt tccaggggcc cctgggatcc agactaggtt    960
ggtggagatt ttatacacta cgacgggcca ggcagggcaa tacaaagcag agatagcggc   1020
cgcatcgtga ctgactgacg atctgcctcg cgcgtttcgg tgatgacggt gaaaacctct   1080
gacacatgca gctcccggag acggtcacag cttgtctgta agcggatgcc gggagcagac   1140
aagcccgtca gggcgcgtca gcgggtgttg gcgggtgtcg gggcgcagcc atgacccagt   1200
cacgtagcga tagcggagtg tataattctt gaagacgaaa gggcctcgtg atacgcctat   1260
ttttataggt taatgtcatg ataataatgg tttcttagac gtcaggtggc acttttcggg   1320
gaaatgtgcg cggaaccect atttgtttat ttttctaaat acattcaaat atgtatccgc   1380
tcatgagaca ataaccctga taaatgcttc aataatattg aaaaggaag agtatgagta    1440
ttcaacattt ccgtgtcgcc cttattccct tttttgcggc attttgcctt cctgtttttg   1500
ctcacccaga aacgctggtg aaagtaaaag atgctgaaga tcagttgggt gcacgagtgg   1560
gttacatcga actggatctc aacagcggta agatccttga gagttttcgc cccgaagaac   1620
gttttccaat gatgagcact tttaaagttc tgctatgtgg cgcggtatta tcccgtgttg   1680
acgccgggca agagcaactc ggtcgccgca tacactattc tcagaatgac ttggttgagt   1740
actcaccagt cacagaaaag catcttacgg atggcatgac agtaagagaa ttatgcagtg   1800
ctgccataac catgagtgat aacactgcgg ccaacttact tctgacaacg atcggaggac   1860
cgaaggagct aaccgctttt ttgcacaaca tgggggatca tgtaactcgc cttgatcgtt   1920
gggaaccgga gctgaatgaa gccataccaa acgacgagcg tgacaccacg atgcctgcag   1980
caatggcaac aacgttgcgc aaactattaa ctggcgaact acttactcta gcttcccggc   2040
aacaattaat agactggatg gaggcggata agttgcagg accacttctg cgctcggccc    2100
ttccggctgg ctggtttatt gctgataaat ctggagccgg tgagcgtggg tctcgcggta   2160
tcattgcagc actggggcca gatggtaagc cctcccgtat cgtagttatc tacacgacgg   2220
ggagtcaggc aactatggat gaacgaaata gacagatcgc tgagataggt gcctcactga   2280
ttaagcattg gtaactgtca gaccaagttt actcatatat actttagatt gatttaaaac   2340
ttcatttta atttaaaagg atctaggtga agatcctttt tgataatctc atgaccaaaa    2400
tcccttaacg tgagttttcg ttccactgag cgtcagaccc cgtagaaaag atcaaaggat   2460
cttcttgaga tccttttttt ctgcgcgtaa tctgctgctt gcaaacaaaa aaaccaccgc   2520
taccagcggt ggtttgtttg ccggatcaag agctaccaac tcttttccg aaggtaactg    2580
gcttcagcag agcgcagata ccaaatactg tccttctagt gtagccgtag ttaggccacc   2640
acttcaagaa ctctgtagca ccgcctacat acctcgctct gctaatcctg ttaccagtgg   2700
ctgctgccag tggcgataag tcgtgtctta ccgggttgga ctcaagacga tagttaccgg   2760
ataaggcgca gcggtcgggc tgaacggggg gttcgtgcac acagcccagc ttggagcgaa   2820
cgacctacac cgaactgaga tacctacagc gtgagctatg agaaagcgcc acgcttcccg   2880
aagggagaaa ggcggacagg tatccggtaa gcggcagggt cggaacagga gagcgcacga   2940
gggagcttcc agggggaaac gcctggtatc tttatagtcc tgtcgggttt cgccacctct   3000
```

```
gacttgagcg tcgatttttg tgatgctcgt caggggggcg gagcctatgg aaaaacgcca  3060
gcaacgcggc cttttttacgg ttcctggcct tttgctggcc ttttgctcac atgttctttc  3120
ctgcgttatc ccctgattct gtggataacc gtattaccgc ctttgagtga gctgataccg  3180
ctcgccgcag ccgaacgacc gagcgcagcg agtcagtgag cgaggaagcg gaagagcgcc  3240
tgatgcggta ttttctcctt acgcatctgt gcggtatttc acaccgcata aattccgaca  3300
ccatcgaatg gtgcaaaacc tttcgcggta tggcatgata gcgcccggaa gagagtcaat  3360
tcagggtggt gaatgtgaaa ccagtaacgt tatacgatgt cgcagagtat gccggtgtct  3420
cttatcagac cgtttcccgc gtggtgaacc aggccagcca cgtttctgcg aaaacgcggg  3480
aaaaagtgga agcggcgatg gcggagctga attacattcc caaccgcgtg gcacaacaac  3540
tggcgggcaa acagtcgttg ctgattggcg ttgccacctc cagtctggcc ctgcacgcgc  3600
cgtcgcaaat tgtcgcggcg attaaatctc gcgccgatca actgggtgcc agcgtggtgg  3660
tgtcgatggt agaacgaagc ggcgtcgaag cctgtaaagc ggcggtgcac aatcttctcg  3720
cgcaacgcgt cagtgggctg atcattaact atccgctgga tgaccaggat gccattgctg  3780
tggaagctgc ctgcactaat gttccggcgt tatttcttga tgtctctgac cagacaccca  3840
tcaacagtat tattttctcc catgaagacg gtacgcgact gggcgtggag catctggtcg  3900
cattgggtca ccagcaaatc gcgctgttag cgggcccatt aagttctgtc tcggcgcgtc  3960
tgcgtctggc tggctggcat aaatatctca ctcgcaatca aattcagccg atagcggaac  4020
gggaaggcga ctggagtgcc atgtccggtt ttcaacaaac catgcaaatg ctgaatgagg  4080
gcatcgttcc cactgcgatg ctggttgcca acgatcagat ggcgctgggc gcaatgcgcg  4140
ccattaccga gtccgggctg cgcgttggtg cggatatctc ggtagtggga tacgacgata  4200
ccgaagacag ctcatgttat atcccgccgt caaccaccat caaacaggat tttcgcctgc  4260
tggggcaaac cagcgtggac cgcttgctgc aactctctca gggccaggcg gtgaagggca  4320
atcagctgtt gcccgtctca ctggtgaaaa gaaaaaccac cctggcgccc aatacgcaaa  4380
ccgcctctcc ccgcgcgttg gccgattcat taatgcagct ggcacgacag gtttcccgac  4440
tggaaagcgg gcagtgagcg caacgcaatt aatgtgagtt agctcactca ttaggcaccc  4500
caggctttac actttatgct tccggctcgt atgttgtgtg gaattgtgag cggataacaa  4560
tttcacacag gaaacagcta tgaccatgat tacggattca ctggccgtcg ttttacaacg  4620
tcgtgactgg gaaaaccctg gcgttaccca acttaatcgc cttgcagcac atccccctttt  4680
cgccagctgg cgtaatagcg aagaggcccg caccgatcgc ccttcccaac agttgcgcag  4740
cctgaatggc gaatggcgct ttgcctggtt tccggcacca agacggtgc cggaaagctg  4800
gctggagtgc gatcttcctg aggccgatac tgtcgtcgtc ccctcaaact ggcagatgca  4860
cggttacgat gcgcccatct acaccaacgt aacctatccc attacggtca atccgccgtt  4920
tgttcccacg gagaatccga cgggttgtta ctcgctcaca tttaatgttg atgaaagctg  4980
gctacaggaa ggccagacgc gaattatttt tgatggcgtt ggaatt        5026
```

METHODS OF IDENTIFYING LRRK2 INHIBITORS

CROSS REFERENCE TO RELATED APPLICATIONS

The present application is a continuation-in-part of U.S. patent application Ser. No. 12/244,715, filed Oct. 2, 2008, now U.S. Pat. No. 7,947,468, International Patent Application number PCT/GB2009/002047, filed Aug. 24, 2009 and European Patent Application number 09252042.8, filed Aug. 24, 2009, which in turn are continuations-in-part of PCT/GB2008/001211 filed Apr. 7, 2008 which in turn claims priority to U.S. Provisional Patent Application No. 60/910,242 filed Apr. 5, 2007 and Great Britain Patent Application number 0706709.3 filed Apr. 5, 2007, the entire contents of all of which are incorporated by reference herein.

FIELD OF THE INVENTION

Disclosed herein are methods, compositions and assays related to the gene encoding for Leucine Rich Repeat protein Kinase-2 (LRRK2).

BACKGROUND OF THE INVENTION

There has been much interest raised by the recent discovery that different autosomal dominant point mutations within the gene encoding for the Leucine Rich Repeat protein Kinase-2 (LRRK2), predispose humans to develop late-onset Parkinson's disease (PD, OMIM accession number 609007), with a clinical appearance indistinguishable from idiopathic PD. The genetic analysis undertaken to date indicates that mutations in LRRK2 are relatively frequent, not only accounting for 5-10% of familial PD, but are also found in a significant proportion of sporadic PD cases. Little is known about how LRRK2 is regulated in cells, what are its physiological substrates and how mutations in LRRK2 cause or increase risk of PD. In mammals there are two isoforms of the LRRK protein kinase, LRRK1 (2038 residues) and LRRK2 (2527 residues). They belong to a protein family that has also been termed Roco. Thus far mutations in LRRK2, but not LRRK1 have been linked to PD.

The LRRK/Roco class of protein kinases was initially characterised in the slime mould *Dictyostelium discoideum*, as a protein termed GbpC (cGMP binding protein C), that comprised an unusual member of the Ras/GTPase superfamily, distinct from other small GTPase domains as it possesses other domains including a protein kinase. Subsequent studies suggested that GbpC regulates chemotaxis and cell polarity in *Dictyostelium*, but the physiological substrates for this enzyme have not been elucidated. The defining feature of the LRRK/Roco-proteins is that they possess Leucine Rich Repeat (LRR) motif, a Ras-like small GTPase, a region of high amino acid conservation that has been termed the C-terminal Of Ras of complex (COR) domain, and a protein kinase catalytic domain. The protein kinase domain of LRRK2 belongs to the tyrosine-like serine/threonine protein kinases and is most similar to the Rho-Interacting Protein kinases (RIPK), that play key roles in innate immunity signalling pathways. Other domains are also found on specific members of the LRRK kinases. For example, the GbpC possesses an additional DEP, cyclicGMP-binding and Ras-GEF domains that are not found in mammalian LRRK1 and LRRK2. Human LRRK1 possesses 3 ankyrin repeats at its N-terminus, whereas LRRK2 lacks these domains, but possesses a WD40 repeat located towards its C-terminus not found in LRRK1.

Human LRRK2 consists of leucine rich repeats (residues 1010-1287), a small GTPase domain (residues 1335-1504), a COR domain (residues 1517-1843), a serine/threonine protein kinase domain (residues 1875-2132) and a motif that has low resemblance to a WD40 repeat (2231-2276). To date approximately 20 single amino acid substitution mutations have been linked to autosomal-dominant PD, and these have been found within or in close proximity to conserved residues of the small GTPase, COR, protein kinase and WD40 domains.

The most prevalent mutant form of LRRK2 accounting for approximately 6% of familial PD and 3% of sporadic PD cases in Europe, comprises an amino acid substitution of Gly2019 located within the conserved DYG-Mg2+-binding motif, in subdomain-VII of the kinase domain, to a Ser residue. Recent reports suggest that this mutation moderately enhances, approximately 2-3-fold, the autophosphorylation of LRRK2, as well as its ability to phosphorylate myelin basic protein. These findings suggest that over-activation of LRRK2 predisposes humans to develop PD, implying that drugs which inhibited LRRK2, could be utilised to delay the onset or even treat some forms of PD. The study of LRRK2 has been hampered by the difficulty in expressing active recombinant enzyme and by the lack of a robust quantitative assay.

The listing or discussion of a prior-published document in this specification should not necessarily be taken as an acknowledgement that the document is part of the state of the art or is common general knowledge.

SUMMARY OF THE INVENTION

Compounds, and methods useful for identifying those compounds, are disclosed herein wherein the compounds are useful in the treatment of Parkinson's Disease.

In one embodiment, a method is provided for identifying a compound expected to be useful in inhibiting LRRK2 protein kinase activity, the method comprising the steps of: (1) determining whether a test compound inhibits the protein kinase activity of a LRRK2 polypeptide on a substrate polypeptide and (2) selecting a compound which modulates, for example inhibits, the said LRRK2 polypeptide protein kinase activity, wherein the substrate polypeptide comprises the sequence (W/R)(X)(X)(F/Y/H/T)(Y/W/R)(T)(X)(R/T)(R)(X) (SEQ ID NO:71), where X represents any amino acid.

In another embodiment, the LRRK2 polypeptide is wild type human LRRK2 or a fragment thereof, or a fusion either thereof; wherein optionally the fragment comprises at least residues 1326-2527 of wild type human LRRK2.

In another embodiment, the LRRK2 polypeptide is human LRRK2 having a naturally occurring mutation of wild type human LRRK2; or a fragment thereof; or a fusion either thereof; wherein optionally the naturally occurring mutation of human LRRK2 is a mutation associated with Parkinson's Disease (PD), wherein optionally the mutation, using the numbering of wild type human LRRK2, is G2019S or the mutation, using the numbering of wild type human LRRK2, is R1441C, R1441G, Y1699C, R1914H, I2012T, I2020T, T23561, G2385R, K544E, P755L, R793M, Q930R, S973N, R1067Q, S1096C, I1122V, S1228T, I1371V, R1441H, A1442P, R1514Q, M1869T or G2019S.

In another embodiment, the LRRK2 polypeptide is a GST fusion polypeptide, for example GST-LRRK2[1326-2527, G2019S] and/or wherein the LRRK2 polypeptide is recombinant.

In another embodiment, the substrate polypeptide consists of or comprises the sequence WWKFYTLRRA (SEQ ID NO:67), WWRFYTLRKA (SEQ ID NO:48), RLGWWKFY TLRRARQGNTKQR (SEQ ID NO:49), RLGWWRFY TLRKARQGNTKQR (SEQ ID NO:50) or RLGWWRFY TLRRARQGNTKQR (SEQ ID NO:51) and/or wherein the substrate polypeptide is a GST fusion polypeptide, for example GST-RLGWWRFYTLRRARQGNTKQR.

In another embodiment, the method further comprises the step of assessing whether the compound modulates ERM family polypeptide phosphorylation in a whole cell, tissue or organism; or characteristics of Parkinsonism or Parkinson's Disease in an organism and a compound that modulates the activity or disease characteristics is selected; optionally comprising the step of assessing whether the compound modulates the activity of an ERM family polypeptide in the whole cell, tissue or organism, and a compound that modulates the activity is selected; and optionally comprising the step of synthesising, purifying and/or formulating the selected compound.

In one embodiment, provided herein is a purified preparation or kit of parts comprising: i) a LRRK2 polypeptide or recombinant LRRK2 polynucleotide or antibody as described herein and ii) a substrate polypeptide or a polynucleotide encoding a substrate polypeptide; or a recombinant cell capable of expressing a LRRK2 polypeptide and substrate polypeptide and comprising a recombinant LRRK2 polynucleotide and a recombinant polynucleotide encoding the substrate polypeptide.

In one embodiment, provided herein is a polypeptide comprising the sequence (W/R)(X)(X)(F/Y/H/T)(Y/W/R)(T)(X)(R/T)(R)(X) (SEQ ID NO:71), where X represents any amino acid. In another embodiment, the polypeptide comprises the sequence WWKFYTLRRA (SEQ ID NO:67), WWRFYTLRKA (SEQ ID NO:48), RLGWWKFY TLRRARQGNTKQR (SEQ ID NO:49), RLGWWRFY TLRKARQGNTKQR (SEQ ID NO:50) or RLGWWRFY TLRRARQGNTKQ (SEQ ID NO:51) and/or wherein the polypeptide is a GST fusion polypeptide, for example GST-RLGWWRFYTLRRARQGNTKQR. In another embodiment, a polynucleotide is provided comprising the sequence of one of the polypeptides described herein.

In one embodiment, provided herein is a method for preparing a compound which modulates the activity of a LRRK2 polypeptide, the method comprising 1) performing a method according to claim 1 and 2) synthesising, purifying and/or formulating the selected compound.

In one embodiment, provided herein is a method of preparing an antibody capable of binding to LRRK2 comprising the step of raising the antibody to, or selecting the antibody on the basis of binding to, a polypeptide consisting of residues 100 to 498 (or 500) of LRRK2 or a fragment thereof or a fusion either thereof, other than with an LRRK2-derived sequence. In another embodiment, an antibody prepared by this method is provided.

In one embodiment, a method is provided for identifying a compound expected to be useful in treating or preventing Parkinson's Disease (PD) or Parkinsonism, the method comprising the steps of (1) determining whether a test compound inhibits, the phosphorylation of a substrate polypeptide, and (2) selecting a compound which modulates, for example inhibits, the phosphorylation of the substrate polypeptide, wherein the substrate polypeptide is as defined herein.

BRIEF DESCRIPTION OF THE DRAWINGS

FIG. 3.

FIG. 9. Human ERM family polypeptide sequence alignment.

FIG. 11: Fusion of human LRRK2 residues 100-498 used in raising an antibody useful in binding to and in immunoprecipitating LRRK2.

Extracts of the indicated cell lines were screened for the presence of LRRK2 protein following immunoprecipitation with the indicated antibodies and immunoblotting with the LRRK2 [2498-2514] antibody. (C) anti-LRRK2 [100-500] and control IgG were used in immunoprecipitations of 60 mg Swiss 3T3 lysate. Specific bands corresponding to the predicted molecular weight of LRRK2 were excised and tryptic peptides were identified by mass spectrometry. (D) Endogenous LRRK2 kinase activity from S348C anti-LRRK2 [100-500] immunoprecipitates was measured against the Nictide substrate in Swiss 3T3 and RAW cells following immunoprecipitation. (E) Immunoprecipitates from Swiss-3T3 cell lines were assayed against Nictide substrate in the presence of the indicated concentrations of the indicated inhibitors. Kinase assays of immunecomplexes were carried out in triplicate and are representative of at least two seperate experiments.

Figure 19:
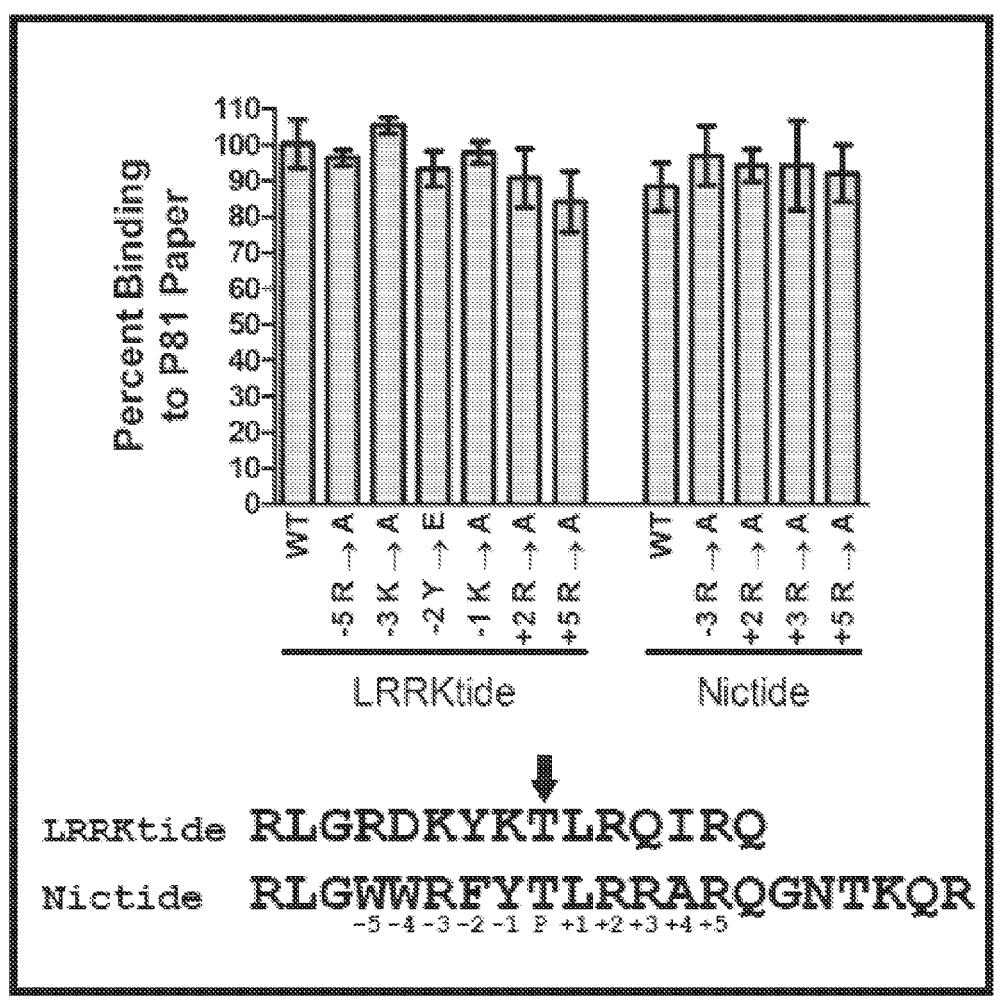

FIG. 19. Assessment of charge-substituted LRRKtide and Nictide peptide binding to P81 paper. The amount of peptide specifically bound to P81 paper was counted in triplicate and the date shows the average percentage±SEM peptide bound to P81 paper for each peptide.

Figure 20:
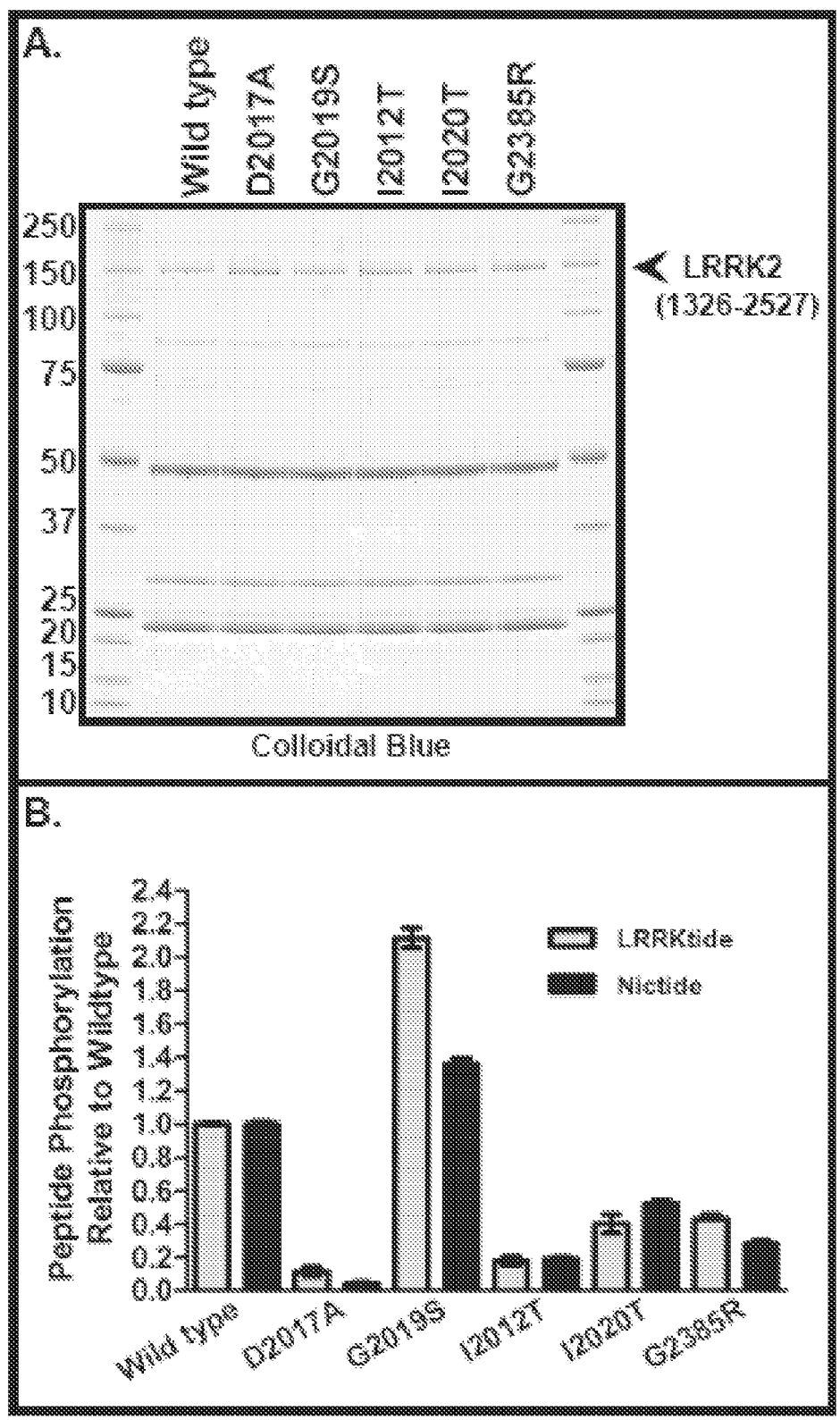

FIG. 20. Analysis of PD-associated mutations on phosphorylation of the novel substrate Nictide. (A) SDS-PAGE gels of wild type and indicated mutations of GST-LRRK2 peptides. (B) Peptide phosphorylation relative to wild type of LRRK2 peptides assayed against LRRKtide and Nictide.

DETAILED DESCRIPTION OF THE INVENTION

A further substrate has been developed for LRRK2, which we have utilised in developing a robust and quantitative assay for LRRK2, useful for, for example, assessing the effect of test compounds on LRRK2 activity.

A first aspect of the invention provides a method for identifying a compound expected to be useful in modulating, for example inhibiting, LRRK2 protein kinase activity, the method comprising the steps of (1) determining whether a test compound modulates, for example inhibits, the protein kinase activity of a LRRK2 polypeptide on a substrate polypeptide and (2) selecting a compound which modulates, for example inhibits, the said LRRK2 polypeptide protein kinase activity, wherein the substrate polypeptide comprises the sequence (W/F/R/K)(W/F/R/K)(R/K)(F/W/H/R)(Y/W/R)(S/T)(L/V/I)(R/K)(R/K)(A/Y) (SEQ ID NO:52) or (W/R)(X)(X̄)(F/Y/H/T)(Y/W/R)(T)(X)(R/T)(R)(X) (SEQ ID NO:71), where X represents any amino acid.

As an alternative to the sequence (W/F/R/K)(W/F/R/K)(R/K)(F/W/H/R) (Y/W/R)(S/T)(L/V/I)(R/K)(R/K)(A/Y) (SEQ ID NO:52 (or (W/R)(X)(X̄)(F/Y/H/T)(Y/W/R)(T) (X)(R/T)(R)(X); SEQ ID NO:71), in all aspects of the invention, the substrate polypeptide may comprise the sequence (W/F/R/K)(W/F/R/K)(R/K)(F/W/H/R)(Y/W/R)(S/T)(L/V/I)(R/K)(R/K)(A/Y) with one, two or three conservative or non-conservative substitutions of residues other than the underlined T/S residue. Thus, up to three residues may differ from the indicated sequences in all aspects of the invention.

As used herein, the designation of an amino acid residue in the instant peptides as more than one amino acid (using the common one-letter amino acid code) in parenthesis with a slash between the amino acids, mean that any of the indicated amino acids, or mimetics thereof (unless specifically excluded), could occupy that residue. For example, (I/L/V)(T/S/A/V/C) means that the first residue can be any one of isoleucine, leucine, or valine, and the second residue can be any one of threonine, serine, alanine, valine, or cysteine, or mimetics.

The underlined residue is the residue that is considered to be phosphorylated by LRRK2. It is preferred that this residue is a threonine residue. Preferences for the other residues (numbered relative to the phosphorylated T/S residue) are as follows:
−5: W or R, −4: W, F, R, K or I; −3: R, K or W −2: F, Y, H or T; −1: Y, R, W; +1: L, V, K or I; +2: R, K or T; +3: R. It is preferred that none of positions −5, −4, −3, −2, −1, 0, +1, +2, +3 or +4 are D or E. It is preferred that position −2 is not R. It is preferred that position −5 is not A.

The protein kinase activity of the LRRK2 polypeptide that is modulated/assessed in the screening method is phosphorylation of a substrate polypeptide as defined above. Phosphorylation of the substrate polypeptide may be assessed by techniques including those discussed further below and in the Examples. For example, antibodies specific for a phosphorylated (or unphosphorylated) phosphorylation site of the substrate polypeptide may be used in assessing phosphorylation of that phosphorylation site, as well known to those skilled in the art. Further methods will be apparent to the skilled person on the basis of this teaching and the many known methods of assessing protein phosphorylation.

Substrate polypeptide phosphorylation may be assessed in vitro or in a cell, for example by assessing phosphorylation of the substrate polypeptide following immunoprecipitation of the substrate polypeptide from the cellular material, for example following incubation of the cell with $^{32}$P- or $^{33}$P-γ-labelled ATP.

A further aspect of the invention provides a method for identifying a compound expected to be useful in modulating, for example inhibiting, the phosphorylation of an ERM family polypeptide in a cell, the method comprising the steps of (1) determining whether a test compound modulates, for example inhibits, the protein kinase activity of a LRRK2 polypeptide on a substrate polypeptide and (2) selecting a compound which modulates, for example inhibits, the said LRRK2 polypeptide protein kinase activity, wherein the substrate polypeptide comprises the sequence (W/F/R/K)(W/F/R/K)(R/K)(F/W/H/R)(Y/W/R)(S/T)(L/V/I)(R/K)(R/K)(A/Y) (SEQ ID NO:52) (or (W/R)(X)(X̄)(F/Y/H/T)(Y/W/R)(T)(X)(R/T)(R)(X); SEQ ID NO:71) (or, as explained above, is otherwise as defined in relation to the first aspect of the invention).

A further aspect of the invention provides a method for identifying a compound expected to be useful in treating or preventing Parkinson's Disease (PD) or Parkinsonism (or other neurodegenerative condition), the method comprising the steps of (1) determining whether a test compound modulates, for example inhibits, the phosphorylation of a substrate polypeptide, and (2) selecting a compound which modulates, for example inhibits, the phosphorylation of the substrate polypeptide, wherein the substrate polypeptide comprises the sequence (W/F/R/K)(W/F/R/K)(R/K)(F/W/H/R)(Y/W/R)(S/T)(L/V/I)(R/K)(R/K)(A/Y) (SEQ ID NO:52) (or (W/R)(X)(X̄)(F/Y/H/T)(Y/W/R)(T)(X)(R/T)(R)(X); SEQ ID NO:71). The method may comprise the steps of (1) determining whether a test compound modulates, for example inhibits, the phosphorylation of the said substrate polypeptide by an LRRK2 polypeptide, and (2) selecting a compound which modulates, for example inhibits, the phosphorylation of the substrate polypeptide by the LRRK2 polypeptide. Examples of methods for assessing the phosphorylation of the substrate polypeptide are discussed above and in the Examples and include methods making use of phosphorylation-specific antibodies, as discussed above.

The activity of the LRRK2 polypeptide may be measured by measuring the phosphorylation by the LRRK2 polypeptide, in the presence of a suitable phosphate donor, of a substrate polypeptide, as discussed above. Examples of methods of assessing the phosphorylation of the substrate polypeptide are indicated above.

The protein kinase activity may be increased or reduced by an alteration in the $V_{max}$ or the $K_m$ (or both) of the LRRK2 polypeptide for a particular substrate. For example, activity may be increased by an increased $V_{max}$ or decreased $K_m$. It will be appreciated that it may not be necessary to determine the value of either $V_{max}$ or $K_m$ in order to determine whether the LRRK2 polypeptide has been activated or deactivated.

Activity may be measured as the amount of a substrate phosphorylated in a given time; a change of activity may therefore be detected as a change in the amount of substrate (for example, at a single concentration) that is phosphorylated in a given time. It is preferred that the activity is increased or decreased, as appropriate, by at least 2, preferably 5, 10, 15, 20, 25, 30 or 50-fold.

It will be appreciated that it may be necessary to determine the effect of the compound on the properties of the substrate, for example by measuring the properties of the substrate when exposed to the compound (1) after exposure of the substrate to the LRRK2 polypeptide, (2) before exposure of the substrate to the LRRK2 polypeptide and/or (3) without exposure to the LRRK2 polypeptide.

By modulation of the protein kinase activity is included inhibition or an increase in the protein kinase activity.

It will be appreciated that in the methods of the invention wherein phosphorylation of a polypeptide may occur that the presence of a suitable phosphate donor may be required, as described for the above aspect of the invention. Suitable phosphate donors will be known to those skilled in the art and include ATP, for example as the magnesium salt (MgATP), as described in the Examples.

It may be useful to assess the effect of the test compound on the binding of the LRRK2 polypeptide and the substrate polypeptide. Methods of assessing polypeptide:polypeptide interactions will be well known to those skilled in the art.

The LRRK2 polypeptide may, for example, be purified from cells in which the LRRK2 polypeptide is expressed naturally, but it may be more convenient for the LRRK2 polypeptide to be recombinant. As described further below and in the Examples, an LRRK2 fragment has been identified that is useful in raising or selecting an antibody that is useful in, for example, preparing LRRK2 that retains protein kinase activity from cells in which the LRRk2 polypeptide is expressed naturally. Thus, the LRRK2 polypeptide may be an LRRK2 polypeptide prepared using such an antibody.

The term ERM family polypeptide will be well known to those skilled in the art. ERM family members include moesin, ezrin and radixin. Merlin is another ERM family member. ERM family members are considered to be substrates of LRRK2, as discussed in Jaleel et al (Biochem. J. 405:207-317, 2007) and in PCT/GB2008/001211, filed on 7 Apr. 2008 (published as WO 2008/122789).

Examples of Accession numbers for ERM family polypeptides in the NCBI database include:
AAB02864, M86450 (pig moesin)
AAA39728, M86390.1, NP_034963, NM_010833.2 (house mouse moesin)
NP_002435, NM_002444.2 (human moesin)
NP_110490, NM_030863.1 (Norway rat moesin)
NP_001039942, NM_001046477.1 (bovine moesin)
NP_062230, NM_019357.1 (Norway rat ezrin)
CAA43086, X60671.1 (house mouse ezrin)
P15311 (human ezrin)
NP_002897, NM_002906.3 (human radixin)
NP_033067, NM_009041 (house mouse radixin)
NP_001005889, NM_001005889.2 (Norway rat radixin)
NP_001009576, NM_001009576.1 (pig radixin)
P35240 (human merlin)
P46662 (house mouse merlin)
Q63648 (Norway rat merlin)

Numerous further examples of mammalian and non-mammalian ERM family polypeptide sequences can be accessed in the sequence databases accessible from the NCBI MEDLINE™ service, as will be well known to the person skilled in the art.

The substrate polypeptide used in the assay may typically be recombinant or chemically synthesised. The substrate polypeptide may be, for example, a bacterially-expressed or mammalian cell-expressed substrate polypeptide (for example as described in the Examples). The substrate polypeptide may be or comprise a fusion polypeptide (for example as described in Example 1) that retains the ability to be phosphorylated by a LRRK2 polypeptide, for example by LRRK2[1326-2527] or LRRK2[1326-2527, G2019S], for example as described in the Examples. The fusion may typically be with a tag, for example a GST tag, as will be well known to those skilled in the art. Alternatively or in addition, it may be with all or part of an ERM polypeptide. In an example the wild-type phosphorylation site of the ERM polypeptide may be replaced by the substrate polypeptide sequence of the invention.

As indicated above, the substrate polypeptide comprises the sequence (W/F/R/K)(W/F/R/K)(R/K)(F/W/H/R)(Y/W/R)(S/T)(L/V/I)(R/K)(R/K)(A/Y) (SEQ ID NO:52) (optionally with up to three substitutions, as discussed above) or (W/R)(X)(X)(F/Y/H/T) (Y/W/R)(T)(X)(R/T)(R)(X) (SEQ ID NO:71). For example, the substrate polypeptide may comprise the sequence WWRFYTLRRA (SEQ ID NO:65). Alternatively, the substrate polypeptide may comprise the sequence WWKFYTLRRA (SEQ ID NO:67) or WWRFYTLRKA (SEQ ID NO:48). An example of a suitable substrate polypeptide is RLGWWRFYTLRRARQGNTKQR (SEQ ID NO:51). The residue phosphorylated by LRRK2 is underlined. This substrate polypeptide is termed "Nictide" in the Examples and Figures. The following are further examples of suitable substrate peptides: RLGWWKFYTLRRARQGNTKQR (SEQ ID NO:49) and RLGWWRFYTLRKARQGNTKQR (SEQ ID NO:50). FIGS. 2, 3, 12, 13 and 14 also indicate peptide sequences that are considered to be compatible with the ability of the peptide to act as a substrate for LRRK2, reflected in the consensus sequence.

As noted above, the substrate polypeptide may comprise a tag sequence, as will be well known to those skilled in the art, for example a Glutathione S-Transferase (GST) or a Myc tag. Thus, a further example of a suitable substrate polypeptide is a fusion of RLGWWRFYTLRRARQGNTKQR (SEQ ID NO:51) and a tag sequence, for example a GST tag, for example as described in the Examples.

The substrate polypeptide can be a polypeptide of less than 100, 80, 60, 50, 40, 30, 25, 20, 19, 18, 17 or 16 amino acids, comprising the amino acid sequence (W/F/R/K)(W/F/R/K)(R/K)(F/W/H/R)(Y/W/R)(S/T)(L/V/I)(R/K)(R/K)(A/Y) (SEQ ID NO:52) or (W/R)(X)(X)(F/Y/H/T)(Y/W/R)(T)(X)(R/T)(R)(X) (SEQ ID NO:71). The substrate polypeptide sequence may typically comprise one or more amino acid sequences of at least five amino acids in length derived from the sequence of a naturally occurring ERM family polypeptide, for example moesin, radixin or ezrin, for example human moesin, radixin or ezrin, optionally with conservative or non-conservative substitutions of residues (for example of up to 10, 20, 30, 40, 50 or 60% of the residues). The amino acid sequence derived from the sequence of a naturally occurring ERM family polypeptide typically does not include the residue(s) of the ERM family polypeptide that are phosphorylated by LRRK2, for example the residue corresponding to Thr558 (or Thr 526) of moesin.

The substrate polypeptides shown above include a sequence (GNTKQR) that is present in the previously identified substrate sequence RLGRDKYK(T/S)LRQIRQGNTKQR (SEQ ID NO:4) (termed Long-LRRKtide) but not in the previously identified shorter sequence RLGRDKYK(T/S)LRQIRQ (SEQ ID NO:3) (short LRRKtide). Long LRRKtide is considered to allow the use 5-10-fold lower amounts of peptide relative to short LRRKtide. The sequence GNTKQR is a sequence found in moesin, ezrin, or radixin.

It may be necessary to denature the substrate polypeptide (for example if it comprises both a FERM domain (for example residues 1 to 298 of human moesin) and the C-terminal tail region (C-ERMAD domain, for example residues 489 to 575 of human moesin)) in order for it to be phosphorylated in vitro by an LRRK2 polypeptide, as discussed in Jaleel et al. and in PCT/GB2008/001211. Accordingly, it may be desirable for the substrate polypeptide not to comprise a functional FERM domain.

The term LRRK2 will be well known to those skilled in the art, as indicated above. The LRRK2 polypeptide used in the assay may be recombinant or non-recombinant. The LRRK2 polypeptide may, for example, be a recombinant or non-recombinant polypeptide prepared using an antibody to LRRK2 that allows the LRRK2 to retain protein kinase activity, for example an antibody raised or selected using a fragment of LRRK2 as discussed further below. The LRRK2 polypeptide may be, for example, a bacterially-expressed or mammalian cell-expressed LRRK2 polypeptide (for example as described in the Examples, in Jaleel et al. or in PCT/GB2008/001211). It may be appropriate to express the LRRK2 polypeptide alongside the substrate polypeptide. It may be useful for the substrate polypeptide to comprise a further portion that is considered to bind or co-localise with LRRK2, for example all or part of an ERM family polypeptide (as discussed above) or all or part of LRP130. The LRRK2 polypeptide may have the amino acid sequence of a naturally occurring LRRK2, or may be or comprise a fusion polypeptide (for example as described in the Examples, or may be a fragment or variant of a naturally occurring LRRK2 that retains the ability to phosphorylate the substrate polypeptide as defined herein, for example the substrate polypeptide termed Nictide, described above, or an ERM family polypeptide or myelin basic protein, for example that retains the ability to phosphorylate denatured moesin or a fragment thereof on the residue corresponding to Thr558 (or Thr 526) of full length human moesin. Thus, the LRRK2 polypeptide is an LRRK2 polypeptide that retains an active kinase domain. It is also considered that in order to be catalytically active, the LRRK2 polypeptide retains regions corresponding to the GTPase domain, COR domain, WD40-like motif and C-terminal tail. The LRRK2 polypeptide may not comprise the Leucine Rich Repeat (LRR) motif present in full length LRRK2. The LRRK2 polypeptide may comprise or consist of residues 1326-2527 of wild-type human LRRK2, or a GST fusion of such a fragment, as described in the Examples. A fragment of a LRRK2 which contains the intact kinase domain and other domains indicated above but not other regions of LRRK2 (for example the Leucine Rich Repeat (LRR) motif) may be useful; this region of LRRK2 is sufficient to retain protein kinase activity but is shorter than full length LRRK2 and easier to express in an active form. The LRRK2 polypeptide used in the assay is not a kinase-dead mutant such as is described in Jaleel et al. or in PCT/GB2008/001211 (for example LRRK2 in which the residue equivalent to residue D2017 of full length human LRRK2 is mutated, for example to Alanine).

Thus, the LRRK2 polypeptide can be wild type human LRRK2 or a fragment thereof, or a fusion either thereof. The fragment may comprise at least residues 1326-2527 of wild type human LRRK2. It is considered that truncation at the C-terminus may adversely affect the protein kinase activity of the truncated LRRK2 polypeptide, whilst truncation at the N-terminus of the fragment may be better tolerated. Thus, the N-terminus of the truncated LRRK2 polypeptide may alternatively lie after residue 1326, for example between residue 1326 and about residue 1336.

The LRRK2 polypeptide can be human LRRK2 having a naturally occurring mutation of wild type human LRRK2; or a fragment thereof; or a fusion either thereof. The fragment may comprise at least residues 1326-2527 of human LRRK2 having a naturally occurring mutation.

The naturally occurring mutation of human LRRK2 may be a mutation associated with Parkinson's Disease (PD). The mutation, using the numbering of wild type human LRRK2, may be G2019S. This mutation is considered to enhance the protein kinase activity of LRRK2.

Figure 17:
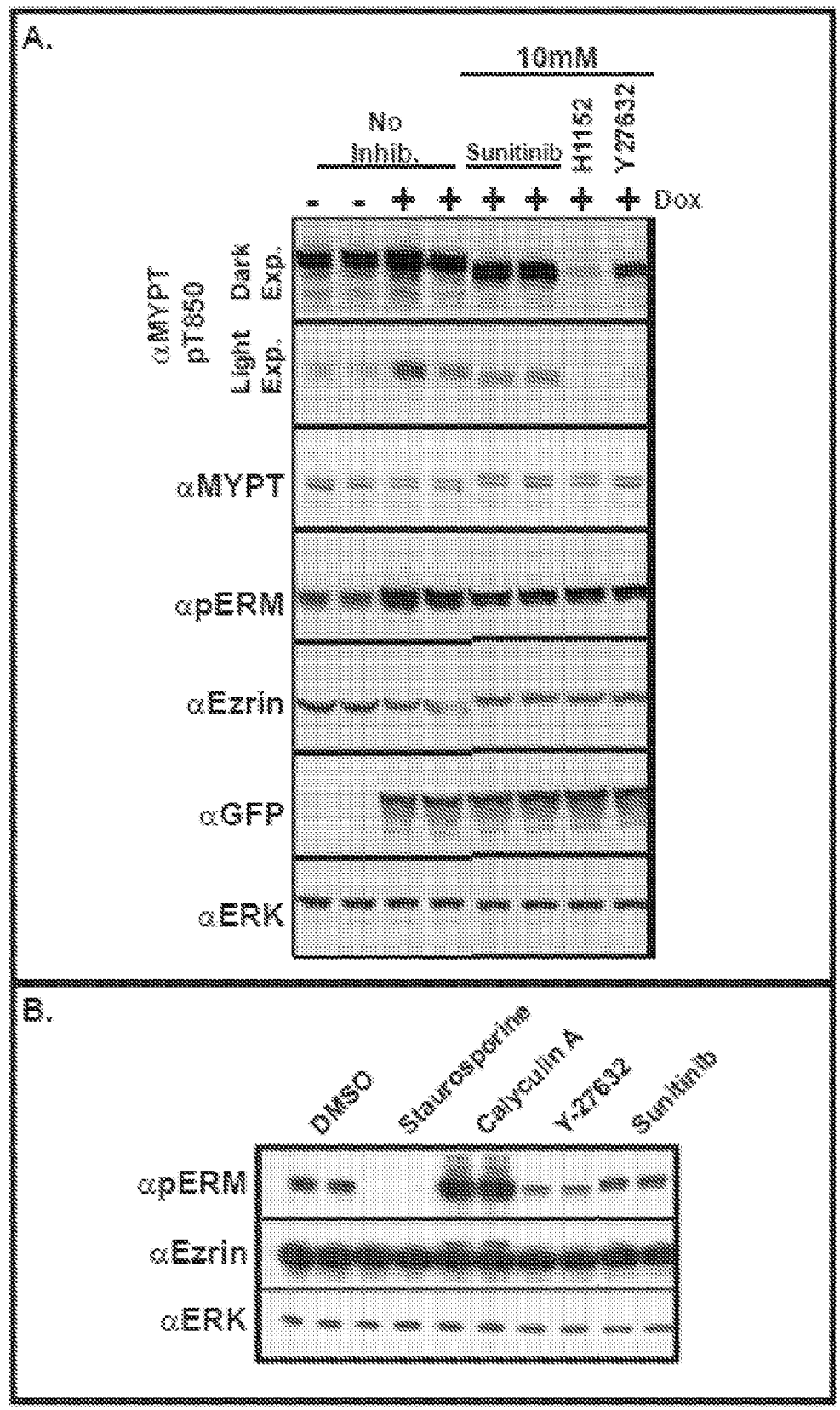
FIG. 17. Testing the efficacy of LRRK2 and ROCK inhibitors in vivo. (A) Flp-in T-REx cells that harbor GFP tagged constitutively active G14V-Rho were either left uninduced or induced by the inclusion of 1 µg/ml doxycycline in the culture medium. At 7 hours post induction, Cells were treated with 10 uM H-1152 and Y-27632 for 1 h. Cells were lysed in direct SDS-Lysis Buffer and resolved on 4-12% Novex gels and subjected to immunoblot analysis with the indicated antibodies. (B) As in (A) except that HEK 293 cells were used.

The mutation, using the numbering of wild type human LRRK2, may alternatively be R1441C, R1441G, Y1699C, R1914H, I2012T, I2020T, or G2385R. LRRK2 with mutations R1441C, R1441G, Y1699C or T23561 is considered to have similar protein kinase activity to wild-type LRRK2. LRRK2 with mutation R1914H or I2012T is considered to be nearly inactive. LRRK2 with mutation I2020T is considered to have activity intermediate between wild-type LRRK2 and LRRK2 with mutation R1914H or I2012T. LRRK2 with mutation G2385R is also considered to be nearly inactive. The activities of further mutants are shown in FIG. 17 of PCT/GB2008/001211, supra.

The LRRK2 polypeptide can be human LRRK2 having the mutation A2016T; or a fragment thereof; or a fusion either thereof. The fragment may comprise at least residues 1326-2527 of human LRRK2 having the A2016T mutation. As discussed in Example 4, this mutant is considered to be resistant to inhibition by compounds such as H-1152, Y-27632 and suntinib.

It may be helpful to test compounds against more than one LRRK2 polypeptide; for example against more than one mutant LRRK2 polypeptide. This may assist in deciding on further compounds to design and test.

The LRRK2 polypeptide may be a GST fusion polypeptide, as discussed in Example 1 and in Jaleel et al or in PCT/GB2008/001211. For example, the LRRK2 polypeptide may be GST-LRRK2[1326-2527, G2019S]. Alternative fusion moieties may also be used, as will be well known to those skilled in the art.

It is particularly preferred, although not essential, that the LRRK2 polypeptide has at least 30% of the enzyme activity of full-length human LRRK2 with respect to the phosphorylation of full-length human moesin on residue Thr558 or Thr526; or the phosphorylation of a peptide substrate encompassing such a residue (for example as discussed above; for example RLGRDKYKTLRQIRQ (SEQ ID NO:1) or RLGRDKYKTLRQIRQGNTKQR (SEQ ID NO:2)); or of the substrate polypeptide, as defined above, for example RLGWWRFYTLRRARQGNTKQR (SEQ ID NO:51). It is more preferred if the LRRK2 polypeptide has at least 50%, preferably at least 70% and more preferably at least 90% of the enzyme activity of full-length human LRRK2 with respect to the phosphorylation of full-length human moesin on residue Thr558 or Thr526; or the phosphorylation of a peptide substrate encompassing such a residue, as discussed above; or of the substrate polypeptide of the invention as defined above, for example RLGWWRFYTLRRARQGNT-KQR (SEQ ID NO:51).

Accession numbers for mammalian LRRK2 sequences in the NCBI database include:
AAV63975.1 human
XP_001168494.1 *Pan troglodytes*, (chimpanzee)
XP_615760.3 *Bos Taurus* (domestic cow)
XP_543734.2 *Canis familiaris* (dog)
NP_080006.2 *Mus musculus* (mouse)
XP_235581.4 *Rattus norvegicus* (rat)

Numerous further examples of mammalian and non-mammalian LRRK2 polypeptide sequences can be accessed in the sequence databases accessible from the NCBI MEDLINE™ service, as will be well known to the person skilled in the art.

By "variants" of a polypeptide we include insertions, deletions and substitutions, either conservative or non-conservative. In particular we include variants of the polypeptide where such changes do not substantially alter the protein kinase activity or ability to be phosphorylated, as appropriate. The skilled person will readily be able to design and test appropriate variants, based on, for example, comparison of sequences of examples of each polypeptide, for example from different species. The skilled person will readily be able to determine where insertions or deletions can be made; or which residues can appropriately be left unchanged; replaced by a conservative substitution; or replaced by a non-conservative substitution. The variant polypeptides can readily be tested, for example as described in the Examples.

By "conservative substitutions" is intended combinations such as Gly, Ala; Val, Ile, Leu; Asp, Glu; Asn, Gln; Ser, Thr; Lys, Arg; and Phe, Tyr.

The three-letter or one letter amino acid code of the IUPAC-IUB Biochemical Nomenclature Commission is used herein, with the exception of the symbol Zaa, defined above. In particular, Xaa represents any amino acid. It is preferred that at least the amino acids corresponding to the consensus sequences defined herein are L-amino acids.

It is particularly preferred if the polypeptide variant has an amino acid sequence which has at least 65% identity with the amino acid sequence of the relevant human polypeptide, more preferably at least 70%, 71%, 72%, 73% or 74%, still more preferably at least 75%, yet still more preferably at least 80%, in further preference at least 85%, in still further preference at least 90% and most preferably at least 95% or 97% identity with the amino acid sequence of the relevant human polypeptide.

It is still further preferred if a protein kinase variant has an amino acid sequence which has at least 65% identity with the amino acid sequence of the catalytic domain of the human polypeptide, more preferably at least 70%, 71%, 72%, 73% or 74%, still more preferably at least 75%, yet still more preferably at least 80%, in further preference at least 83 or 85%, in still further preference at least 90% and most preferably at least 95% or 97% identity with the relevant human amino acid sequence.

It will be appreciated that the catalytic domain of a protein kinase-related polypeptide may be readily identified by a person skilled in the art, for example using sequence comparisons as described below. Protein kinases show a conserved catalytic core, as reviewed in Johnson et al (1996) *Cell*, 85, 149-158 and Taylor & Radzio-Andzelm (1994) *Structure* 2, 345-355. This core folds into a small N-terminal lobe largely comprising anti-parallel β-sheet, and a large C-terminal lobe which is mostly α-helical.

The percent sequence identity between two polypeptides may be determined using suitable computer programs, for example the GAP program of the University of Wisconsin Genetic Computing Group and it will be appreciated that percent identity is calculated in relation to polypeptides whose sequence has been aligned optimally.

The alignment may alternatively be carried out using the Clustal W program (Thompson et al., 1994). The parameters used may be as follows:

Fast pairwise alignment parameters: K-tuple(word) size; 1, window size; 5, gap penalty; 3, number of top diagonals; 5. Scoring method: x percent.

Multiple alignment parameters: gap open penalty; 10, gap extension penalty; 0.05.

Scoring matrix: BLOSUM.

The alignment may alternatively be carried out using the program T-Coffee [19], or EMBOSS [20], as discussed in Example 1.

The residue corresponding (equivalent) to, for example, Thr 558 of full-length human moesin may be identified by alignment of the sequence of the polypeptide with that of full-length human moesin in such a way as to maximise the match between the sequences. The alignment may be carried out by visual inspection and/or by the use of suitable computer programs, for example the GAP program of the University of Wisconsin Genetic Computing Group, which will also allow the percent identity of the polypeptides to be calculated. The Align program (Pearson (1994) in: Methods in Molecular Biology, Computer Analysis of Sequence Data, Part II (Griffin, A M and Griffin, H G eds) pp 365-389, Humana Press, Clifton). Thus, residues identified in this manner are also "corresponding residues".

It will be appreciated that in the case of truncated forms of (for example) moesin or in forms where simple replacements of amino acids have occurred it is facile to identify the "corresponding residue".

It is preferred that the polypeptides used in the screen are mammalian, preferably human (or a species useful in agriculture or as a domesticated or companion animal, for example dog, cat, horse, cow), including naturally occurring allelic variants (including splice variants). The polypeptides used in the screen may comprise a GST portion or may be biotinylated or otherwise tagged, for example with a 6His, HA, myc or other epitope tag, as known to those skilled in the art, or as described in the Examples. This may be useful in purifying and/or detecting the polypeptide(s).

The effect of the compound may be determined by comparing the rate or degree of phosphorylation of the substrate polypeptide by the LRRK2 polypeptide in the presence of different concentrations of the compound, for example in the absence and in the presence of the compound, for example at a concentration of about 100 µM, 30 µM, 10 µM, 3 µM, 1 µM, 0.1 µM, 0.01 µM and/or 0.001 µM.

It is considered that a compound identified by a method of the invention modulates the ability of the LRRK2 polypeptide to phosphorylate different substrates, for example moesin, radixin or ezrin or the peptide substrate RLGRDKYKTLR-QIRQ (SEQ ID NO:1) or RLGRDKYKTLRQIRQGNTKQR (SEQ ID NO:2). The extent of modulation may be different for different substrates. Thus, it may be desirable, but not essential, to test the effect of a compound identified by a method of the invention on the ability of the LRRK2 polypeptide to phosphorylate a polypeptide of interest, for example an endogenous polypeptide, for example moesin, radixin or ezrin.

The method is useful in identifying compounds that, for example, modulate, for example inhibit, the protein kinase activity of LRRK2 or the phosphorylation of an ERM family polypeptide by LRRK2. A compound that modulates, for example inhibits, the protein kinase activity of LRRK2 or the phosporylation of an ERM family polypeptide by LRRK2 may be useful in the treatment of Parkinson's Disease (for example idiopathic Parkinson's Disease or late-onset Parkinson's Disease) or Parkinsonism.

A compound that modulates, for example inhibits, the protein kinase activity of LRRK2 or the phosphorylation of an ERM family polypeptide, for example moesin, may also be useful in other neurodegenerative conditions.

The compound may be one which binds to or near a region of contact between a LRRK2 polypeptide and a substrate polypeptide, or may be one which binds to another region and, for example, induces a conformational or allosteric change which stabilises (or destabilises) the complex; or promotes (or inhibits) its formation. The compound may bind to the LRRK2 polypeptide or to the substrate polypeptide so as to increase the LRRK2 polypeptide protein kinase activity by an allosteric effect. This allosteric effect may be an allosteric effect that is involved in the natural regulation of the LRRK2 polypeptide's activity.

The compounds identified in the methods may themselves be useful as a drug or they may represent lead compounds for the design and synthesis of more efficacious compounds.

The compound may be a drug-like compound or lead compound for the development of a drug-like compound for each of the above methods of identifying a compound. It will be appreciated that the said methods may be useful as screening assays in the development of pharmaceutical compounds or drugs, as well known to those skilled in the art.

The term "drug-like compound" is well known to those skilled in the art, and may include the meaning of a compound that has characteristics that may make it suitable for use in medicine, for example as the active ingredient in a medicament. Thus, for example, a drug-like compound may be a molecule that may be synthesised by the techniques of organic chemistry, less preferably by techniques of molecular biology or biochemistry, and is preferably a small molecule, which may be of less than 5000 daltons. A drug-like compound may additionally exhibit features of selective interaction with a particular protein or proteins and be bioavailable and/or able to penetrate cellular membranes, but it will be appreciated that these features are not essential.

The term "lead compound" is similarly well known to those skilled in the art, and may include the meaning that the compound, whilst not itself suitable for use as a drug (for example because it is only weakly potent against its intended target, non-selective in its action, unstable, difficult to synthesise or has poor bioavailability) may provide a starting-point for the design of other compounds that may have more desirable characteristics.

It will be understood that it will be desirable to identify compounds that may modulate the activity of the protein kinase in vivo. Thus it will be understood that reagents and conditions used in the method may be chosen such that the interactions between, for example, the LRRK2 polypeptide and the substrate polypeptide, are substantially the same as between the human LRRK2 and an endogenous human substrate polypeptide, for example human ERM family polypeptide, for example moesin, radixin or ezrin polypeptide. It will be appreciated that the compound may bind to the LRRK2 polypeptide, or may bind to the substrate polypeptide.

The compounds that are tested in the screening methods of the assay or in other assays in which the ability of a compound to modulate the protein kinase activity of a protein kinase, for example an LRRK2 polypeptide, may be measured, may be (but do not have to be) compounds that have been selected and/or designed (including modified) using molecular modelling techniques, for example using computer techniques. The selected or designed compound may be synthesised (if not already synthesised) and tested for its effect on the LRRK2 polypeptide, for example its effect on the protein kinase activity. The compound may be tested in a screening method of the invention.

The compounds that are tested may be compounds that are already considered likely to be able to modulate the activity of a protein kinase; or may be compounds that have not been selected on the basis of being likely to modulate the activity of a protein kinase. Thus, the compounds tested may be compounds forming at least part of a general, unselected compound bank; or may alternatively be compounds forming at least part of a pre-selected compound bank, for example a bank of compounds pre-selected on the basis of being considered likely to modulate the activity of a protein kinase.

It will be appreciated that screening assays which are capable of high throughput operation will be particularly preferred. For example, assays using an antibody binding to the phosphorylated form of the substrate polypeptide but not the unphosphorylated form (or vice versa) may be suitable. Examples may include cell based assays and protein-protein binding assays. A further example is an SPA-based (Scintillation Proximity Assay; Amersham International) system as well known to those skilled in the art. For example, beads comprising scintillant and a substrate polypeptide, for example RLGWWRFYTLRRARQGNTKQR (SEQ ID NO:51) as discussed above may be prepared. The beads may be mixed with a sample comprising $^{32}$P- or $^{33}$P-γ-labelled ATP, a LRRK2 polypeptide and with the test compound. Conveniently this is done in a 96-well format. The plate is then counted using a suitable scintillation counter, using known parameters for $^{32}$P or $^{33}$P SPA assays. Only $^{32}$P or $^{33}$P that is in proximity to the scintillant, i.e. only that bound to the substrate that is bound to the beads, is detected. Variants of such an assay, for example in which the substrate polypeptide is immobilised on the scintillant beads via binding to an antibody or antibody fragment, may also be used. High throughput protein kinase activity assays are well known to those skilled in the art and can be readily adapted in view of the information provided herein on the phosphorylation of the substrate polypeptide of the invention by LRRK2 polypeptides.

The screening method may further comprise the step of assessing whether the compound modulates ERM family polypeptide, for example moesin, phosphorylation (or other parameter, for example actin binding or membrane component binding or cell characteristics, as discussed in Jaleel et al or in PCT/GB2008/001211) in a whole cell, tissue or organism; and selecting a compound that modulates the phosphorylation (or other parameter). The compounds may be tested in whole cells, tissue or organisms that have an LRRK2 mutation linked to Parkinson's Disease, as discussed above; or that otherwise over-express LRRK2. The compounds may be tested, for example, in a neuronal cell line. Thus, the effect of the compound on phosphorylation of an ERM family polypeptide, for example moesin, may be assessed in a neuronal cell line.

As will be apparent to those skilled in the art, it may be desirable to assess what effect the compound has on other protein kinases. For example, it may be desirable to assess the effect of the compound on phosphorylation of substrates of other protein kinases, for example substrates of RockII, in order to distinguish between LRRK2 and ROCK inhibitors. For example, as shown in, for example, FIGS. 20 and 22 of PCT/GB2008/001211, supra or discussed in the legends thereto, the substrate preferences of LRRK2 and Rock-II are different. As an example, LRRK2 does not phosphorylate MYPT, while RockII does phosphorylate MYPT.

The screening method may comprise the step of comparing the effect of the test compound with the effect of a comparator compound. For example, as discussed in the Examples, sunitinib is considered to be a compound that inhibits LRRK2 but not ROCK; and Y-27632 and H-1152 are considered to be dual ROCK and LRRK2 inhibitors. A compound that inhibits LRRK2 but not ROCK may show similar effects to sunitinib.

The screening method may comprise the step of assessing whether the compound modulates the activity of LRRK2, in the whole cell, tissue or organism, and selecting a compound that modulates the activity selected. The method may further comprise the step of comparing the effect of the test compound with a comparator compound in the whole cell, tissue or organism. A compound that inhibits LRRK2 but not ROCK may show similar effects to sunitinib and may show different effects to Y-27632 and H-1152.

Information on PD models, biomarkers and assessment techniques, in/against which it may be appropriate further to test compounds identified using the screening methods described herein, can be found at, for example, the following links, which are representative of information available to those skilled in the art.

www.ninds.nih.gov/about_ninds/plans/
  nihparkinsons_agenda.htm#Models
www.sciencedaily.com/releases/2006/07/
  060729134653.htm (mouse model with mitochondrial disturbance)
www.sciencedaily.com/releases/2004/10/
  041005074846.htm (embryonic stem cell model)
en.wikipedia.org/wiki/Parkinson's disease PD animal models include the 6-hydroxydopamine treated rodent and the MPTP treated primate. Both are based on toxic destruction of dopaminergic brain cells (and some other types), and usually employ young, otherwise healthy animals. Because these models reproduce some key features of Parkinson's disease, they are considered useful to test emerging new therapies.

Compounds may also be subjected to other tests, for example toxicology or metabolism tests, as is well known to those skilled in the art.

The screening method of the invention may comprise the step of synthesising, purifying and/or formulating the selected compound.

The invention also provides a method for preparing a compound which modulates the activity of LRRK2, the method comprising 1) performing an appropriate screening method of the invention 2) synthesising, purifying and/or formulating the selected compound.

The compound may be formulated for pharmaceutical use, for example for use in in vivo trials in animals or humans.

A further aspect of the invention provides a compound identified or identifiable by a screening method of the invention.

A still further aspect of the invention is a compound of the invention for use in medicine. A still further aspect of the invention is a compound of the invention for treating Parkinson's Disease (for example idiopathic Parkinson's Disease or late-onset Parkinson's Disease) or Parkinsonism.

The compound may be administered in any suitable way, usually parenterally, for example intravenously, intraperitoneally, subcutaneous or intramuscular or intravesically, in standard sterile, non-pyrogenic formulations of diluents and carriers. The compound may also be administered topically. The compound may also be administered in a localised manner, for example by injection. The treatment may consist of a single dose or a plurality of doses over a period of time. The compound may be useful in treating patients with or at risk of Parkinson's Disease or Parkinsonism.

Whilst it is possible for a compound of the invention to be administered alone, it is preferable to present it as a pharmaceutical formulation, together with one or more acceptable carriers. The carrier(s) must be "acceptable" in the sense of being compatible with the compound of the invention and not deleterious to the recipients thereof. Typically, the carriers will be water or saline which will be sterile and pyrogen free.

Thus, the invention also provides pharmaceutical compositions comprising the compound identified or identifiable by the screening methods of the invention and a pharmaceutically acceptable carrier.

The composition may also comprise or be administered with a further compound useful in treating Parkinson's Disease or Parkinsonism or other neurodegenerative condition, as appropriate.

Accordingly, the invention provides a pharmaceutical composition comprising a compound identified or identifiable by the screening methods of the invention together with a pharmaceutically acceptable carrier and optionally other therapeutic ingredients.

A further aspect of the invention provides a purified preparation or kit of parts comprising an LRRK2 polypeptide (for example as discussed above) or polynucleotide (ie a polynucleotide encoding an LRRK2 polypeptide) or antibody useful in preparing LRRK2, for example as discussed briefly above and below; and a substrate polypeptide of the invention as defined above (or a polynucleotide encoding a substrate polypeptide of the invention); and optionally a comparator compound such as sunitinib; Y-27632 or H-1152. The preparation or kit may, for example, comprise a recombinant LRRK2 polynucleotide or polypeptide and a recombinant or chemically synthesised substrate polypeptide. The kit may further comprise an ERM family polypeptide or a fragment derivable from an ERM family polypeptide, for example moesin, radixin or ezrin, which encompasses the residue corresponding to Thr558 residue of moesin and at least part of the surrounding sequence which includes this residue, for example at least the 2, 3, 4, 5, 6 or 7 residues C-terminal and N-terminal of this residue; for example the polypeptide RLGRDKYKTLRQIRQ (SEQ ID NO:1) or RLGRDKYK-TLRQIRQGNTKQR (SEQ ID NO:2); or a polypeptide of less than 100, 80, 60, 50, 40, 30, 25, 20, 19, 18, 17 or 16 amino acids, comprising the amino acid sequence RLGRDKYK(T/S)LRQIRQ (SEQ ID NO:3) or RLGRDKYK(T/S)LR-QIRQGNTKQR (SEQ ID NO:4), each with no or up to one, two, three, four, five, six, seven, eight, nine or ten conservative or non-conservative substitutions of residues other than the T/S residue, as discussed above.

The preparation or kit may be useful in an assay of the first, second or third aspect of the invention.

Figure 8:
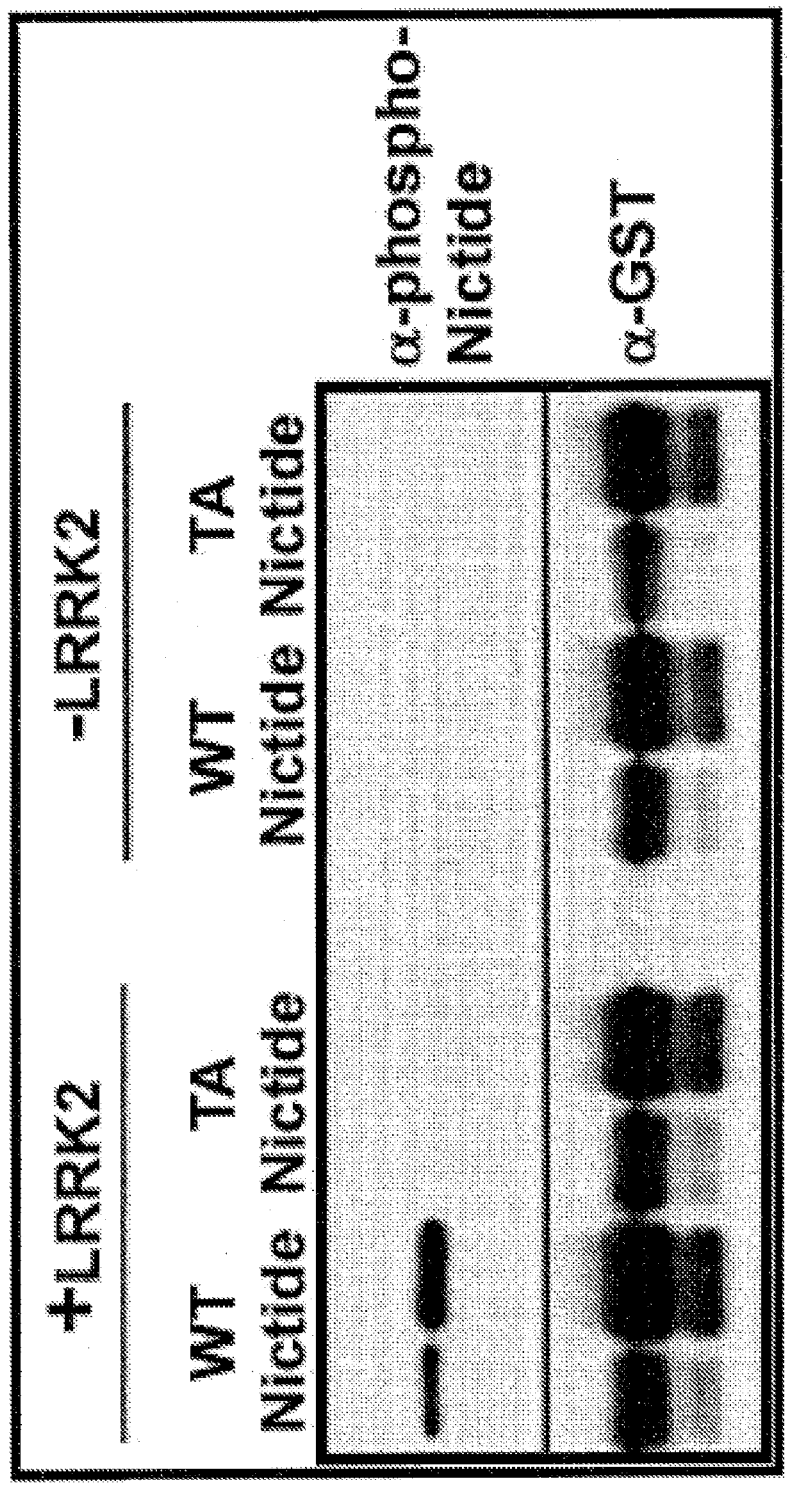
FIG. 8. Phosphorylation of Nictide assessed using an antibody raised against a phospho-Nictide antigen. GST fusion proteins with either the wild-type Nictide sequence or the phosphorylation site mutated to alanine were produced in bacteria (GST-RLGWWRFYTLRRARQGNTKQR (SEQ ID NO:51) or GST-RLGWWRFYALRRA RQGNTKQR (SEQ ID NO:4853 These proteins were subjected to kinase reactions containing LRRK2 (293 cell expressed GST tagged 1326-END G2019S) or buffer. A titration of these reactions containing 66 or 330 ng of the GST fusion was probed with an antibody raised against a phospho-Nictide antigen. Immunoblots were performed in the presence of 10 ug/ml dephospho Nictide.
Figure 10:
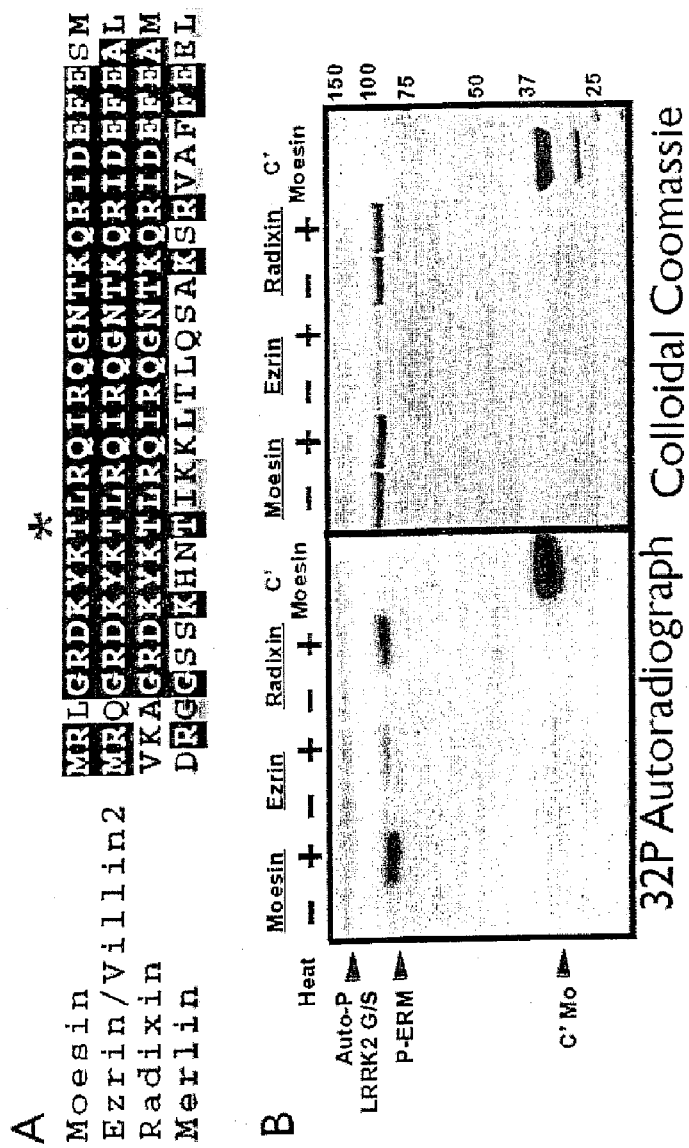
FIG. 10A-10B: Analysis of phosphorylation of moesin by LRRK2 (A) Sequence alignment of the C-terminal regions of Ezrin, Radixin and Merlin. The asterisks indicate the Thr residue equivalent to Thr555 on moesin. Black and grey shaded residues represent identical and homologous residues, respectively.

The kit may further comprise a specific binding partner, typically an antibody, that binds in a phosphorylation state-sensitive manner to an epitope encompassing the phosphorylatable residue of the substrate polypeptide of the invention. By "binding in a phosphorylation state-sensitive manner" is included the meaning that the specific binding partner is capable of binding to the epitope (or substrate polypeptide comprising the epitope) when phosphorylated on the phosphorylatable portion, but is not capable of binding to the epitope (or substrate polypeptide comprising the epitope) when it is not phosphorylated on the phosphorylatable portion of that epitope. Thus, it is preferred that the specific binding partner has at least a 5-fold, preferably 10, 20, 50, 100, 200, 500,1000, 2000 or 5000-fold difference in affinity for the phosphorylated and non-phosphorylated substrate polypeptide. In practice, a specific binding partner prepared and purified/selected using methods known in the art (see, for example, WO 03/087400; for example affinity purified using a phosphorylated peptide affinity column and a nonphosphorylated peptide affinity column) is expected to have the required affinity and specificity of binding. An example of such an antibody prepared using these techniques is described/used in FIG. 8 and the legend thereto.

By the term "antibody" is included synthetic antibodies and fragments and variants (for example as discussed above) of whole antibodies which retain the antigen binding site. The antibody may be a monoclonal antibody, but may also be a polyclonal antibody preparation, a part or parts thereof (for example an $F_{ab}$ fragment or $F(ab')_2$) or a synthetic antibody or part thereof. Fab, Fv, ScFv and dAb antibody fragments can all be expressed in and secreted from E. coli, thus allowing the facile production of large amounts of the said fragments. By "ScFv molecules" is meant molecules wherein the $V_H$ and $V_L$ partner domains are linked via a flexible oligopeptide. IgG class antibodies are preferred.

Suitable monoclonal antibodies to selected antigens may be prepared by known techniques, for example those disclosed in "Monoclonal Antibodies: A manual of techniques", H. Zola (CRC Press, 1988) and in "Monoclonal Hybridoma Antibodies: techniques and Applications", JGR Hurrell (CRC Press, 1982), modified as indicated above. Bispecific antibodies may be prepared by cell fusion, by reassociation of monovalent fragments or by chemical cross-linking of whole antibodies. Methods for preparing bispecific antibodies are disclosed in Corvalen et al, (1987) Cancer Immunol. Immunother. 24, 127-132 and 133-137 and 138-143.

A general review of the techniques involved in the synthesis of antibody fragments which retain their specific binding sites is to be found in Winter & Milstein (1991) Nature 349, 293-299.

By "purifed" is meant that the preparation has been at least partially separated from other components in the presence of which it has been formed, for example other components of a recombinant cell. Examples of methods of purification that may be used are described in the Examples or in Jaleel et al (2007) supra or in PCT/GB2008/001211, supra.

The preparation may be substantially pure. By "substantially pure" we mean that the said polypeptide(s) are substantially free of other proteins. Thus, we include any composition that includes at least 2, 3, 4, 5, 10, 15, 20 or 30% of the protein content by weight as the said polypeptides, preferably at least 50%, more preferably at least 70%, still more preferably at least 90% and most preferably at least 95% of the protein content is the said polypeptides.

Thus, the invention also includes compositions comprising the said polypeptides and a contaminant wherein the contaminant comprises less than 96, 95, 94, 90, 85, 80 or 70% of the composition by weight, preferably less than 50% of the composition, more preferably less than 30% of the composition, still more preferably less than 10% of the composition and most preferably less than 5% of the composition by weight.

The invention also includes the substantially pure said polypeptides when combined with other components ex vivo, said other components not being all of the components found in the cell in which said polypeptides are found.

A further aspect of the invention provides a recombinant cell capable of expressing a LRRK2 polypeptide and a substrate polypeptide according to the invention. The cell may comprise a recombinant LRRK2 polynucleotide and a recombinant substrate polypeptide polynucleotide. The substrate polypeptide may comprise a tag or a further portion considered to bind to or co-localise with LRRK2, for example an ERM family polypeptide or fragment, as discussed above. The cell may be capable of overexpressing the LRRK2 polypeptide from the endogenous sequence encoding the said polypeptide, for example using techniques of sequence-specific targeting of transcription activators. Thus the cell may be modified in a way intended to lead to increased expression of the LRRK2 polypeptide relative to a cell which has not been so modified. The cell may be a prokaryotic or eukaryotic cell. For example it may be a eukaryotic cell, for example an insect, yeast or mammalian cell, for example a human cell.

Examples of suitable cells are described, for example, in the Examples or in Jaleel et al or in PCT/GB2008/001211.

The recombinant nucleic acid is preferably suitable for expressing the encoded polypeptide. The recombinant nucleic acid may be in the form of an expression vector. Recombinant polynucleotides suitable for expressing a given polypeptide are well known to those skilled in the art, and examples are described in the Examples and in Jaleel et al or in PCT/GB2008/001211.

A further aspect of the invention provides a recombinant cell comprising a LRRK2 polypeptide and a substrate polypeptide of the invention. The cell typically comprises a recombinant LRRK2 polypeptide and a recombinant substrate polypeptide. The cell may be a cell according to the preceding aspect of the invention. The cell may comprise at least 1.1, 1.2, 1.5, 2, 3, 5, 10 or 20-fold more LRRK2 polypeptide than an equivalent cell which has not been modified in order to overexpress the LRRK2 polypeptide or to express the recombinant LRRK2 polypeptide.

By "suitable for expressing" is mean that the polynucleotide is a polynucleotide that may be translated to form the polypeptide, for example RNA, or that the polynucleotide (which is preferably DNA) encoding the polypeptide of the invention is inserted into an expression vector, such as a plasmid, in proper orientation and correct reading frame for expression. The polynucleotide may be linked to the appropriate transcriptional and translational regulatory control nucleotide sequences recognised by any desired host; such controls may be incorporated in the expression vector.

Characteristics of vectors suitable for replication in mammalian/eukaryotic cells are well known to those skilled in the art, and examples are given below. It will be appreciated that a vector may be suitable for replication in both prokaryotic and eukaryotic cells.

A variety of methods have been developed to operably link polynucleotides, especially DNA, to vectors for example via complementary cohesive termini. Suitable methods are described in Sambrook et al (1989) Molecular Cloning, A Laboratory Manual, Cold Spring Harbor Laboratory, Cold Spring Harbor, N.Y.

A desirable way to modify the DNA encoding a polypeptide of the invention is to use the polymerase chain reaction as disclosed by Saiki et al (1988) Science 239, 487-491. This method may be used for introducing the DNA into a suitable vector, for example by engineering in suitable restriction sites, or it may be used to modify the DNA in other useful ways as is known in the art.

In this method the DNA to be enzymatically amplified is flanked by two specific primers which themselves become incorporated into the amplified DNA. The said specific primers may contain restriction endonuclease recognition sites which can be used for cloning into expression vectors using methods known in the art.

The DNA (or in the case of retroviral vectors, RNA) is then expressed in a suitable host to produce a polypeptide comprising the compound of the invention. Thus, the DNA encoding the polypeptide constituting the compound of the invention may be used in accordance with known techniques, appropriately modified in view of the teachings contained herein, to construct an expression vector, which is then used to transform an appropriate host cell for the expression and production of the polypeptide of the invention. Such techniques include those disclosed in U.S. Pat. No. 4,440,859 to Rutter et al, U.S. Pat. No. 4,530,901 to Weissman, U.S. Pat. No. 4,582,800 to Crowl, U.S. Pat. No. 4,677,063 to Mark et al, U.S. Pat. No. 4,678,751 to Goeddel, U.S. Pat. No. 4,704,362 to Itakura et al, U.S. Pat. No. 4,710,463 to Murray, U.S. Pat. No. 4,757,006 to Toole, Jr. et al, U.S. Pat. No. 4,766,075 to Goeddel et al and U.S. Pat. No. 4,810,648 to Stalker, all of which are incorporated herein by reference.

The DNA (or in the case of retroviral vectors, RNA) encoding the polypeptide may be joined to a wide variety of other DNA sequences for introduction into an appropriate host. The companion DNA will depend upon the nature of the host, the manner of the introduction of the DNA into the host, and whether episomal maintenance or integration is desired.

Generally, the DNA is inserted into an expression vector, such as a plasmid, in proper orientation and correct reading frame for expression. If necessary, the DNA may be linked to the appropriate transcriptional and translational regulatory control nucleotide sequences recognised by the desired host, although such controls are generally available in the expression vector. The vector is then introduced into the host through standard techniques. Generally, not all of the hosts will be transformed by the vector. Therefore, it will be necessary to select for transformed host cells. One selection technique involves incorporating into the expression vector a DNA sequence, with any necessary control elements, that codes for a selectable trait in the transformed cell, such as antibiotic resistance. Alternatively, the gene for such selectable trait can be on another vector, which is used to co-transform the desired host cell.

Host cells that have been transformed by the recombinant DNA of the invention are then cultured for a sufficient time and under appropriate conditions known to those skilled in the art in view of the teachings disclosed herein to permit the expression of the polypeptide, which can then be recovered.

Many expression systems are known, including bacteria (for example *E. coli* and *Bacillus subtilis*), yeasts (for example *Saccharomyces cerevisiae*), filamentous fungi (for example *Aspergillus*), plant cells, animal cells and insect cells.

The vectors include a prokaryotic replicon, such as the ColE1 ori, for propagation in a prokaryote, even if the vector is to be used for expression in other, non-prokaryotic, cell types. The vectors can also include an appropriate promoter such as a prokaryotic promoter capable of directing the expression (transcription and translation) of the genes in a bacterial host cell, such as *E. coli*, transformed therewith.

A promoter is an expression control element formed by a DNA sequence that permits binding of RNA polymerase and transcription to occur. Promoter sequences compatible with exemplary bacterial hosts are typically provided in plasmid vectors containing convenient restriction sites for insertion of a DNA segment of the present invention.

Typical prokaryotic vector plasmids are pUC18, pUC19, pBR322 and pBR329 available from Biorad Laboratories, (Richmond, Calif.) and pTrc99A and pKK223-3 available from Pharmacia, Piscataway, N.J.

A typical mammalian cell vector plasmid is pSVL available from Pharmacia. This vector uses the SV40 late promoter to drive expression of cloned genes, the highest level of expression being found in T antigen-producing cells, such as COS-1 cells.

An example of an inducible mammalian expression vector is pMSG, also available from Pharmacia. This vector uses the glucocorticoid-inducible promoter of the mouse mammary tumour virus long terminal repeat to drive expression of the cloned gene.

Useful yeast plasmid vectors are pRS403-406 and pRS413-416 and are generally available from Stratagene Cloning Systems, La Jolla, Calif. Plasmids pRS403, pRS404, pRS405 and pRS406 are Yeast Integrating plasmids (YIps) and incorporate the yeast selectable markers HIS3, TRP1, LEU2 and URA3. Plasmids pRS413-416 are Yeast Centromere plasmids (YCps).

The host cell can be either prokaryotic or eukaryotic. Bacterial cells are preferred prokaryotic host cells and typically are a strain of *E. coli* such as, for example, the *E. coli* strains DH5 available from Bethesda Research Laboratories Inc., Bethesda, Md., and RR1 available from the American Type Culture Collection (ATCC) of Rockville, Md., (No ATCC 31343). Preferred eukaryotic host cells include yeast, insect and mammalian cells, preferably vertebrate cells such as those from a mouse, rat, monkey or human fibroblastic cell line. Yeast host cells include YPH499, YPH500 and YPH501 which are generally available from Stratagene Cloning Systems. Preferred mammalian host cells include human embryonic kidney 293 cells (see Example 1), Chinese hamster ovary (CHO) cells available from the ATCC as CCL61, NIH Swiss mouse embryo cells NIH/3T3 available from the ATCC as CRL 1658, and monkey kidney-derived COS-1 cells available from the ATCC as CRL 1650. Preferred insect cells are Sf9 cells which can be transfected with baculovirus expression vectors.

Transformation of appropriate cell hosts with a DNA construct is accomplished by well known methods that typically depend on the type of vector used. With regard to transformation of prokaryotic host cells, see, for example, Cohen et al (1972) *Proc. Natl. Acad. Sci. USA* 69, 2110 and Sambrook et al (1989) *Molecular Cloning, A Laboratory Manual*, Cold Spring Harbor Laboratory, Cold Spring Harbor, N.Y. Transformation of yeast cells is described in Sherman et al (1986) *Methods In Yeast Genetics, A Laboratory Manual*, Cold Spring Harbor, N.Y. The method of Beggs (1978) *Nature* 275, 104-109 is also useful. With regard to vertebrate cells, reagents useful in transfecting such cells, for example calcium phosphate and DEAE-dextran or liposome formulations, are available from Stratagene Cloning Systems, or Life Technologies Inc., Gaithersburg, Md.

Electroporation is also useful for transforming and/or transfecting cells and is well known in the art for transforming yeast cell, bacterial cells, insect cells and vertebrate cells.

For example, many bacterial species may be transformed by the methods described in Luchansky et al (1988) *Mol. Microbiol.* 2, 637-646 incorporated herein by reference. The greatest number of transformants is consistently recovered following electroporation of the DNA-cell mixture suspended in 2.5× PEB using 6250V per cm at 25:FD.

Methods for transformation of yeast by electroporation are disclosed in Becker & Guarente (1990) *Methods Enzymol.* 194, 182.

Successfully transformed cells, ie cells that contain a DNA construct of the present invention, can be identified by well known techniques. For example, cells resulting from the introduction of an expression construct of the present invention can be grown to produce the polypeptide of the invention. Cells can be harvested and lysed and their DNA content examined for the presence of the DNA using a method such as that described by Southern (1975) *J. Mol. Biol.* 98, 503 or Berent et al (1985) *Biotech.* 3, 208.

In addition to directly assaying for the presence of recombinant DNA, successful transformation can be confirmed by well known immunological methods when the recombinant DNA is capable of directing the expression of the protein. For example, cells successfully transformed with an expression vector produce proteins displaying appropriate antigenicity. Samples of cells suspected of being transformed are harvested and assayed for the protein using suitable antibodies.

Thus, in addition to the transformed host cells themselves, the present invention also contemplates a culture of those cells, preferably a monoclonal (clonally homogeneous) culture, or a culture derived from a monoclonal culture, in a nutrient medium.

A further aspect of the invention method for making a preparation of the invention, comprising the step of purifying the preparation from a cell according to the invention. Methods of cultivating host cells and isolating recombinant proteins are well known in the art. Examples of suitable purification techniques are described in the Examples or in Jaleel et al. or in PCT/GB2008/001211. For example, one or more component of the preparation may be tagged so as to aid purification using affinity reagents, as will be well known to those skilled in the art and as described in the Examples. Chromatographic techniques may also be used, for example as described in the Examples.

A further aspect of the invention provides a preparation obtained or obtainable by the method of the preceding aspect of the invention. The preparation may comprise, for example, a tagged LRRK2 polypeptide and a substrate polypeptide of the invention.

The method of the first, second or third aspect of the invention may be performed with the LRRK2 polypeptide and substrate polypeptide in the form of a preparation of the invention; or a preparation or complex obtained or obtainable by the method as indicated above; or in a cell of the invention.

The above polypeptides may be made by methods well known in the art and as described below and in the Examples, for example using molecular biology methods or automated chemical peptide synthesis methods.

It will be appreciated that peptidomimetic compounds may also be useful. Thus, by "polypeptide" or "peptide" we include not only molecules in which amino acid residues are joined by peptide (—CO—NH—) linkages but also molecules in which the peptide bond is reversed. Such retroinverso peptidomimetics may be made using methods known in the art, for example such as those described in Meziere et al (1997) *J. Immunol.* 159, 3230-3237, incorporated herein by reference. This approach involves making pseudopeptides containing changes involving the backbone, and not the orientation of side chains. Meziere et al (1997) show that, at least for MHC class II and T helper cell responses, these pseudopeptides are useful. Retro-inverse peptides, which contain NH—CO bonds instead of CO—NH peptide bonds, are much more resistant to proteolysis.

Similarly, the peptide bond may be dispensed with altogether provided that an appropriate linker moiety which retains the spacing between the CI atoms of the amino acid residues is used; it is particularly preferred if the linker moiety has substantially the same charge distribution and substantially the same planarity as a peptide bond.

It will be appreciated that the peptide may conveniently be blocked at its N- or C-terminus so as to help reduce susceptibility to exoproteolytic digestion.

Thus, it will be appreciated that the LRRK2 or, more preferably, the substrate polypeptide may be a peptidomimetic compound.

A kit of parts of the invention comprising a recombinant polynucleotide encoding a LRRK2 polypeptide and a recombinant polynucleotide encoding the substrate polypeptide may be useful in forming a preparation or complex which may be useful in, for example a screening method of the first, second or third aspect of the invention. The recombinant polynucleotide(s) may be in an expression vector (for example as discussed above) or (less desirably) useful for in vitro expression.

A further aspect of the invention provides a polypeptide comprising the sequence (W/F/R/K)(W/F/R/K)(R/K)(F/W/H/R)(Y/W/R)(S/T)(L/V/I)(R/K)(R/K)(A/Y) (SEQ ID NO:52) or (W/R)(X)(X)(F/Y/H/T)(Y/W/R)(T)(X)(R/T)(R)(X) (SEQ ID NO:71), where X represents any amino acid (or alternatively comprising the sequence (W/F/R/K)(W/F/R/K)(R/K)(F/W/H/R) (Y/W/R)(S/T)(L/V/I)(R/K)(R/K)(A/Y) (SEQ ID NO:52) with one, two or three conservative or non-conservative substitutions of residues other than the T/S residue). Such a polypeptide is considered to be a substrate for LRRK2, as discussed above. Preferences for the substrate polypeptide are as indicated above.

A further aspect of the invention provides a polynucleotide encoding the polypeptide of the invention.

The polynucleotide may be a vector suitable for replication and/or expression of the polypeptide in a mammalian/eukaryotic cell. A still further aspect of the invention is a recombinant polynucleotide suitable for expressing a polypeptide of the invention. Typically the recombinant polynucleotide comprises a polynucleotide encoding the polypeptide of the invention.

The polynucleotide or recombinant polynucleotide may be DNA or RNA, preferably DNA. The polynucleotide may or may not contain introns in the coding sequence; preferably the polynucleotide is or comprises a cDNA.

A further aspect of the invention provides a method of phosphorylating a substrate polypeptide of the invention, wherein the substrate polypeptide is phosphorylated by an LRRK2 polypeptide. The substrate polypeptide that is phosphorylated by the method may be partially or fully dephosphorylated substrate polypeptide.

A further aspect of the invention provides the use of an LRRK2 polypeptide in a method of phosphorylating a substrate polypeptide of the invention. The substrate polypeptide is typically phosphorylated on the underlined threonine or serine residue.

It will be appreciated that if the substrate polypeptide is already phosphorylated, further phosphorylation may not be possible. It will further be appreciated that a substrate polypeptide isolated from cells (for example as a recombinant polypeptide) may be heterogeneous with regard to its phosphorylation state. For example, fully phosphorylated, fully dephosphorylated and/or partially phosphorylated molecules of substrate polypeptides may be present in a single cell or group/culture of cells.

A further aspect of the invention provides a method of characterising an LRKK2 mutant, for example an LRRK2 mutant found in a patient with Parkinson's Disease, the method comprising the step of assessing the ability of the LRRK2 mutant to phosphorylate a substrate polypeptide of the invention. The method may comprise the step of determining the $K_m$ and/or the $V_{max}$ of the LRRK2 mutant for the substrate polypeptide of the invention. Such characterisation may be useful in investigating mechanisms underlying Parkinson's Disease or Parkinsonism.

A further aspect of the invention provides a method for assessing LRRK2 activity in a sample, the method comprising the step of assessing the ability of the sample to phosphorylate a substrate polypeptide of the invention. The method may comprise the step of determining the $K_m$ and/or the $V_{max}$ of the sample for the substrate polypeptide of the invention. The method may comprise the step of assessing the ability of an LRRK2 inhibitor to inhibit the ability of the sample to phosphorylate the substrate polypeptide of the invention. The LRRK2 inhibitor may be, for example, sunitinib or Y-27632 or H-1152. The sample may be, for example, a sample obtained from a patient or may be a sample from a cell culture or a sample taken during an LRRK2 purification protocol, as will be well known to those skilled in the art. The sample may be an immunoprecipitate prepared using an antibody to LRRK2 that allows LRRK2 to retain protein kinase activity, for example as described herein, for example from material obtained from a patient, a cell culture or during a purification protocol.

Examples of methods for assessing the phosphorylation of the substrate polypeptide are discussed above and in the Examples and include methods making use of phosphorylation-specific antibodies, as discussed above.

A further aspect of the invention provides the use of a polypeptide consisting of residues 100 to 498 (or 500) of LRRK2 or a fragment thereof or a fusion either thereof (for example as shown in FIG. 11, for example a fusion with a sequence of less than about 10 amino acids), other than with an LRRK2-derived sequence, in the preparation of an antibody. The antibody typically is able to bind to LRRK2, for example to immunoprecipitate LRRK2 from cellular material, and allows the LRRK2 to retain protein kinase activity. Thus, LRRK2 immunoprecipitated using the antibody typically retains protein kinase activity. As will be apparent to those skilled in the art, in embodiments the polypeptide may be used as an immunogen or may be used in selection or refinement of the antibody. Terminology and examples of methodology relating to antibodies are discussed above. Example 3 below indicates fragments of LRRK2 that were tested as immunogens. Only antibodies raised to LRRK2 (100-500) as shown in FIG. 11 were found to be useful in immunoprecipitating LRRK2 that retained protein kinase activity.

A further aspect of the invention provides a method of preparing an antibody capable of binding to LRRK2 comprising the step of raising the antibody to, or selecting the antibody on the basis of binding to, a polypeptide consisting of residues 100 to 498 (or 500) of LRRK2 or a fragment thereof or a fusion either thereof (for example as shown in FIG. 11 or as discussed above), other than with an LRRK2-derived sequence. It is considered that such an antibody is capable of immunoprecipitating LRRK2; and that the LRRK2 retains protein kinase activity.

A further aspect of the invention provides an antibody obtained or obtainable by the method of the preceding aspect of the invention. A further aspect of the invention provides an antibody binding to a polypeptide consisting of residues 100 to 498 (or 500) of LRRK2 or a fragment thereof or a fusion either thereof (for example as shown in FIG. 11 or as discussed above), other than with an LRRK2-derived sequence.

For these aspects of the invention it may be preferred that the said fragment is not residues 100-190 of LRRK2.

A further aspect of the invention provides the use of an antibody of the invention in a method of preparing, assaying or detecting LRRK2. Examples of such uses are mentioned above and in the Examples.

A further aspect of the invention provides the use of sunitinib; Y-27632 or H-1152 in a method for investigating or identifying a substrate for LRRK2 or ROCK2. As noted above and in the Examples, sunitinib is considered to inhibit LRRK2 but not ROCK2. As set out in the Examples and as will be apparent to the skilled person, phosphorylation of a substrate of LRRK2 should be suppressed by sunitinib, Y-27632 and H-1152; whilst phosphorylation of a substrate of ROCK2 should be suppressed by Y-27632 and H-1152, but not by sunitinib.

A further aspect of the invention provides the use of a human LRRK2 having the mutation A2016T; or a fragment thereof; or a fusion either thereof, in a method for investigating or identifying a substrate for LRRK2. The fragment may comprise at least residues 1326-2527 of human LRRK2 having the A2016T mutation. As discussed in Example 4, this mutant is considered to be resistant to inhibition by compounds such as H-1152, Y-27632 and suntinib: if the wild type and A2016T mutant are overexpressed in parallel cell cultures then the phosphorylation of any target substrate should be less sensitive to inhibition by H-1152, Y-27632 or sunitinib in the cells overexpressing the A2016T mutant.

All documents referred to herein are hereby incorporated by reference. For the avoidance of doubt Jaleel et al (2007) Biochem J 405(2), 307-317 and PCT/GB2008/001211 are hereby incorporated by reference.

The invention is now described in more detail by reference to the following, non-limiting, Figures and Examples.

Table 1. Kinase Profiling of LRRK2 and ROCK Inhibitors.

Results are presented as percentage of kinase activity compared to control incubations in which inhibitor was omitted. Protein kinases were assayed as described at the material and methods section. The results are an average of a triplicate determination±standard deviation. Abbreviations not defined in main text: AMPK, AMP-activated protein kinase BRSK, brain-specific kinase; BTK, Bruton's tyrosine kinase; CaMK1, calmodulin-dependent kinase; CaMKK, CaMK kinase; CDK, cyclin-dependent kinase; CHK, checkpoint kinase; CK1, casein kinase 1; CSK, Cterminal Src kinase; DYRK, dual-specificity tyrosine-phosphorylated and regulated kinase; ERK, mitogen activated protein kinase; EF2K, elongation-factor-2 kinase; EPH, ephrin; FGF-R, fibroblast growth factor receptor; GCK, germinal center kinase; GSK3, glycogen synthase kinase 3; HIPK, homeodomain-interacting protein kinase; HER4, V-erb a erythroblastic leukemia viral oncogene homolog 1; IRAK, Interleukin-1 Receptor-Associated Kinase 4; IGF1R, IGF1 receptor; IKK, inhibitory κB kinase; IR, insulin receptor; IRR, insulin-related receptor; JNK, c-Jun N-terminal kinase; Lck, lymphocyte cell-specific protein tyrosine kinase; MAPKAP-K, MAPK-activated protein kinase; MARK, microtubule-affinity regulating kinase; MELK, maternal embryonic leucine-zipper kinase; MKK1, MAPK kinase-1; MLCK, smooth muscle myosin light-chain kinase; MNK, MAPK-integrating protein kinase; MLK, mixed lineage kinase; MINK, Misshapen-like Kinase; MSK, mitogen- and stress-activated protein kinase; MST, mammalian homologue Ste20-like kinase; NEK, NIMA (never in mitosis in *Aspergillus nidulans*)-related kinase; NUAK1, SNF1 like kinase1; PAK, p21-activated protein kinase; PHK, phosphorylase kinase; PIM, provirus integration site for Moloney murine leukaemia virus; PKA, cAMP-dependent protein kinase; PDK1, 3-phosphoinositide-dependent protein kinase-1; PKB, protein kinase B; PKC, protein kinase C; PKD, protein kinase D; PLK, polo-like kinase; PRAK, p38-regulated activated kinase; PRK, protein kinase C-related kinase; RSK, ribosomal S6 kinase; S6K, p70 ribosomal S6 kinase; SGK1, serum and glucocorticoid kinase 1; SRPK, serine-arginine protein kinase; SYK, spleen tyrosine kinase; TBK1, TANK-binding kinase 1; TTK, tau-tubulin kinase; VEGFR, vascular endothelial growth factor receptor; YES1, Yamaguchi sarcoma viral oncogene homologue 1. n.d., not determined.

|  | HA1100 | HA-1077 | H-1152 | Y27632 | Sunitinib | |
|---|---|---|---|---|---|---|
|  | 10 μM | 10 μM | 1 μM | 10 μM | 0.1 μM | 1 μM |
| LRRK2 wild type | 72 ± 11 | 77 ± 13 | 20 ± 3 | 22 ± 2 | 42 ± 2 | 9 ± 10 |
| LRRK2 G2019S | 26 ± 1 | 67 ± 3 | 13 ± 1 | 11 ± 1 | 14 ± 1 | 3 ± 0 |
| ROCK2 | 7 ± 2 | 3 ± 1 | 3 ± 0 | 4 ± 1 | 92 ± 2 | 67 ± 5 |
| MKKI | 63 ± 3 | 41 ± 2 | 69 ± 15 | 71 ± 17 | 37 ± 2 | 16 ± 1 |
| ERKI | 109 ± 6 | 104 ± 2 | 105 ± 8 | 92 ± 1 | 108 ± 2 | 104 ± 7 |
| ERK2 | 102 ± 8 | 98 ± 2 | 94 ± 4 | 94 ± 2 | 101 ± 1 | 103 ± 10 |
| JNK1 | 105 ± 9 | 115 ± 8 | 96 ± 5 | 106 ± 6 | 123 ± 16 | 104 ± 5 |
| JNK2 | 90 ± 5 | 94 ± 4 | 91 ± 6 | 96 ± 9 | 101 ± 8 | 88 ± 1 |
| p32a MAPK | 98 ± 1 | 108 ± 13 | 109 ± 11 | 103 ± 4 | 111 ± 2 | 103 ± 0 |
| p38b MAPK | 90 ± 6 | 111 ± 2 | 107 ± 2 | 101 ± 10 | 116 ± 0 | 113 ± 4 |
| p38g MAPK | 97 ± 9 | 99 ± 5 | 101 ± 18 | 96 ± 13 | 109 ± 21 | 98 ± 18 |
| p38d MAPK | 100 ± 4 | 77 ± 1 | 93 ± 4 | 86 ± 1 | 110 ± 2 | 107 ± 1 |
| ERK8 | 76 ± 1 | 68 ± 44 | 91 ± 11 | 83 ± 6 | 85 ± 1 | 59 ± 4 |
| RSK1 | 11 ± 15 | 14 ± 5 | 57 ± 1 | 26 ± 3 | 38 ± 53 | 78 ± 9 |
| RSK2 | 41 ± 6 | 31 ± 1 | 76 ± 1 | 42 ± 5 | 60 ± 23 | 41 ± 5 |
| PDK1 | 112 ± 4 | 97 ± 1 | 74 ± 5 | 120 ± 9 | 124 ± 2 | 95 ± 1 |
| PKBa | 27 ± 7 | 27 ± 1 | 64 ± 8 | 56 ± 14 | 87 ± 10 | 73 ± 6 |
| PKBb | 100 ± 3 | 77 ± 11 | 112 ± 9 | 105 ± 1 | 101 ± 4 | 88 ± 2 |
| SGK1 | 55 ± 13 | 69 ± 21 | 92 ± 8 | 50 ± 8 | 79 ± 26 | 26 ± 5 |
| S6K1 | 11 ± 1 | 13 ± 0 | 72 ± 2 | 70 ± 11 | 82 ± 4 | 41 ± 3 |
| PKA | 89 ± 10 | 21 ± 0 | 76 ± 5 | 106 ± 16 | 104 ± 3 | 97 ± 3 |
| PRK2 | 12 ± 0 | 6 ± 0 | 70 ± 69 | 7 ± 3 | 98 ± 3 | 81 ± 17 |
| PKCa | 64 ± 5 | 39 ± 5 | 70 ± 11 | 52 ± 1 | 93 ± 13 | 77 ± 9 |
| PKCz | 94 ± 8 | 66 ± 2 | 86 ± 6 | 69 ± 2 | 110 ± 1 | 94 ± 6 |
| PKD1 | 60 ± 3 | 25 ± 1 | 79 ± 16 | 89 ± 0 | 79 ± 7 | 34 ± 5 |
| MSK1 | 17 ± 0 | 14 ± 1 | 39 ± 4 | 41 ± 8 | 94 ± 12 | 60 ± 8 |
| MNK1 | 76 ± 8 | 20 ± 3 | 50 ± 6 | 20 ± 10 | 99 ± 10 | 83 ± 5 |
| MNK2 | 77 ± 4 | 27 ± 6 | 49 ± 9 | 44 ± 2 | 83 ± 17 | 80 ± 7 |
| MAPKAP-K2 | 96 ± 9 | 91 ± 9 | 93 ± 0 | 85 ± 4 | 91 ± 17 | 95 ± 5 |
| PRAK | 88 ± 16 | 93 ± 12 | 87 ± 17 | 88 ± 14 | 102 ± 1 | 75 ± 15 |
| CAMKKb | 93 ± 3 | 95 ± 5 | 81 ± 6 | 102 ± 8 | 87 ± 12 | 39 ± 6 |
| CAMK1 | 108 ± 14 | 109 ± 4 | 105 ± 2 | 85 ± 22 | 113 ± 19 | 66 ± 2 |
| SmMLCK | 66 ± 3 | 66 ± 6 | 96 ± 5 | 70 ± 1 | 49 ± 2 | 26 ± 3 |
| PHK | 89 ± 4 | 46 ± 6 | 26 ± 2 | 79 ± 1 | 11 ± 1 | 2 ± 0 |
| CHK1 | 87 ± 1 | 103 ± 5 | 89 ± 14 | 96 ± 9 | 76 ± 0 | 33 ± 3 |
| CHK2 | 89 ± 13 | 34 ± 2 | 44 ± 0 | 93 ± 7 | 23 ± 1 | 5 ± 1 |
| GSK3b | 91 ± 11 | 91 ± 5 | 72 ± 28 | 92 ± 3 | 108 ± 3 | 93 ± 11 |
| CDK2-Cyclin A | 98 ± 5 | 82 ± 6 | 74 ± 7 | 72 ± 4 | 98 ± 2 | 87 ± 5 |
| PLK1 | 101 ± 9 | 111 ± 14 | 105 ± 1 | 108 ± 16 | 103 ± 9 | 109 ± 10 |
| Aurora B | 59 ± 1 | 51 ± 1 | 11 ± 2 | 79 ± 1 | 72 ± 5 | 29 ± 4 |
| AMPK | 72 ± 2 | 60 ± 1 | 45 ± 4 | 77 ± 4 | 51 ± 3 | 15 ± 4 |
| MARK3 | 64 ± 2 | 79 ± 2 | 56 ± 3 | 105 ± 5 | 77 ± 4 | 36 ± 4 |
| BRSK2 | 65 ± 3 | 38 ± 2 | 17 ± 4 | 43 ± 4 | 94 ± 0 | 40 ± 6 |
| MELK | 76 ± 2 | 19 ± 1 | 70 ± 4 | 79 ± 2 | 55 ± 6 | 17 ± 1 |
| CK1 | 100 ± 0 | 77 ± 1 | 112 ± 9 | 107 ± 12 | 50 ± 2 | 10 ± 0 |
| CK2 | 84 ± 4 | 81 ± 9 | 84 ± 17 | 85 ± 2 | 91 ± 2 | 72 ± 1 |
| DYRK1A | 96 ± 16 | 102 ± 3 | 96 ± 6 | 96 ± 3 | 103 ± 6 | 83 ± 8 |
| DYRK2 | 89 ± 1 | 80 ± 2 | 84 ± 2 | 92 ± 5 | 92 ± 6 | 76 ± 9 |
| DYRK3 | 99 ± 2 | 39 ± 5 | 94 ± 0 | 100 ± 6 | 104 ± 5 | 84 ± 3 |
| NEK2a | 103 ± 2 | 98 ± 9 | 99 ± 3 | 104 ± 0 | 103 ± 12 | 87 ± 6 |
| NEK6 | 96 ± 8 | 107 ± 28 | 99 ± 16 | 80 ± 18 | 95 ± 26 | 83 ± 15 |
| JKKb | 86 ± 6 | 79 ± 4 | 100 ± 8 | 79 ± 4 | 90 ± 9 | 80 ± 4 |
| PIM1 | 90 ± 14 | 84 ± 14 | 90 ± 5 | 94 ± 12 | 95 ± 5 | 86 ± 14 |
| PIM2 | 104 ± 1 | 111 ± 3 | 91 ± 7 | 102 ± 3 | 111 ± 7 | 104 ± 2 |
| PIM3 | 75 ± 1 | 81 ± 1 | 96 ± 1 | 87 ± 2 | 84 ± 1 | 50 ± 8 |
| SRPKI | 90 ± 12 | 92 ± 10 | 125 ± 1 | 65 ± 35 | 80 ± 0 | 86 ± 4 |
| MST2 | 44 ± 4 | 51 ± 2 | 41 ± 2 | 61 ± 8 | 59 ± 7 | 16 ± 2 |
| EF2K | 103 ± 14 | 120 ± 4 | 99 ± 24 | 81 ± 2 | 97 ± 15 | 106 ± 26 |
| HIPK2 | 109 ± 3 | 127 ± 8 | 100 ± 0 | 104 ± 1 | 79 ± 2 | 30 ± 1 |
| PAK4 | 104 ± 4 | 99 ± 17 | 99 ± 7 | 101 ± 23 | 99 ± 9 | 72 ± 5 |
| PAR5 | 113 ± 7 | 112 ± 16 | 100 ± 1 | 101 ± 11 | 121 ± 4 | 99 ± 3 |
| PAK6 | 103 ± 5 | 110 ± 8 | 103 ± 7 | 96 ± 7 | 115 ± 8 | 102 ± 10 |
| MST4 | 82 ± 2 | 79 ± 8 | 90 ± 7 | 67 ± 7 | 87 ± 5 | 80 ± 6 |
| TBK1 | 98 ± 5 | 110 ± 3 | 98 ± 7 | 69 ± 9 | 106 ± 9 | 54 ± 1 |
| IKKe | 99 ± 2 | 95 ± 8 | 80 ± 4 | 76 ± 8 | 101 ± 1 | 63 ± 3 |
| GCK | 73 ± 7 | 55 ± 4 | 56 ± 1 | 89 ± 4 | 45 ± 2 | 11 ± 1 |
| IRAK4 | 87 ± 4 | 69 ± 7 | 102 ± 7 | 101 ± 8 | 76 ± 19 | 23 ± 4 |
| NUAK1 | 36 ± 11 | 21 ± 2 | 51 ± 10 | 106 ± 1 | 30 ± 1 | 15 ± 3 |
| MLK1 | 75 ± 16 | 56 ± 5 | 82 ± 18 | 90 ± 19 | 74 ± 2 | 40 ± 0 |

-continued

| | HA1100 | HA-1077 | H-1152 | Y27632 | Sunitinib | |
| --- | --- | --- | --- | --- | --- | --- |
| | 10 µM | 10 µM | 1 µM | 10 µM | 0.1 µM | 1 µM |
| MINK1 | 68 ± 21 | 54 ± 6 | 104 ± 5 | 81 ± 0 | 46 ± 1 | 8 ± 0 |
| MLK3 | 45 ± 60 | 72 ± 8 | 85 ± 9 | 110 ± 3 | 72 ± 9 | 26 ± 1 |
| LKB1 | 50 ± 0 | 33 ± 0 | 50 ± 3 | 52 ± 12 | 59 ± 1 | 52 ± 2 |
| HER4 | 97 ± 5 | 129 ± 4 | 107 ± 2 | 69 ± 9 | 126 ± 14 | 103 ± 9 |
| TTK | 82 ± 2 | 73 ± 5 | 93 ± 9 | 73 ± 2 | 99 ± 5 | 72 ± 6 |
| Src | 111 ± 2 | 120 ± 6 | 81 ± 0 | 90 ± 4 | 98 ± 7 | 52 ± 1 |
| Lck | 79 ± 29 | 109 ± 7 | 74 ± 1 | 83 ± 32 | 51 ± 4 | 11 ± 2 |
| CSK | 95 ± 7 | 104 ± 12 | 101 ± 4 | 104 ± 14 | 98 ± 10 | 89 ± 2 |
| FGF-R1 | 83 ± 2 | 65 ± 5 | 35 ± 3 | 95 ± 9 | 77 ± 2 | 29 ± 0 |
| IRR | 89 ± 1 | 86 ± 4 | 88 ± 2 | 91 ± 1 | 90 ± 1 | 77 ± 24 |
| EPH A2 | 95 ± 8 | 94 ± 6 | 49 ± 5 | 106 ± 4 | 104 ± 3 | 91 ± 9 |
| SYK | 112 ± 11 | 104 ± 1 | 104 ± 2 | 94 ± 8 | 107 ± 13 | 94 ± 10 |
| YES1 | 111 ± 4 | 136 ± 6 | 76 ± 8 | 96 ± 5 | 30 ± 3 | 7 ± 1 |
| IGF-1R | 91 ± 9 | 92 ± 1 | 113 ± 2 | 99 ± 5 | 84 ± 1 | 33 ± 6 |
| VEG-FR | 115 ± 1 | 70 ± 4 | 82 ± 20 | 105 ± 4 | 33 ± 0 | 9 ± 0 |
| BTK | 108 ± 20 | 112 ± 21 | 82 ± 9 | 85 ± 17 | 90 ± 1 | 52 ± 12 |
| IR-HIS | 100 ± 4 | 105 ± 1 | 108 ± 6 | 113 ± 1 | 104 ± 7 | 65 ± 5 |
| EPH-B3 | 111 ± 2 | 65 ± 9 | 69 ± 11 | 83 ± 12 | 107 ± 9 | 103 ± 0 |

EXAMPLE 1

General Immunoprecipitation and Kinase Assay Protocol

Methods are described in the Figure Legends.
1) Harvest cells by scraping in lysis buffer (500 µl for a 10 cm dish)
Lysis Buffer
50 mM Tris pH 7.5
1% Triton X-100
1 mM NaV
5 mM sodium pyrophosphate
50 mM NaF
0.27 M Sucrose
1 mM EGTA
1 mM EDTA
Add reducing agent (0.1% β-mercaptoethanol) and inhibitors (1 mM Benzamidine, 1 mM PMSF) before use.
2) Centrifuge lysates 13000 rpm for 25 min at 4° C. and retain supernatant.
3) Perform protein assay.
4) IP from 1-2 mg total protein lysate using 5 µg LRRK2 100-500 antibody coupled to protein G sepharose (10 ul of 50% slurry per sample).
5) Mix lysates and antibody bound beads for 2 hr at 4° C.
6) Spin down beads (13000 rpm 1 min) and remove lysate.
7) Resuspend beads in 500 µl lysis buffer with the addition of 0.5M NaCl.
8) Spin down beads, remove buffer and repeat wash once more with lysis buffer plus 0.5M NaCl then twice more with lysis buffer with no NaCl then once more with 1× kinase assay buffer.
9) Spin down and remove all supernatant. For western blot add 20 µl SDS PAGE sample buffer to beads, heat for 10 min at 70° C. and run on gel.
10) For kinase assay resuspend beads in 50 µl kinase assay buffer and incubate for 20 min at 30° C.
11) Spot 40 µl of the kinase buffer onto 1.5 cm square whatman p81 paper and place into 50 mM phosphoric acid to terminate the kinase reaction.
12) Wash p81 papers 3×15min in 50 mM phosphoric acid. Dry and count.
Kinase Assay Buffer
50 mM Tris HCL pH 7.5
0.1 mM EGTA
10 mM MgCl
0.1 mM $^{32}$P ATP (approx 300 cpm/pmol)
0.1% B-mercaptoethanol
20 uM Nictide substrate
Materials and Methods.

Materials. Protease-inhibitor cocktail tablets were obtained from Roche; P81 phosphocellulose paper was from Whatman; [γ32P]-ATP and all protein chromatography media were purchased from Amersham Biosciences. Myelin basic protein (MBP) was from Invitrogen, Precast SDS polyacrylamide Bis-Tris gels were from Invitrogen; tissue culture reagents were from Life Technologies; Millipore Immobilon-P was from Fisher Scientific. Active rat ROCKII [residues 2-543] was expressed in baculovirus by the Division of Signal Transduction Therapy Unit (University of Dundee). The LRRKtide peptide (RLGRDKYKTLRQIRQ; SEQ ID NO:1) was synthesised by Dr Graham Bloomberg at the University of Bristol.

Antibodies. The anti-GST was raised in sheep against the glutathione S-transferase protein. The secondary antibodies coupled to horseradish peroxidase used for immunoblotting were obtained from Pierce.

General methods. Tissue culture, transfection, immunoblotting, restriction enzyme digests, DNA ligations, and other recombinant DNA procedures were performed using standard protocols. All mutagenesis was carried out using the Quick-Change site-directed mutagenesis method (Stratagene). DNA constructs used for transfection were purified from *E. coli* DH5α using Qiagen plasmid Mega or Maxi kit according to the manufacturer's protocol. All DNA constructs were verified by DNA sequencing, which was performed by The Sequencing Service, School of Life Sciences, University of Dundee, Scotland, UK, using DYEnamic ET terminator chemistry (Amersham Biosciences) on Applied Biosystems automated DNA sequencers.

Buffers. Lysis Buffer contained 50 mM Tris/HCl pH 7.5, 1 mM EGTA, 1 mM EDTA, 1% (w/v) Triton-X100, 1 mM sodium orthovanadate, 10 mM sodium-β-glycerophosphate, 50 mM sodium fluoride, 5 mM sodium pyrophosphate, 0.27 M sucrose, 0.1% (v/v) 2-mercaptoethanol and complete proteinase inhibitor cocktail (one tablet/50 ml, Boehringer). Buffer A contained 50 mM Tris/HCl pH 7.5, 0.1 mM EGTA and 0.1% (v/v) 2-mercaptoethanol. Extraction Buffer contained 50 mM Tris/HCl pH 7.5, 5% (v/v) glycerol, 10 mM 2-mercaptoethanol, 1 mM EDTA, 1 mM EGTA, 0.03% (v/v) Brij-35, complete proteinase inhibitor cocktail (one tablet/50 ml). Sample Buffer was 1× NuPAGE® LDS sample buffer (Invitrogen) containing 1% (by vol) 2-mercaptoethanol.

Plasmids. A full-length cDNA clone encoding LRRK2 corresponding to NCBI Acc. AAV63975 was a generous gift from Dr Michel Goedert (LMB Cambridge). The full length and the fragments of LRRK2 gene that were utilized in this study were amplified from the LRRK2 cDNA fragment, according to standard PCR methods, using KOD polymerase (Novagen). The resulting PCR products were subcloned into mammalian pEBG2T and pCMV5 expression vectors as Bamh1-Not1 fragments. A cDNA encoding full-length as well as C-terminal fragments of human moesin (NCBI Acc. NP_002435) were amplified by PCR from an EST ordered from Geneservice (IMAGE clone 4908580). The PCR product was ligated into different expression vectors as Not1-Not1 fragments.

Expression and purification of GST-LRRK2. Typically 10 to 100 ten cm diameter dishes of HEK 293 cells, were cultured and each dish transfected with 5 µg of the pEBG-2T construct encoding wild type or different mutant forms of LRRK2 using the polyethylenimine method. The cells were cultured for a further 36 h and lysed in 0.5 ml of ice-cold lysis buffer, the lysates pooled and centrifuged at 4° C. for 10 min at 26,000×g. The GST-fusion proteins were purified by affinity chromatography on glutathione-Sepharose (10 µl per dish of 293 cells) and were eluted in Buffer A containing 20 mM glutathione and 0.27 M sucrose. The enzyme was snap frozen in small aliquots and stored at −80° C.

Expression and purification of human moesin in *E. coli*. The pGEX expression constructs encoding wild type and mutant forms of human moesin were transformed into *E. coli* BL21 cells and 1-liter cultures were grown at 37° C. in Luria Broth containing 100 µg/ml ampicillin until the absorbance at 600 nm was 0.8. Induction of protein expression was carried out by adding 100 µM isopropyl-β-D-galactoside and the cells were cultured for a further 16 hr at 26° C. Cells were isolated by centrifugation, resuspended in 15 ml of ice-cold Lysis Buffer and lysed in one round of freeze/thawing, followed by sonication to fragment DNA. The lysates were centrifuged at 4° C. for 30 min at 26,000×g, and the recombinant proteins were affinity purified on 0.2 ml of glutathione-Sepharose and were eluted in 0.4 ml of Buffer A containing 20 mM glutathione and 0.27 M sucrose.

Mapping the sites on Moesin phosphorylated by the G2019S LRRK2. Moesin (4 µg) was treated at 65° C. for 15 min and then incubated at 30° C. with 1.5 µg of GST-LRRK2 [1326-2527, G2019S] in Buffer A containing 10 mM MgCl$_2$ and 100 µM [γ$^{32}$P]-ATP (10000 cpm/pmol) in a total reaction volume of 50 µl. The reaction was terminated after 40 min by adding Sample Buffer to a final concentration of 1% (w/v) LDS-10 mM dithiothreitol (DTT) and the samples heated at 100° C. for 1 min and cooled on ice. 4-vinylpyridine was added to a concentration of 50 mM, and the sample was left on a shaking platform for 30 min at room temperature to alkylate cysteine residues. The samples were subjected to electrophoresis on a BisTris 4-12% polyacrylamide gel, which was stained with colloidal blue and then autoradiographed. The phosphorylated moesin band was excised, cut into smaller pieces, washed sequentially for 15 min on a vibrating platform with 1 ml of the following: water, a 1:1 mixture of water and acetonitrile, 0.1 M ammonium bicarbonate, a 1:1 mixture of 0.2 M ammonium bicarbonate and acetonitrile and finally acetonitrile. The gel pieces were dried by speedi-vac and incubated in 0.1 ml of 50 mM ammonium bicarbonate, 0.1% (w/v) n-octyl-glucoside containing 1 µg of mass spectroscopy grade trypsin (Promega). After 16 h, 0.1 ml of acetonitrile was added and the mixture incubated on a shaking platform for 10 min. The supernatant was removed and the gel pieces were further washed for 10 min in 0.3 ml of 50 mM ammonium bicarbonate, and 0.1% v/v trifluoroacetic acid. The combined supernatants, containing >90% of the 32P-radioactivity, were chromatographed on a Vydac 218TP5215 C18 column (Separations Group, Hesperia, Calif.) equilibrated in 0.1% v/v trifluoroacetic acid in water. The column was developed with a linear acetonitrile gradient (diagonal line) at a flow rate of 0.2 ml/min and fractions of 0.1 ml were collected. Phosphopeptides were further purified by Immobilised Metal-chelate Affinity Chromatography (IMAC) on Phospho-Select resin (Sigma).

Phosphopeptide sequence analysis. Isolated phosphopeptides were analysed on an Applied Biosystems 4700 Proteomics Analyser (MALDI-TOF-TOF) using 5 µg/ml alpha cyannocinnamic acid as the matrix. Spectra were acquired in both reflectron and linear modes and the sequence of phosphopeptides were confirmed by performing MALDI-MS/MS on selected masses. The characteristic loss of phosphoric acid (M-98 Da) from the parent phosphopeptide as well as the neutral loss of dehydroalanine (M-69 kDa) for phosphoserine or dehydroaminobutyric acid (−83) for phosphothreonine was used to assign the position of the phosphorylation site(s). The site of phosphorylation of all the 32P-labelled peptides was determined by solid-phase Edman degradation on an Applied Biosystems 494C sequenator of the peptide coupled to Sequelon-AA membrane (Milligen) as described previously.

Assay of LRRK2 using moesin or MBP as substrates. Assays were set up in a total volume of 25 µl of Buffer A containing 0.5-0.7 µg of either wild type or mutant forms of LRRK2, 1 µM moesin (full length or indicated mutants, that had been left on ice or incubated at 65° C. for 15 min prior to assay) or 1 µM myelin basic protein, 10 mM MgCl$_2$ and 0.1 mM [γ$^{32}$P]-ATP (300 cpm/pmol). After incubation for 30 min at 30° C., the reactions were stopped by the addition of LDS-Sample Buffer. The incorporation of phosphate into moesin or MBP substrates as well as LRRK2 autophosphorylation was determined after electrophoresis of samples on a 4-12%-polyacrylamide gels and autoradiography of the dried Coomassie Blue-stained gels. The phosphorylated substrates were also excised from the gel and 32P-incorporation quantified by Cherenkov counting.

Assay of LRRK2 using LRRKtide as substrate. Assays were set up in a total volume of 50 µl of Buffer A containing 0.5-0.7 µg of either wild type or mutant forms LRRK2, 10 mM MgCl$_2$ and 0.1 mM [γ$^{32}$P]-ATP (300 cpm/pmol) in the presence of 300 µM or the indicated concentration of LRRKtide (RLGRDKYKTLRQIRQ; SEQ ID NO:1) peptide substrate. After incubation for 30 min at 30° C., reactions were terminated by applying 40 µl of the reaction mixture onto P81 phosphocellulose paper and phosphorylation of LRRKtide was quantified following washing the P81 phosphocellulose in 50 mM phosphoric acid and Cherenkov counting. One Unit (U) of LRRK2 activity was defined as the amount of enzyme that catalysed the incorporation of 1 nmol of $^{32}$P into LRRKtide. $K_m$ and $V_{max}$ parameters were determined by performing the assay described above using varying concentration of LRRKtide. The $K_m$ and $V_{max}$ parameters were calculated using the Graph-Pad prism programme.

Immunoblotting. Samples were heated at 70° C. for 5 min in Sample Buffer, subjected to polyacrylamide gel electrophoresis and transferred to a nitrocellulose membrane. Membranes were blocked for 30 min in 50 mM Tris/HCl pH 7.5, 0.15 M NaCl, 0.2% (v/v) Tween (TBST Buffer) containing 10% (w/v) skimmed milk. The membranes were probed with 1 μg/ml of anti-GST antibody for 16 h at 4° C. in TBST Buffer containing 5% (w/v) skimmed milk. Detection was performed using horseradish peroxidase conjugated secondary antibodies and the enhanced chemiluminescence reagent.

EXAMPLE 2

Assay Formats Suitable for Compound Screening

Protein kinase screening assay formats known in the art may be used, adapted in view of the identification of substrate polypeptides of the invention as substrates of LRRK2 polypeptides.

For example, the techniques used in Example 1 or in PCT/GB2008/001211 may be used in screening compounds. Assays similar to those described WO 03/087400 may be used. Screening assays which are capable of high throughput operation may be used. For example, assays using a substrate polypeptide of the invention, for example using an antibody binding to the phosphorylated form of the peptide but not the unphosphorylated for (or vice versa) may be suitable.

Cell based assays may be used, for example when assessing the effect of compounds on cell volume responses.

Protein-protein binding assays may be used, for example using surface plasmon resonance-based techniques or chip-based binding assays, as well known to those skilled in the art.

SPA-based (Scintillation Proximity Assay; Amersham International) assays may be used as well known to those skilled in the art. For example, beads comprising scintillant and a substrate polypeptide of the invention may be prepared. The beads may be mixed with a sample comprising $^{32}$P- or $^{33}$P-γ-labelled ATP, a LRRK2 polypeptide and with the test compound. Conveniently this is done in a 96-well format. The plate is then counted using a suitable scintillation counter, using known parameters for $^{32}$P or $^{33}$P SPA assays. Only $^{32}$P or $^{33}$P that is in proximity to the scintillant, i.e. only that bound to the substrate that is bound to the beads, is detected. Variants of such an assay, for example in which the substrate polypeptide is immobilised on the scintillant beads via binding to an antibody or antibody fragment, may also be used.

A non-radioactive assay, suitable for screening of small drug-like compound libraries, in an ELISA format can be used.

Anti-phospho-peptide antibodies can be raised in sheep, for example for use in western blotting. They are evaluated for use in the ELISA format. Immobilization of the substrate polypeptide to a microtitre plate, eg by absorption or capture via GST-tag, is not expected to affect the ability of the LRRK2 polypeptide to phosphorylate it.

The assay can be performed in maxisorp (Nunc) 384-clear plates. The substrate polypeptide, 30 ng/well, is coated overnight at 4° C. in Tris buffered saline (TBS) pH 7.4. Excess binding sites are blocked with 5% BSA in TBS containing 0.2% Tween (TBST) for 1 hour at room temperature and then washed three times with TBST. 15μl LRRK2 (1-1000 ng) in reaction buffer (50 mM Tris pH 7.5, 0.01% BSA, 0.1 mM EGTA, 1 mM DTT) is added to the well and 2 μl of compound dissolved in 11% DMSO was added and incubated for 30 minutes. The reaction is initiated by the addition of 5 μL ATP (1-1000 μM)/10 mM $MgCl_2$ and incubated at room temperature for 25 minutes. The reaction is stopped by addition of 20 μL 0.5 M EDTA. The plates were washed three times with TBST before the addition of 22 μL anti-phospho-polypeptide antibody (diluted 1:3700 fold in TBST containing 20 μg/ml blocking peptide). After 1 hour the plates are washed three times with TBST and then 22 μL of anti-sheep-peroxidase conjugate (1:5000 dilution in 1% BSA/TBST) is added to each well and incubated a further 1 hour. A final four washes of TBST are performed before addition of 22 μl peroxidase substrate 3,3',5,5'tetramethylbenzidine TMB in 50 mM acetic acid, 50 mM sodium Acetate, 0.0009% $H_2O_2$. Colour is developed for 15 minutes and stopped by addition of 5 μL 1M HCl. Plates are read on an absorbance reader at 450 nm.

Alternative commercially available peroxidase substrates could be used, which would allow different colour detection. For example orthophenylenediamine (OPD) which is read at 492 nm or Diammonium 2,2'-azino-bis(3-ethyl-benzothiazoline-6-sulfonate) which is read at 405 nm. Alternative detection technologies can also be applied using fluorescent substrates such as 10-acetyl-3.7,dihydroxyphenoxazine or luminal based sustrates for luminescence.

The assay is considered to be tolerant to a wide range of ATP concentrations (1-1000 μM) and 1% DMSO (compound storage solvent). Compound interference by autofluorescence, quenching or absorbance is considered to be minimised as it is heterogeneous involving several wash steps.

EXAMPLE 3

Generation of Antibodies to LRRK2

Antibodies to LRRK2 were generated in sheep using the immunogen sequences shown in Table 2. Only the antibodies raised to LRRK2 (100-500) (immunogen shown in FIG. 11) were considered to be useful in immunoprecipitating LRRK2 that retained protein kinase activity and was therefore useful in a protein kinase assay. The antibody S224C raised to LRRK2 (2078-2099) immunoprecipitated LRRK2 but was inhibitory to the kinase activity. Antibody LRRK2 (1245-1259) is considered to be useful in immunoblotting but is not considered to be useful for immunoprecipitation.

TABLE 2

Anti-LRRK2 antibodies

| Sheep No. | Antibody Name | Immunogen Sequence |
| --- | --- | --- |
| S869B | LRRK2 (1-190) | GST-LRRK2 [DU 6688] |
| S137C | LRRK2 (1326-2527) | GST-LRRK2 [DU 10525] |
| S348C | LRRK2 (100-500) | LRRK2 (100-500) GST cleaved [DU 13636] |
| S407C | LRRK2 (100-500) | LRRK2 (100-500) GST cleaved [DU 13636] |
| S750B | LRRK2 (16-35) | LKKLIVRLNNVQEGKQIETL [residues 16-35 of human] (SEQ ID NO: 54) |
| S224C | LRRK2 (2078-2099) | KFPNEFDELEIQGKLPDPVKEY [residues 2078-2099 of human] (SEQ ID NO: 55) |

TABLE 2-continued

Anti-LRRK2 antibodies

| Sheep No. | Antibody Name | Immunogen Sequence |
| --- | --- | --- |
| S374C | LRRK2 (2498-2514) | CINLPHEVQNLEKHIEVRV [residues 2498-2514 of human + N-terminal systeine for coupling] (SEQ ID NO: 56) |
| S616B | LRRK2 (2508-2527) | EKHIEVRKELAEKMRRTSVE [residues 2508-2527 of human] (SEQ ID NO: 57) |
| S357C | LRRK2 phospho Ser 910 | VKKKSNS*ISVGEFY [residues 904-917 of human] (SEQ ID NO: 58) |
| S044C | LRRK2 phospho Thr 1503 | CLAKLRKT*IINESLN [residues 1497-1510 of human + N-terminal cysteine for coupling] (SEQ ID NO: 59) |
| S146C | LRRK2 phospho Thr 1503 | CLAKLRKT*IINESLN [residues 1497-1510 of human + N-terminal cysteine for coupling] (SEQ ID NO: 60) |
| S994B | LRRK2 (1245-1259) | CRVEKLHLSHNKLKEI [residues 1245-1259 of mouse + N-terminal cysteine for coupling] (SEQ ID NO: 61) |
| S994B | LRRK2 (2078-2096) | CFPNEFDELAIQGKLPDPV [residues 2078-2096 of mouse + N-terminal cysteine for coupling] (SEQ ID NO: 62) |
| S184C | LRRK2 (2078-2096) | CFPNEFDELAIQGKLPDPV [residues 2078-2096 of mouse + N-terminal cysteine for coupling] (SEQ ID NO: 63) |
| S225C | LRRK2 (2078-2099) | RFPNEFDELAIQGKLPDPVKEY [residues 2078-2099 of mouse] (SEQ ID NO: 64) |

EXAMPLE 4

Substrate Specificity and Inhibitors of the Parkins's Disease Mutated Protein Kinase LRRK2

The Leucine Rich Repeat Protein Kinase-2 (LRRK2) is mutated in a significant number of Parkinson's disease patients, but little is known about its regulation and function. A common mutation changing Gly2019 to Ser enhances catalytic activity, suggesting small molecule inhibitors might have utility in treating Parkinson's Disease. We utilised various approaches to explore the substrate specificity requirements of LRRK2 and elaborated a peptide substrate termed Nictide that had 20-fold lower $K_m$ and nearly 2-fold higher $V_{max}$ than the widely deployed LRRKtide substrate. We demonstrate that LRRK2 has marked preference for phosphorylating Thr over Ser. We also observed that several Rho kinase (ROCK) inhibitors, such as Y-27632 and H-1152, suppressed LRRK2 with similar potency to which they inhibited ROCK2. We also identified a mutant LRRK2[A2016T] that was normally active, but resistant to H-1152, Y-27632 as well as sunitinib, a structurally unrelated multikinase inhibitor that in contrast to other compounds also suppresses LRRK2, but not ROCK. We have also developed the first assay to measure the protein kinase activity of endogenous LRRK2. Finally, we describe a pharmacological approach to validate whether substrates are phosphorylated by LRRK2 and use this to provide evidence that LRRK2 may not be rate-limiting for the phosphorylation of the proposed substrate moesin. Our findings reported in this study will aid with the investigation of the LRRK2 kinase.

Autosomal dominant point mutations within the gene encoding for the Leucine Rich Repeat protein Kinase-2 (LRRK2) predispose humans to Parkinson's disease (PD). Patients with LRRK2 mutations generally develop PD at the normal age of 60-70 years, with clinical appearance and symptoms indistinguishable from idiopathic PD. Mutations in LRRK2 account for 4% of familial PD, and observed in 1% of sporadic PD patients. Little is known about how LRRK2 is regulated, what its substrates are and how mutations cause PD.

LRRK2 is a large multi-domain protein kinase of 2527 residues, consisting of leucine rich repeats (residues 1010-1287), GTPase domain (residues 1335-1504), COR domain (residues 1517-1843), serine/threonine protein kinase domain (residues 1875-2132) and a WD40 repeat (2231-2276). Over 40 mutations have thus far been reported which mainly comprise amino acid substitutions]. The most frequent mutation comprises an amino acid substitution of the highly conserved Gly2019 located within the subdomain VII-DFG motif of the kinase domain to a Ser residue. Several studies have reported that this mutation enhances the protein kinase activity of LRRK2 two to three-fold, suggesting that LRRK2 inhibitors may have utility for the treatment of PD. Other than non-specific/multi-kinase protein kinase inhibitors staurosporine (IC50 2 nM), K252 (IC50 4 nM), Su-11248/sunitinib (IC50 15 nM) no selective LRRK2 inhibitors have been reported thus far.

We previously undertook a KESTREL screen in rat brain extracts to identify proteins phosphorylated by the activated PD LRRK2[G2019S] mutant. This led to the observation that moesin, a member of the ERM proteins that anchors the actin-cytoskeleton to the plasma membrane is efficiently phosphorylated by LRRK2, at Thr558, a previously identified in vivo phosphorylation site that regulates the ability of moesin to bind actin. LRRK2 also phosphorylated other ERM proteins, ezrin and radixin that are related to moesin, at the residue equivalent to Thr558, as well as a peptide encompassing Thr558 (LRRKtide). Previous work had suggested that the Rho-kinase (ROCK) could also phosphorylate ERM proteins at the residue equivalent to Thr558 of moesin both in vitro and when overexpressed in cells. No evidence has been published to demonstrate that LRRK2 phosphorylates ERM proteins in cells.

To aid the functional characterisation of LRRK2, we have analysed the substrate specificities of LRRK2 and elaborated the peptide substrate Nictide that has a 20-fold lower $K_m$ and nearly 2-fold higher $V_{max}$ than the widely deployed LRRKtide substrate. We also observed that some previously reported ROCK inhibitors also inhibited LRRK2 with similar potency as they inhibited ROCK. Moreover, we demonstrate that sunitinib can be deployed as a control compound that inhibits LRRK2 but not ROCK. We generated an inhibitor-resistant mutant of LRRK2 that is normally active, but 20-fold less sensitive to inhibition by the LRRK2 inhibitors. We also develop the first robust assay that allows the protein kinase activity of endogenous LRRK2 to be quantified and present a pharmacological strategy that can be deployed to validate LRRK2 substrates. The findings presented in this study will help with dissecting the regulation and function of LRRK2.

Materials and Methods

Reagents and General methods. Tissue-culture reagents were from Life Technologies. Glutathione Sepharose 4B was from Amersham Biosciences and [γ-$^{32}$P]-ATP and [γ-$^{33}$P]-ATP was from Perkin Elmer. P81 phosphocellulose paper was from Whatman. LRRKtide and its derivatives were synthesized by Pepceuticals. The Flp-in T-REx system was from Invitrogen and stable cell lines were generated as per manufacturer instructions by selection with hygromycin. Restriction-enzyme digests, DNA ligations and other recombinant DNA procedures were performed using standard protocols. All mutagenesis was carried out using the Quick-Change site-directed-mutagenesis kit (Stratagene). DNA constructs used for transfection were purified from *Escherichia coli* DH5α using Qiagen or Invitrogen plasmid Maxi kits according to the manufacturer's protocol. All DNA constructs were verified by DNA sequencing, which was performed by The Sequencing Service, School of Life Sciences, University of Dundee, Scotland, U.K., using DYEnamic ET terminator chemistry (Amersham Biosciences) on Applied Biosystems automated DNA sequencers.

Figure 6:
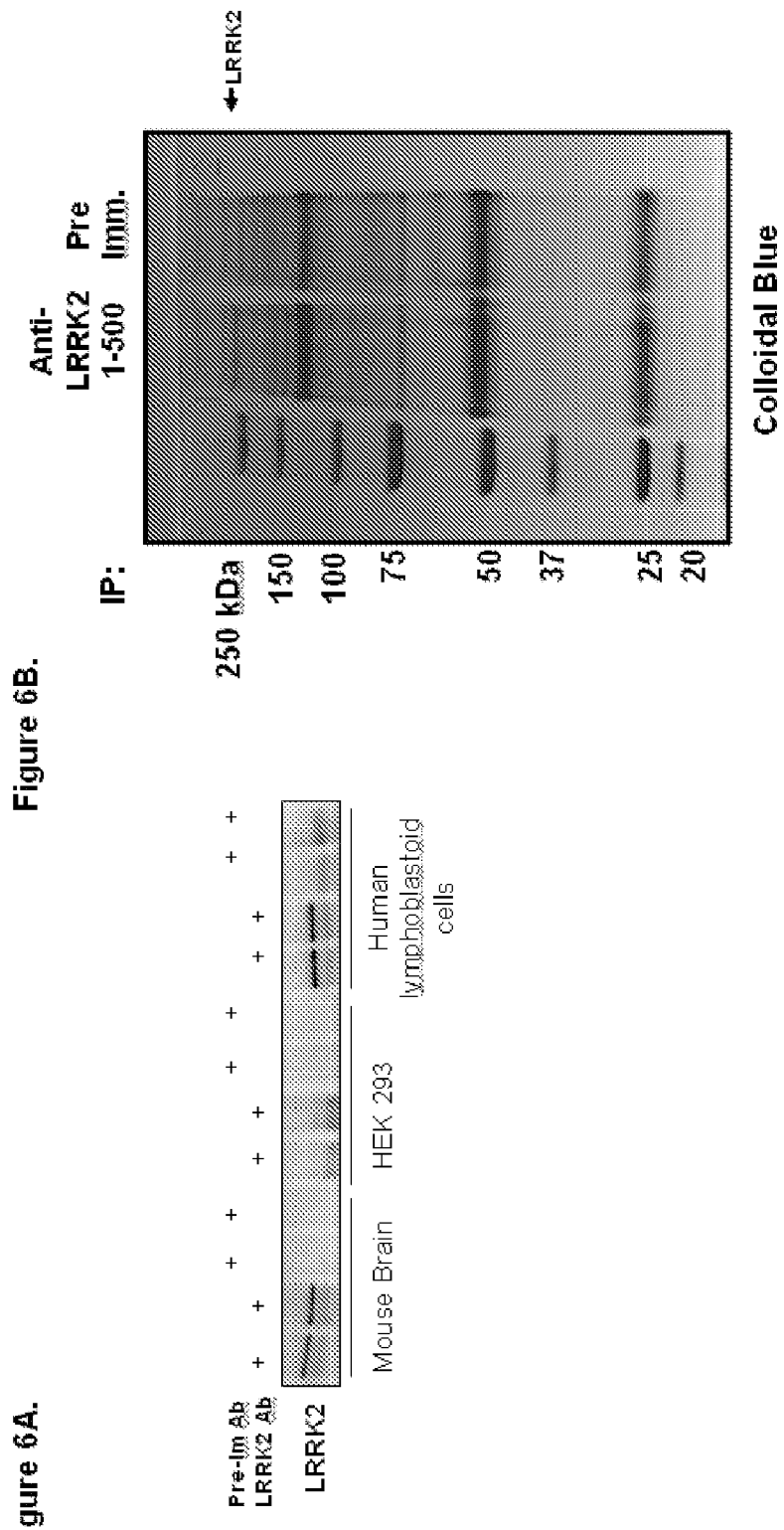
FIG. 6. The anti-LRRK2 1-500 antibody immunoprecipitates endogenous protein from mouse brain lysate, and human lymphoblastoid lystates, FIG. 6A. The LRRK2 antibody was used in an immunoprecipitation of 13 mg of NIH3T3 lysate. The immunoprecipitates were eluted with sample buffer and resolved on a 4-12% Novex gel and stained with colloidal blue, FIG. 6B. Bands 1 and 2 were excised and subjected to analysis by mass spectrometry. Band contained 16 peptide matches for LRRK2, while band 2 contained no peptides matching LRRK2.
Figure 7:
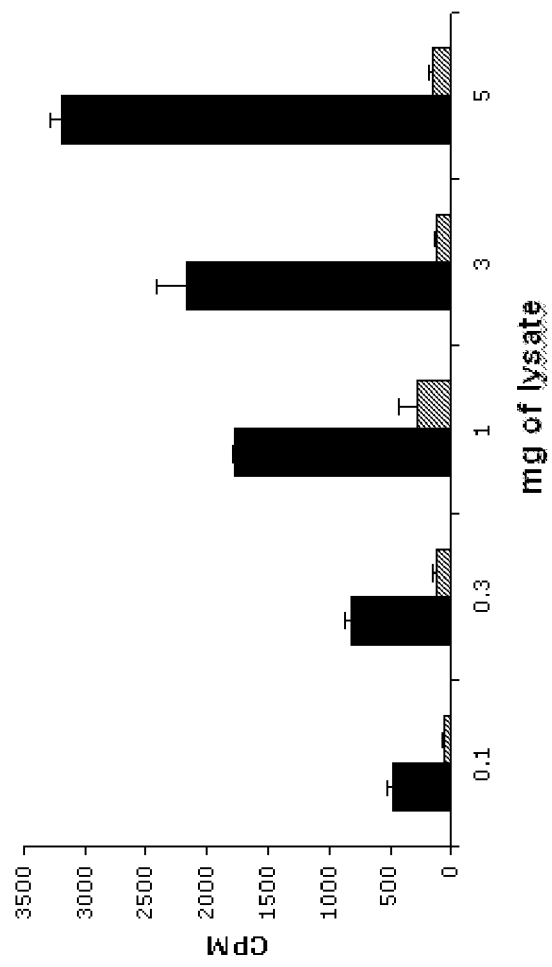
FIG. 7. Increasing amounts of NIH3T3 lysate were used to immunoprecipitate LRRK2 and were assayed for activity against Nictide. Anti-LRRK2 reactions are represented in black bars and pre-immune reactions are in grey bars.

Buffers. Lysis Buffer contained 50 mM Tris/HCl, pH 7.5, 1 mM EGTA, 1 mM EDTA, 1% (w/v) 1 mM sodium orthovanadate, 10 mM sodium β-glycerophosphate, 50 mM NaF, 5 mM sodium pyrophosphate, 0.27 M sucrose, 1 mM Benzamidine and 2 mM phenylmethanesulphonylfluoride (PMSF) and was supplemented with either Triton X-100 or 0.5% (v/v) NP-40 with 150 mM as indicated. Buffer A contained 50 mM Tris/HCl, pH 7.5, 50 mM NaCl, 0.1 mM EGTA and 0.1% (v/v) 2-mercaptoethanol, and 0.27 M sucrose. Sodium dodecyl sulfate (SDS) lysis buffer employed to lyse cells in FIG. 6 was lysis buffer supplemented with 1% SDS and 0.1% 2-mercaptoethanol and pH adjusted 6.8.

Cell culture, treatments and cell lysis. HEK-293 cells were cultured in Dulbecco's Modified Eagle's medium supplemented with 10% FBS, 2 mM glutamine and 1× antimycotic/antibiotic solution. T-REx cell lines were cultured in DMEM supplemented with 10% FBS and 2 mM glutamine, 1× antimycotic/antibiotic, and 15 μg/ml Blastocidin and 100 ug/ml hygromycin. Cell transfections were performed by the polyethylenimine method. Cultures were induced to express the indicated protein by inclusion of 1 μg/ml doxycycline in the culture medium for the indicated times. Where inhibitors are utilized, they were dissolved in DMSO and used at the indicated concentrations with an equivalent volume of DMSO used as a control. The final concentration of DMSO in the culture medium was never more than 0.1% (v/v). Inhibitors were added to the culture medium 60 min prior to lysis. Cells were lysed with 1.0 ml of lysis buffer per 15 cm dish supplemented with the indicated detergent and clarified by centrifugation at 16,000×g at 4° C. for 10 minutes. After induction and inhibitor treatment, T-REx-GFP Rho expressing cells were lysed at room temperature with SDS lysis buffer after washing with PBS. SDS lysates were boiled and sonicated to reduce viscosity. All lysate supernatants were snap frozen in liquid nitrogen and stored at −80° C. until use. Protein concentrations were determined using the Bradford method with BSA as the standard.

Purification of recombinant proteins. Recombinant glutathione-s transferase (GST)-LRRK2 1326-2527 and variants thereof were prepared as described in [9], except that lysis buffer contained 0.5% (v/v) NP-40 and 150 mM NaCl. The following recombinant proteins were generated in the Division of Signal Transduction Thearapy at the University of Dundee: rat ROCK2 (amino acids 2-543), chicken maltose binding protein-MYPT (amino acids 714-1004), GST-ezrin (amino acids 1-586), GST-moesin (amino acids 1-577) and GST-LRRK2 (amino acids 100-500). Peptide substrates were displayed as GST fusions in the pGEX-6P vector. To induce the expression of GST-LRRKtide and GST-Nictide, *Escherichia coli* BL21 transformants were grown to an OD600 of 0.5 at 37° C. and induced at 16 ° C. by the addition of isopropyl β-D-1-thiogalactopyranoside to a final concentration of 1 mM. Cells were lysed by sonication in lysis buffer with 1% (v/v) Triton X-100. The soluble fraction was retrieved by centrifugation at 15000×g for 20 minutes. Recombinant protein was purified by glutathione sepharose chromatography and proteins were eluted in buffer A with 20 mM glutathione, 1 mM benzamidine and 2 mM PMSF.

Antibodies. A glutathione-s transferase (GST) fusion protein of amino acids was expressed in bacteria and purified by glutathione sepharose chromatography. Following cleavage of the GST tag, LRRK2 [100-500] was used as an immunogen to raise a polyclonal antibody (S348C). Antibodies were affinity purified from antisera using the LRRK2 [100-500] protein immunogen. Antibody (S374C) against LRRK2 was raised against a peptide immunogen encompassing amino acids 2498-2514 (CINLPHEVQNLEKHIER with NH2 cysteine for coupling to keyhole limpet hemocyanin[KLH]). Antibodies were affinity purified against the peptide. Anti-moesin (S135C) and anti-ezrin antibodies (S245C) were generated by injection of purified full-length protein into sheep, followed by affinity purification of the antibody against the antigen. Pan phospho-ERM antibody (S296C) was generated by injection of the KLH conjugated phosphopeptide CDKYKTpLRQI into sheep and was affinity purified by positive and negative selection against the phospho and de-phospho peptides respectively. Sheep polyclonal antibody (S662B) was raised against MBP-MYPT chicken amino acids (714-1004). Rabbit polyclonal antibody against MYPT phosphothreonine 850 was from Upstate (#36-003). Anti GFP antibody (S268B) was raised against recombinant GFP protein and affinity purified against the antigen. Antibody (S221 B) against ERK1/2 was raised against GST-ERK1 protein. Anti-FLAG M2 antibody and affinity matrix were from Sigma (A2220).

Specificity kinase panel. All assays were performed at the The National Centre for Protein Kinase Profiling. Briefly, all assays were carried out robotically at room temperature (approximately 21° C.) and were linear with respect to time and enzyme concentration under the conditions used. Assays were performed for 30 min using Multidrop Micro reagent dispensers (Thermo Electron Corporation, Waltham, Mass., U.S.A.) in a 96-well format. The abbreviations for each kinase are defined in legend to Table 1. The concentration of magnesium acetate in the assays was 10 mM and [γ-$^{33}$P]ATP (~800 cpm/pmol) was used at 5 μM for CK2α, DYRK3, EF2K,ERK1, ERK8, GSK3β, HIPK2, HER4, IGF1R, IRR, MARK3, MKK1, p38γ MAPK, p38δ MAPK, PAK4, PIM2, Akt1, PLK1, PKCζ and PRK2; 20 μM for Aurora B, CaMKKβ, CDK2/cyclin A, CHK1, CHK2, CK1δ, CSK, EPH-B3, FGF-R1, GCK, IRAK4, IR, JNK1α1, JNK2α2, LKB1, MAPKAP-K2, MLK1, MLK3, MSK1, MST2, MST4, p38β MAPK, NUAK, PKA, PAK5, PAK6, PDK1, PIM1, PIM3, PKCα, ROCKII, PRAK, S6K1, SGK1, SYK, TTK, VEGFR and YES1; or 50 μM for AMPK, BRSK2, BTK, CaMK1, DYRK1a, DYRK2, EPH-A2, ERK2, IKKβ, IKKε, LCK, MELK, MINK1, MNK1, MNK2, NEK2A, NEK6, p38α, PhKγ1, Akt2, PKD1, RSK1, RSK2, SRPK1 Src, and TBK, in order to be at or below the $K_m$ for ATP for each enzyme.

Figure 1A:
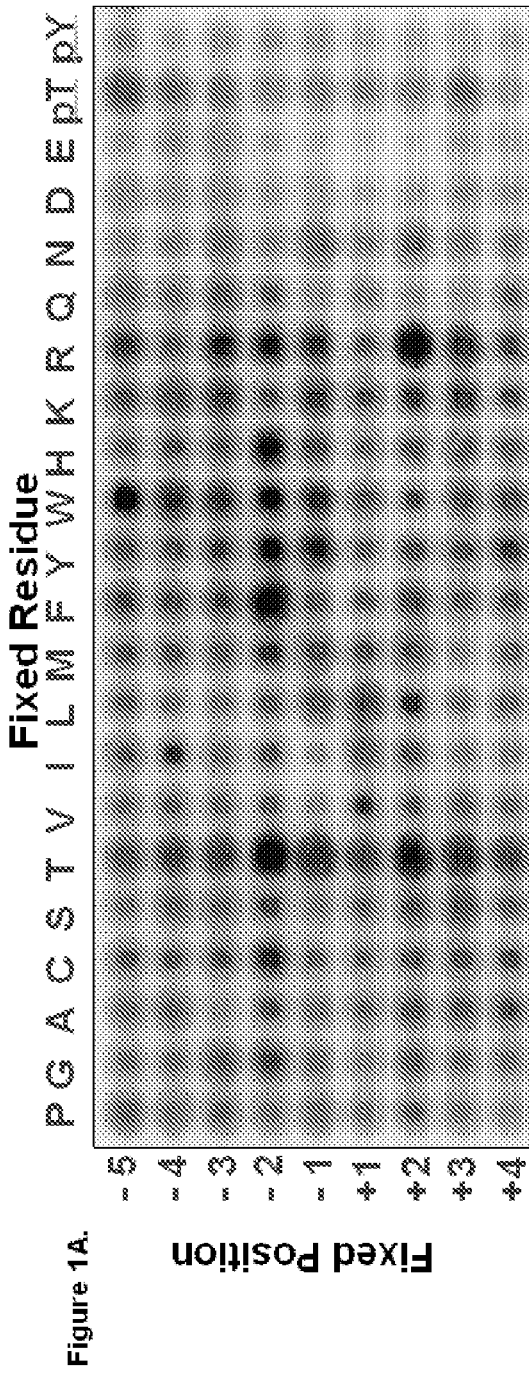
FIGS. 1A-1B and 2. GST tagged, 1326-End recombinant LRRK2 G2019S was purified from transfected HEK293 cells as described in Jaleel et al., Biochemistry 2007. This enzyme was used to determine the peptide substrate preference as described in Hutti et al., Nat Methods. 2004. Residue preferences were derived from digital quantitation of reaction products and values are shown in FIG. 1B. Control reactions were performed with a kinase dead preparation (FIG. 2).
Figure 1B:
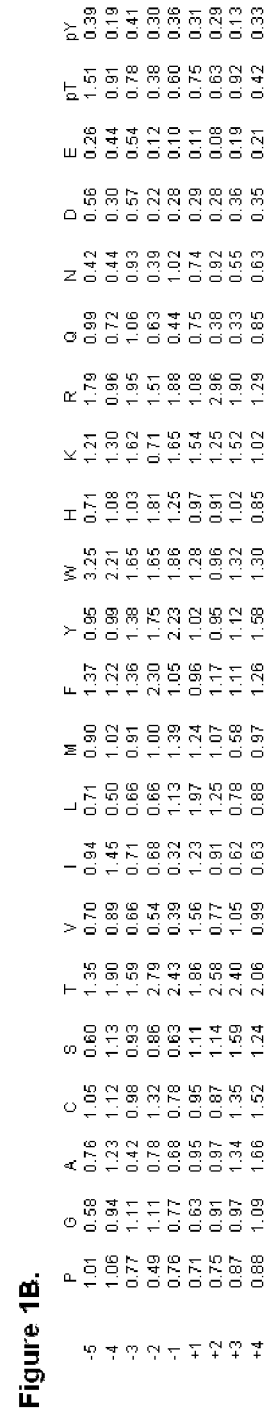
Figure 2:
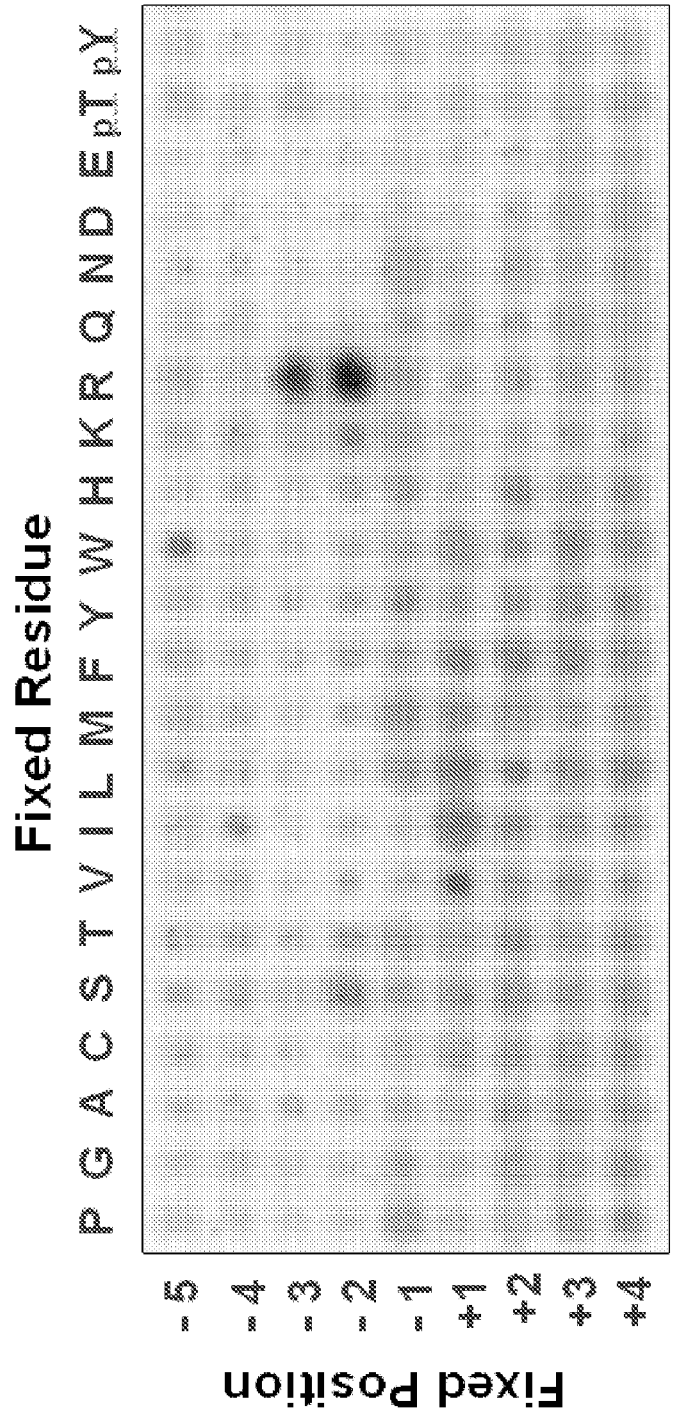

Peptide Kinase Assays. Peptide Kinase Assays were set up in a total volume of 40 μl with recombinant kinase or kinase displayed as an immune-complex coupled to protein G sepharose in 50 mM Tris pH 7.5, 0.1 mM EGTA, 10 mM $MgCl_2$ and 0.1 mM [γ-$^{32}$P]ATP (~500-1000 cpm/pmol) in the presence of the indicated concentration of peptide substrate. In reactions where kinase inhibitors were assayed, inhibitors were dissolved in dimethyl sulfoxide and were at 0.1% of the reaction volume. After incubation for 15 min at 30° C., reactions were terminated by applying 35 μl of the reaction mixture on to P81 phosphocellulose paper and immersion in 50 mM phosphoric acid. After extensive washing, reaction products were quantitated by Cerenkov counting. A unit (U) of LRRK2 activity was defined as the amount of enzyme that catalysed the incorporation of 1 nmol of $^{32}$P into LRRKtide. $K_m$ and $V_{max}$ parameters were determined by performing the assay described above using various concentrations of LRRKtide or Nictide. The $K_m$ and $V_{max}$ parameters were calculated using the Graph-Pad Prism program. Km and Vmax values are rounded in FIG. 1C to reflect the need to estimate values due to the nature of the peptide assay, wherein high concentrations of peptide became inhibitory to the kinase. IC50 values were calculated using non-linear regression analysis using Graph-Pad Prism.

Protein substrate kinase assays. Assays were set up in a total volume of 25 μl with recombinant kinase or kinase displayed as an immunecomplex coupled to protein G sepharose in 50 mM Tris pH 7.5, 0.1 mM EGTA, 10 mM $MgCl_2$ and 0.1 mM [γ-$^{32}$P] ATP (~500cpm/pmol), with substrate at 2 μM. After incubation for 15 min at 30° C., the reactions were stopped by the addition of Laemelli sample buffer. Reaction products were resolved by electrophoresis on sodium dodecyl sulfate polyacrylamide gels. The incorporation of phosphate into protein substrates was determined by autoradiography and/or immunoblotting with phospho-specific antibodies.

Immunological procedures. Cell lysates (10-30 μl) were resolved by electrophoresis on SDS polyacrylamide gels or Novex 4-12% gradient gels, and electroblotted to nitrocellulose membranes. Membranes were blocked with 5% (w/v) in Tris/HCl, pH 7.5, 0.15 M NaCl and 0.1% (v/v) Tween (TBST Buffer). For phospho-MYPT antibody, primary antibody was used at a concentration of 1 μg/ml, diluted in 5% BSA in TBST. Phospho-ERM antibody was used at 1 μg/ml in the presence of 10 μg/ml LRRKtide, diluted in 5% (w/v) skimmed milk in TBST. All other antibodies were used at 1 μg/ml in 5% (w/v) milk in TBST. Detection of immune-complexes was performed using horseradish-peroxidase-conjugated secondary antibodies (Pierce) and an enhanced-chemiluminescence reagent. For immunoprecipitations, antibody was non-covalently coupled to protein G-Sepharose at a ratio of 1 μg antibody/μl of beads, or anti-FLAG M2-agarose was utilized. The indicated amount of cell lysate was incubated with 5 μl bed volume of coupled antibody for 1 hour. Immune complexes were washed twice with lysis buffer supplemented with 0.5 M NaCl and twice with Buffer A. Precipitates were either used as a source of kinase or immediately analyzed by immunoblot.

Isolation and mass fingerprint identification of endogenous LRRK2. 20 μl of the above described antibody conjugate, either IgG or LRRK2, was incubated with 60 mg of Triton X-100 soluble Swiss 3T3 lysate that had been pre-cleared by incubation with protein GSepharose, for 2.5 hours at 4° C. Beads were washed four times with lysis buffer supplemented with 0.15 M NaCl and twice with buffer A. Precipitates were reduced with 10 mM dithiothreitol and then alkylated with 50 mM iodoacetamide for 30 min at room temperature. Samples were resolved on 4-12% Novex gels and stained with colloidal blue. Colloidal blue stained bands at the approximate size of LRRK2 were excised and mass fingerprinting of in-gel digested tryptic peptides. The LRRK2 band and the corresponding region of the IgG control immunoprecipitation was excised, cut into smaller pieces, washed sequentially for 15 min on a vibrating platform with 0.5 ml of the following: a 1:1 (v/v) mixture of water and acetonitrile, 0.1 M ammonium bicarbonate, a 1:1 (v/v) mixture of 0.1 M ammonium bicarbonate and acetonitrile, and finally acetonitrile. The gel pieces were dried in a speed-vac and then rehydrated in 25 mM triethylammonium bicarbonate containing 0.5 μg/ml of MS-grade trypsin (Promega). After 16 h, an equal volume of acetonitrile was added and the mixture incubated on a shaking platform for 10 min. The supernatant was dried and the remaining peptides in the gel pieces were further extracted with 0.1 ml of 50% acetonitrile/2.5% formic acid. Samples were analyzed on an LTQ Orbitrap XL mass spectrometer (Thermo). Masses were searched with the mascot server (matrixscience.com) using the International Protein Index mouse database.

Computer analysis. Autoradiography films and immunoblot film were scanned on an epson4990 scanner and images were managed with Adobe Photoshop. Protein sequence alignments were performed with MUltiple Sequence Comparison by Log-Expectation (MUSCLE) EBI and managed with JalView. Enzyme kinetic analysis was performed with GraphPad Prism.

Results

Comparison of the substrate specificities of LRRK2 and ROCK. We first compared the rates at which recombinant ROCK2 and LRRK2 phosphorylated ezrin and MYPT (a well characterised ROCK substrate). Under conditions in which equimolar MYPT and ezrin were present, ROCK2 phosphorylated MYPT but barely ezrin (FIG. 12A). In contrast, LRRK2 phosphorylated ezrin, but did not phosphorylate MYPT (FIG. 12A). Comparison of residues surrounding Thr850 (major ROCK phosphorylation site on MYPT [18]) and Thr567 (LRRK2 phosphorylation site on ezrin), revealed that overall these peptides were dissimilar with only the positions −3(RMYPT/Kezrin) possessing homology (FIG. 12A, lower panel). The human sequence surrounding the LRRK2 phosphorylation site of ezrin is identical in moesin and radixin, and also strikingly conserved in Drosophila and C. elegans ERM homologues (FIG. 12B, lower panel). To investigate the substrate specificity determinants of LRRK2, we verified how mutation of different residues affected the kinetics of LRRK2 phosphorylation of the LRRKtide peptide that encompasses the Thr567 ERM Phosphorylation motif (FIG. 12C). The wild type LRRKtide peptide was phosphorylated by LRRK2 with a $K_m$ of 200 μM and $V_{max}$ of 14 U/mg. The following mutations to Ala suppressed phosphorylation by increasing the $K_m$ value: −5Arg (2.5 fold), −2Tyr (2.4-fold), +2Arg (4.5-fold) and +5Arg (4-fold) residues. Mutation of the −2Tyr to Glu increased $K_m$ 4.4-fold, whilst its mutation to Arg slightly decreased $K_m$ suggesting that an aromatic residue at this position is not essential (FIG. 12C). Mutation of the +2 and +5 residues of the peptide to Pro or Glu increased $K_m$ similarly to the Ala mutation. Only mutation of the −4 (Asp) to Ala moderately enhanced peptide phosphorylation by decreasing $K_m$ 2.3-fold (FIG. 12C). Several mutations also markedly decreased $V_{max}$ values which included: −2 Tyr (2 to 10-fold), +1Leu (2-fold), +2 Arg (4 to 28-fold) and +5 Arg (mutation to Glu 4-fold). We also investigated how mutations in LRRKtide affected phosphorylation by ROCK2. In contrast to LRRK2, we observed that several mutations substantially improved peptide phosphorylation by decreasing the $K_m$ value. The most dramatic change involved mutation of the −2Tyr to an Arg residue that is found in most ROCK substrates. This decreased the $K_m$ value over 60-fold and increased the $V_{max}$ over 5-fold. Mutation of the +1Leu residue to Ala abolished phosphorylation by ROCK2, but had no effect on LRRK2 phosphorylation (FIG. 12C).

Figures 3A, 3B, 3C:
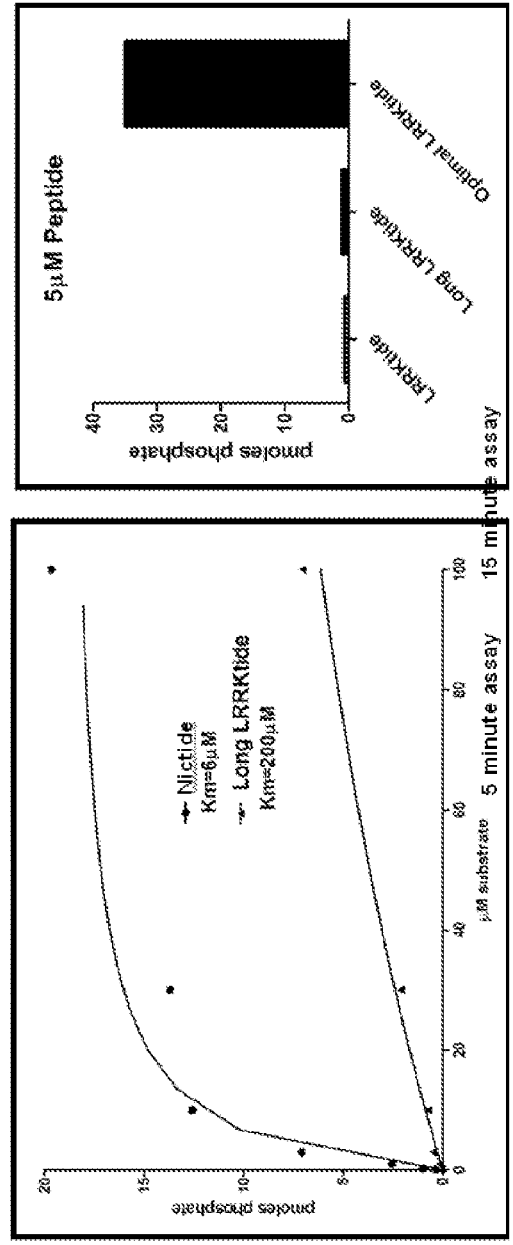
In FIG. 3A, LRRK2 residue preferences are displayed semi-quantitatively by proportional representation of single letter amino acid symbols above the position relative to phosphorylation site. A derived consensus sequences is shown below the positions.
FIG. 3B is an alignment of the peptide substrate sequences previously used for LRRK2, LRRKtide and LongLRRKtide, along with a new peptide in which the preferred LRRK2 residues are substituted, henceforth referred to as Nictide. The left panel of FIG. 3C shows concentration dependent phosphorylation of Nictide versus LongLRRKtide at 5 minute reaction times. Calculated Km values are 6micromolar for Nictide. The right panel of FIG. 3C shows a comparison of LRRKtide, LongLRRKtide and Nictide at 15 minutes at 5 micromolar peptide concentration.
Figure 4:
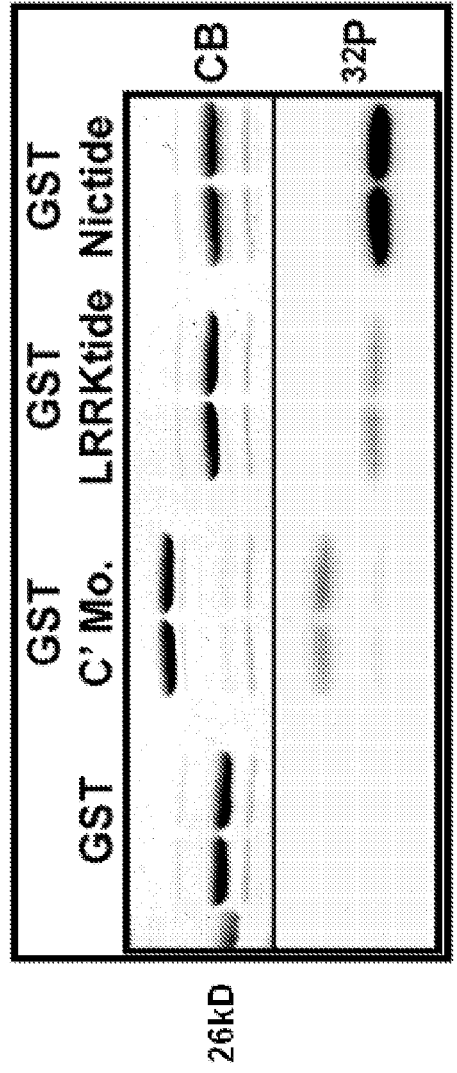
FIG. 4. Modification of Nictide displayed as a fusion to a recombinant protein. GST or fusion proteins of GST with the carboxy terminus of moesin (amino acids 500-End), the sequence of LRRKtide or Nictide were prepared from bacteria. These recombinant proteins were presented as substrates for GST tagged LRRK2 1326-End G2019S for 10 minutes in the presence of [γ-$^{32}$P]-ATP. Reaction products were resolved on 12% SDS-polyacrylamide gels and visualized by coomassie blue staining (CB) and autoradiography ($^{32}$P).
Figure 5:
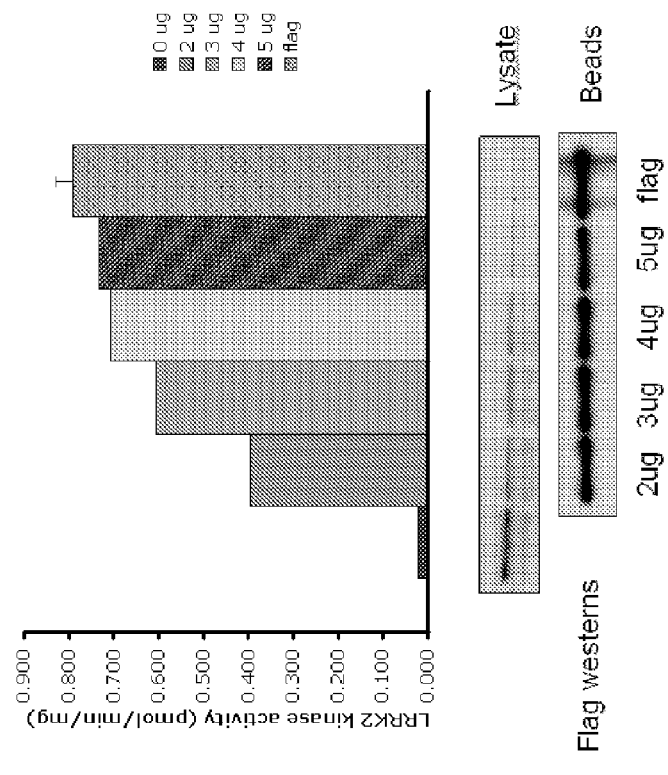
FIG. 5. An antibody was raised in sheep against the amino terminal 500 amino acids of LRRK2 using recombinant protein as an immunogen (see FIG. 11). Specific antibodies were isolated by positive selection with recombinant protein. One milligram of lysates of HEK293 cells stably expressing full length Flag tagged LRRK2 G2019S were subjected to immunoprecipitation with increasing amounts of antibody conjugated to 10 μl of protein G sepharose and anti-FLAG M2 agarose (Sigma) as control. Immunocomplexes were used in kinase assay with LongLRRKtide. Immunodepletion of LRRK2 from the lysates is shown as well as immunoblot analysis of the immunoprecipitates using anti-flag.

Elaboration of an optimal LRRK2 peptide substrate. To further investigate and improve the optimal phosphorylation motif for LRRK2, we utilized a positional scanning peptide library approach. This assay utilises 198 biotinylated peptide libraries. Each library contains a 1:1 mixture of serine and threonine at the central position and one additional position fixed to one of the 20 amino acids, phosphothreonine, or phosphotyrosine. Phosphothreonine and phosphotyrosine were included to allow identification of kinases that possess a requirement for priming phosphorylation events. All other positions contain an equimolar degenerate mixture of natural amino acids (except serine, threonine, and cysteine). Recombinant LRRK2[G2019S] or kinase inactive LRRK2 [D2017A] was used to phosphorylate all 198 peptide libraries simultaneously in solution using $\mu$-$^{32}$P-ATP, and biotinylated peptides were captured on a streptavidin-coated membrane. The relative preference for each amino acid at each position was determined by quantifying $^{32}$Pradioactivity incorporation following phosphoimaging (FIG. 3A). The quantitative results of the LRRK2[G2019S] screen were also input as a matrix into enoLOGOS programme and the relative preferences for each amino acid is displayed in FIG. 13B. We found that LRRK2 exhibited preferred sequence specificity at multiple positions relative to the phosphorylation site, with strong preferences for −5(Trp, Arg), −2(Phe, Tyr, His and Thr), −1(Tyr, Arg, Trp), +2 (Arg and Thr) and +3 (Arg) positions. This is consistent with the kinetic studies shown in FIG. 12, demonstrating that mutation of these residues increased $K_m$ and in some cases also decreased $V_{max}$ values. An Asp or Glu residue at any position with the peptide reduced LRRK2 phosphorylation (FIG. 13A). For experiments undertaken with kinase-inactive LRRK2[D2017A], vastly lower overall levels of phosphorylation were observed, but nevertheless some contaminant-kinase activity with preference for Arg residues at the −3 and −2 positions was still found. Similar results were also reported in previous studies employing recombinant kinase-inactive GST-IκB Kinase-β derived from 293 cells. This trace level of protein kinase activity probably results from protein kinases that contaminate the GSTpurified kinase from 293 cell extracts.

Elaboration of Nictide LRRK2 substrate. The data from the positional scanning peptide library indicated that the optimal LRRK2 phosphorylation motif between −5 and +4 positions is WWRFYTLRRA (SEQ ID NO:67). In order to generate an improved substrate for LRRK2, we substituted this motif into the moesin sequence, from which the LRRK2tide peptide was derived. As sequences as distant as the +5 residues affected kinetics of LRRKtide phosphorylation (FIG. 12C) and the LRRKtide peptide terminated at the +6 position, we decided to incorporate the WWRFYTLRRA motif into a longer variant of the LRRKtide peptide encompassing a further 6 residues of moesin. The resulting sequence RLGWWRFYTLR-RARQGNTKQR (SEQ ID NO:51) was termed Nictide (reflecting the names of the 2 first authors of this study). We first compared the phosphorylation by LRRK2[G2019S] of GST fused to the original LRRKtide sequence, the longer version of LRRKtide, the entire C-terminus of moesin (residues 500-577) as well as Nictide. This revealed that GST-Nictide was phosphorylated to a significantly greater extent by LRRK2 than the other GST-fusion proteins (FIG. 13C). Mutation of the Thr residue predicted to comprise the LRRK2 phosphorylation site, virtually abolished phosphorylation of the GST fusion proteins. Our results also demonstrate that the expanded LRRKtide sequence was more efficiently phosphorylated by LRRK2 than the original shorter variant (FIG. 13C).

Figure 13B:
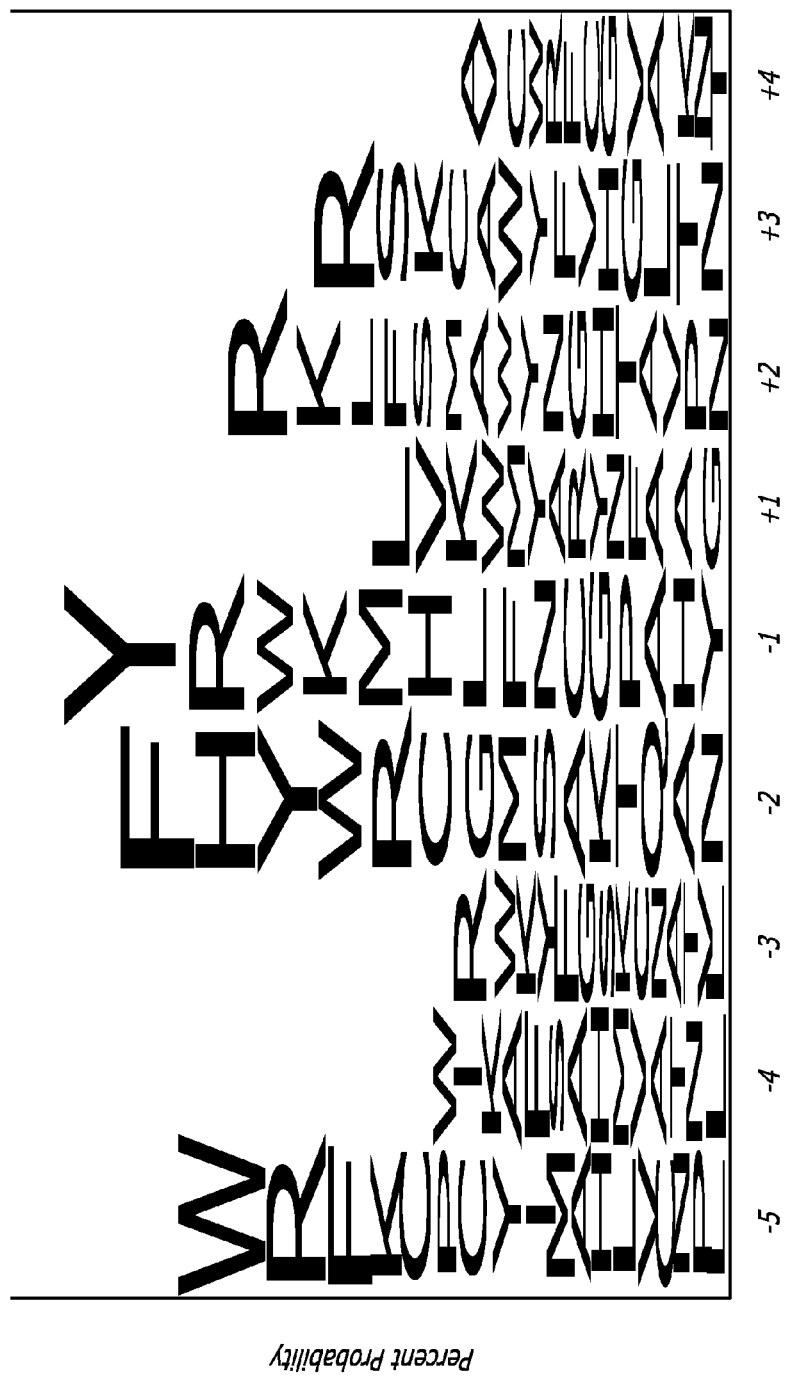
FIG. 13. Determination of the preferred substrate phosphorylation sequence for LRRK2. (A) Recombinant HEK293 purified LRRK2 (1326-2527) [G2019S] enzyme and LRRK2 (1326-2527) [D2017A] was used to screen a positional scanning peptide library consisting of 189 biotinylated-peptide libraries in individual kinase assays. Reaction products were bound to streptavidin coated membrane and after washing, phosphorylation was visualised by phosphorimaging. (B) Logo of LRRK2 phosphorylation site was derived from empirical data from (A) input into the enoLOGOS sequence logo tool. The height of the stack of single amino acid letters indicates the entropy of the site and the size of each letter indicates its preference at the position relative to the phosphorylation site between −5 and +4. The largest letters at each position in the logo were chosen to substitute for residues in a longer version of the LRRKtide substrate peptide to derive Nictide, shown below the logo. (C) GST fusion proteins with the indicated peptide sequences of LRRKtide, the longer LRRKtide, the carboxy terminus of moesin (500-577) and the Nictide substrates were subjected to phosphorylation by HEK293 purified LRRK2 (1326-2527) [G2019S] the indicated times. Reactions were stopped by the addition of sample buffer and products were subjected to SDS-PAGE. Gels were analysed by staining with colloidal blue (CB) and phosphorylation was monitored by autoradiography ($^{32}$P). Similar results were obtained in replicate experiments.
Figure 14B:
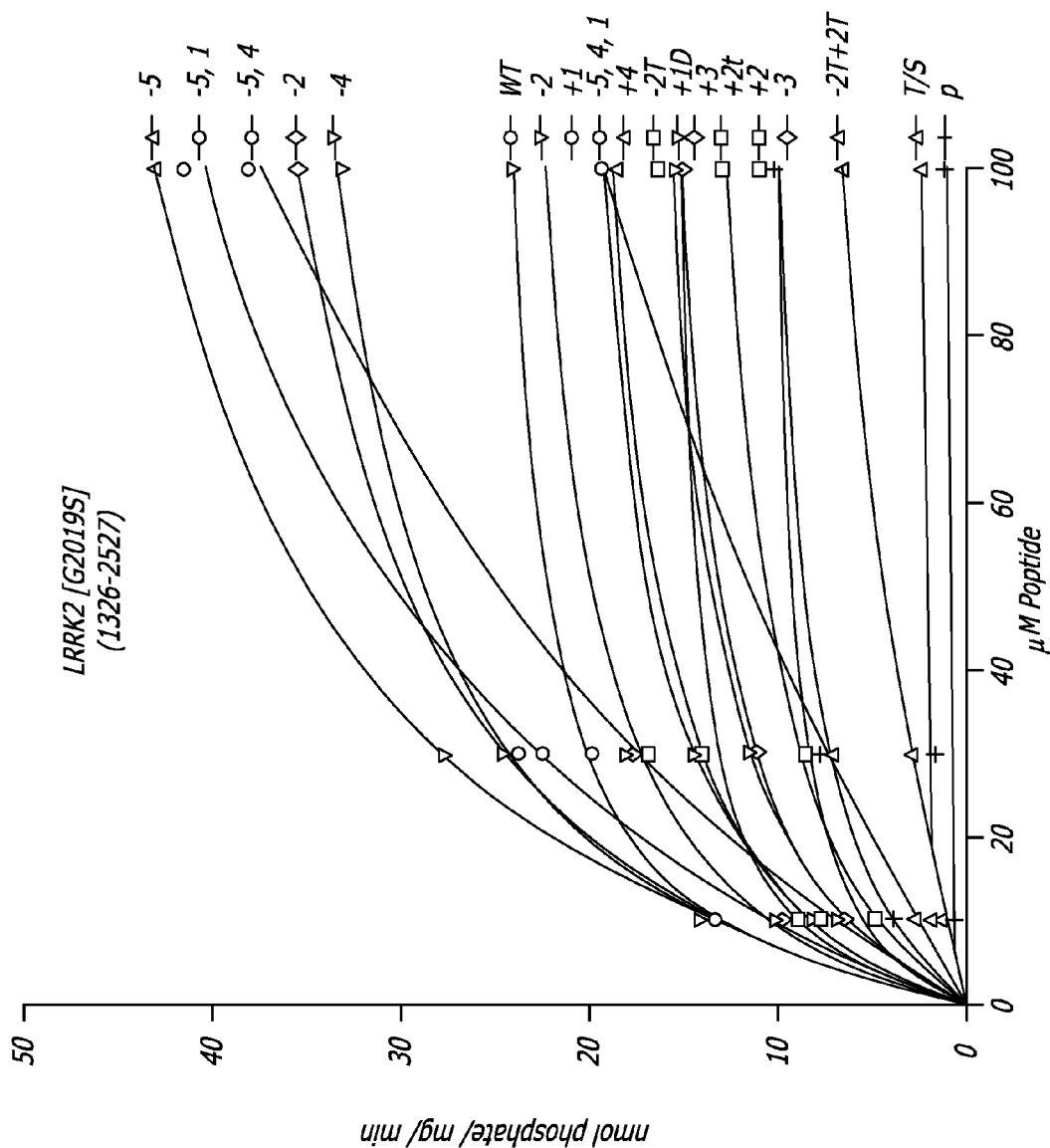
FIG. 14. Kinetic analysis of the Nictide Substrate. (A) Residues from −5 to +5 of the Nictide substrate (RLGWWRFYTLRRARQGNTKQR; SEQ ID NO:2) were mutated to the residue indicated in bold lettering. These peptides were analyzed for their ability to be phosphorylated by GST-LRRK2 1326-2527 [G2019S] or GST-LRRK2 1326-2527 [wild type] purified from HEK293 cells and Km and Vmax values were derived by nonlinear regression analysis as described in Materials and Methods. Similar results were obtained in at least three experiments. (B) Average values from a representative experiment from which data in A were derived for GST-LRRK2 1326-2527 [G2019S]. (C) As in (B) except with or GST-LRRK2 1326-2527 [wild type].
Figure 14C:
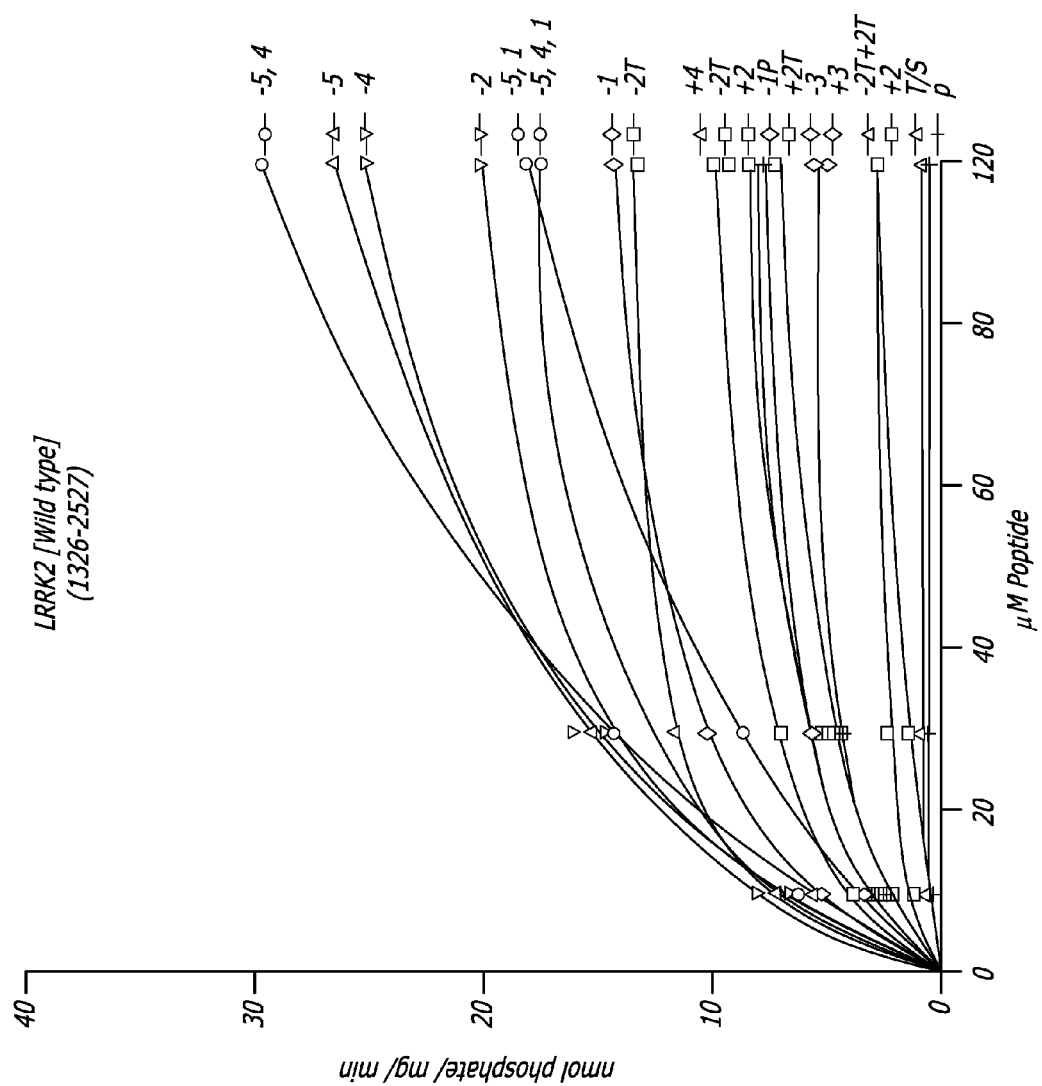

We next generated the synthetic Nictide peptide and found that it was phosphorylated by LRRK2[G2019S] with a $K_m$ of 10 μM (20-fold lower than LRRKtide) and $V_{max}$ of 26 U/mg (1.7-fold higher than LRRKtide). Nictide was phosphorylated by wild type LRRK2 with a similar $K_m$, but ~2-fold lower $V_{max}$, consistent with previous work showing that the Gly2019Ser mutation stimulates LRRK2 activity. We next studied the effects of mutating individual residues of Nictide on phosphorylation by LRRK2[G2019S] as well as wild type LRRK2 (FIG. 14). The mutations affected wild type LRRK2 and LRRK2[G2019S] similarly. Most mutations moderately affected $K_m$ values with the largest effect being the −5Trp to Ala mutation increasing the $K_m$ value 3-fold. Other mutations decreased the $V_{max}$ value of phosphorylation 2 to 5-fold (−4Trp to Ala and +2 Arg to Ala) (FIG. 14). Several mutations (−5Trp to Ala, −4Trp to Ala and −1 Tyr to Ala) increased $K_m$ values 2 to 3-fold, but enhanced $V_{max}$ of LRRK2 phosphorylation ~2-fold. We also combined the −5, −4 and −1 mutations that enhanced $V_{max}$ and found that although high $V_{max}$ values were maintained, the $K_m$ values were substantially increased 5 to 20-fold compared to Nictide. Interestingly, mutation of the Thr residue phosphorylated by LRRK2 to a Ser almost abolished phosphorylation of the peptide by LRRK2 (FIG. 14). Surprisingly, mutation of the +1Leu to a Pro residue, which would inhibit phosphorylation of most substrates by non-CMGC proline directed kinases, only decreased $V_{max}$ of LRRK2 phosphorylation under 2-fold without affecting $K_m$. This suggests that LRRK2 despite not belonging to the CMGC kinase family does have the potential to phosphorylate Ser/Thr residues followed by a Pro residue. The positional scanning peptide library data also indicated that there could be a preference of ra Thr residue at the −2 and +2 positions (FIG. 13A). As similar preferences for Thr at −2 and +2 positions has also been observed in other kinase scanning peptide library screens (Miller et al (2008) Linear motif atlas for phosphorylation-dependent signaling. Sci Signal 1, ra2), we decided to introduce THr at either −2 or +2 positions and found that this moderately increased the $K_m$ and reduced the $V_{max}$ value (FIG. 14). Introduction of Thr residues at both the −2 and +2 positions increased $K_m$ value of over 10-fold suggesting that Thr at these positions are not well tolerated.

To verify that substitution of residues in Nictide did not affect binding to P81 (phosphocellulose) paper, five different phosphorylated peptides were purified by HPLC and demonstrated that they all interractied with similar high efficiency with P81 paper (FIG. 19). Specifically, the peptides were phosphorylated with $^{32}$P-γATP at a concentration of 300 μM for LRRKtide and 100 μM for Nictide. Reactions were terminated by resuspension in 0.1% (v/v) trifluoracetic acid and passed through a $C_{18}$-SepPak column to remove the bulk of the $^{32}$P-γATP. The phosphopeptides were subsequently purified by reverse phase HPLC on a $C_{18}$ column. The major peak containing the 32P-phosphopeptides was pooled, lyophilized and resuspended in kinase buffer. The same amount of each peptide was applied to P81 paper in kinase and radioactivity applied was quantitated by Cerenkov counting. After extensive washing in 50 mM orthophasphoric acid, the percent of peptide remaining bound to P81 paper was quantitated by Cerenkov counting. Each measurement was undertaken in triplicate and the data shows the average percentage ±SEM peptide bound to P81 paper for each peptide.

An analysis of PD-associated mutations on phosphorylation of Nictide, compared to LRRKtide, was also conducted (FIG. 20). The wild type and mutations of GST-LRRK2 (residues 1326-2527) were purified and analyzed by SDS-PAGE on Novex 4-12% gels followed by colloidal blue staining (FIG. 20A). The same amounts of each form of LRRK2 were assayed against 200 µM LRRKtide or 30 µM Nictide for 5 min (FIG. 20B). Each measurement was undertaken in triplicate and the data shows the average percentage±SEM. Peptide phosphorylation is presented relative to wild type enzyme for each peptide. Similar results were obtained with two independent enzyme preparations. Using both peptides, similar results were obtained, names 1.5-2.0-fold elevated activity for LRRK2[G2019S] and 2.0-4.0-fold reduced activity for LRRK2[I2012T], LRRK2[I2020T] and LRRK2 [G2385R] (FIG. 20).

Figure 15A:
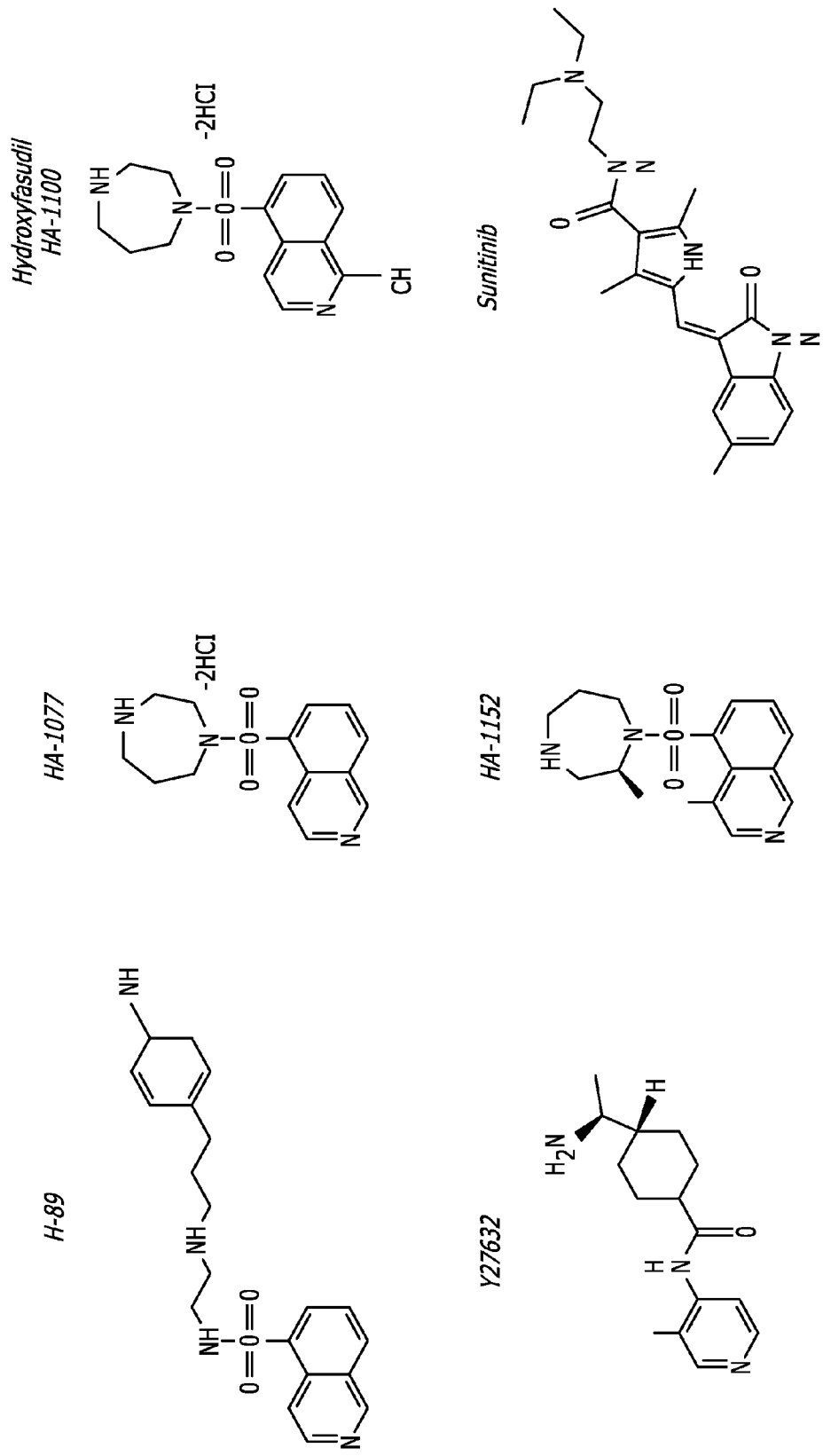
FIG. 15. Characterization of ROCK inhibitors as LRRK2 inhibitors. (A) Panels 1-8 show the chemical structures of the inhibitors utilized in this study. (B) LRRK2 1326-2527 [wild type] and [G2019S] and ROCK2 [2-543] were assayed in the presence or absence of the indicated concentration of the indicated inhibitor, in the presence of 100 µM ATP. The results are presented as percentage of kinase activity relative to the control measured in the presence of vehicle control. Results are the average of at least duplicate reactions where similar results were observed in at least one other experiment. The inhibitors are represented as follows: H89 by black line and circles; fasudil by grey line squares; hydroxyfasudil by grey line and triangles; Y-27632 by grey line and inverted triangles; H-1152 by grey diamonds; and sunitinib by grey triangles. (C) The IC50 values derived from the graphs in (B) are shown in µM and displayed in tabular format.
Figure 15B:
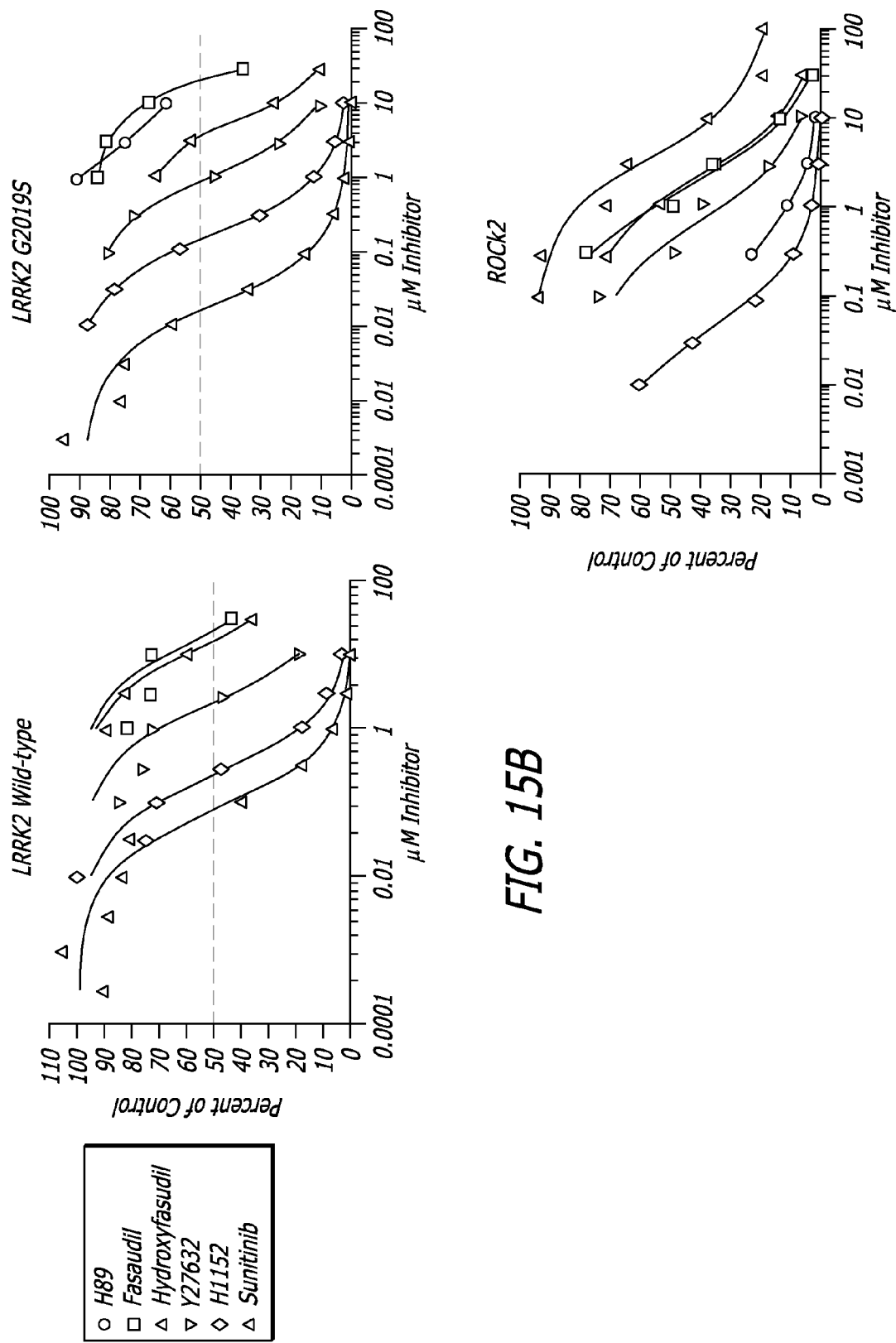

Identification of selective small molecule tool inhibitors of LRRK2. In the course of comparing the substrate specificity of LRRK2[G2019S] and ROCK2, we observed that several commonly deployed ROCK inhibitors (Y-27632, hydroxyfasudil, H-1152) also inhibited LRRK2[G2019S] (FIGS. 15A & B). Y-27632 inhibited LRRK2[G2019S] (IC50 1 µM) with similar potency to ROCK2 (IC50 0.7 µM). LRRK2[G2019S] was inhibited by hydroxyfasudil (IC50 6.8 µM) and H-1152 (IC50 0.15 µM) ~3-fold more weakly than ROCK (FIG. 15B). H-1152 and hydroxyfasudil belong to a well-studied series of isoquinolinesulfonamides [26] whilst Y-27632 is structurally unrelated (FIG. 15A). Other isoquinolinesulfonamides reported to inhibit ROCK namely H89 and fasudil only inhibited LRRK2[G2019S] weakly (FIG. 15B). We confirmed that structurally unrelated sunitinib, inhibited LRRK2 with similar potency (IC50~19 nM) to previous reports, but in contrast to Y-27632 and H-1152, sunitinib only weakly inhibited ROCK (IC50~3700 nM). Comparing the potency of H-1152, Y-27632 and sunitinib for LRRK2[G2019S] and wild type LRRK2, we observed that wild type LRRK2 was moderately less sensitive to these drugs than the activated mutant. The IC50 of inhibition of wild type LRRK2 was increased 2-fold for H-1152 and Y-27632 and 4-fold for sunitinib (FIG. 15B).

LRRK2 tool compound selectivity profiles. To compare the relative selectivity profiles of Y-27632, H-1152 and fasudil (HA-1077) with sunitinib, we profiled these inhibitors against a panel of 85 protein kinases at ATP concentrations, which approximate the $K_m$ constant for ATP (Table 1). This revealed that Y-27632 is selective, and at 10 µM in addition to inhibiting ROCK2 only suppressed activity of PRK2 and MNK1 over 5-fold. H-1152 (1 µM) in addition to ROCK, inhibited Aurora B and BRSK2 over 5-fold. Fasudil, hydroxyfasudil and sunitinib were less selective. Fasudil (10 µM) inhibited RSK1, S6K1, PRK2, MSK1, MNK1, MELK, MSK1, MELK over 5-fold. Hydroxyfasudil (10 µM) inhibited RSK1, S6K1, PRK2, MSK1. Sunitinib (1 µM)

Figures 15C, 16A, 16B:
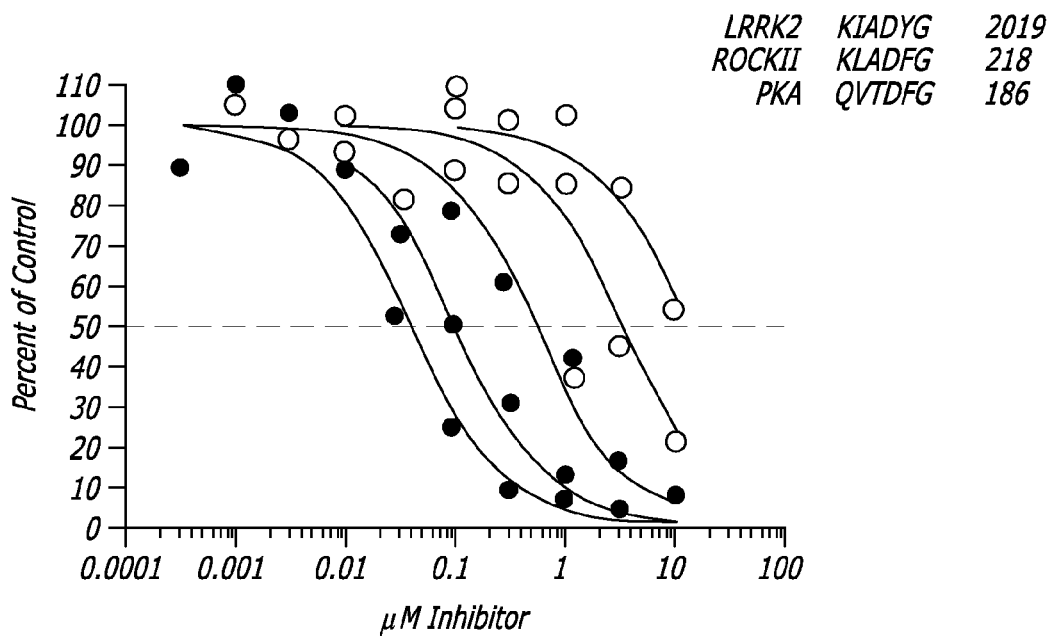
FIG. 16. Design of an LRRK2 inhibitor desensitized mutant. (A) Sequence alignment of the amino acids surrounding the Asp of subdomain VII for LRRK2, Protein Kinase A (PKA) and ROCK2. Identical amino acids are shaded in black and similar amino acids are shaded in grey. Terminal amino acid residues are numbered. (B) LRRK2 (1326-2527) [G2019S] and LRRK2 (1326-2527) [G2019S/A2016T] were assayed in the presence or absence of the indicated concentration of the inhibitor, in the presence of 100 µM ATP and expressed as a percent of control reactions performed in the presence of vehicle alone. LRRK2 (1326-2527) [G2019S] reactions are represented by filled circles and LRRK2 (1326-2527) [G2019S/A2016T] reactions are represented by open circles. Colour scheme is the same as in FIG. 15B.

Development of inhibitor resistant mutants. Previous work has shown that the Ala215 residue on ROCK plays an important role in controlling the specificity of interaction with H-1152 by forming two van der Waals interactions with H-1152. In the case of LRRK2, the residue equivalent to Ala215 is Ala2016 (FIG. 16A). This residue in both LRRK2 and ROCK1 lies just prior to the subdomain VII-DFG motif. PKA is inhibited ~50-fold more weakly by H-1152, and has Thr183 in the equivalent position. Mutation of Thr183 to Ala in PKA did not affect basal activity, but enhanced its inhibition by H-1152 four-fold. We therefore mutated Ala2016 in LRRK2 to a Thr residue and found that this did not inhibit LRRK2 [G2019S] basal activity, but increased the IC50 of inhibition by H-1152 ~20-fold (FIG. 16B). We also observed that the LRRK2 [A2016T] mutant was 13 and ~12-fold more resistant to inhibition by Y-27632 and sunitinib, respectively (FIG. 16B). In the LRRK2[A2016T] mutant the T2016 side chain would clash with these atoms of H-1152, probably forcing it to bind in a rotated and less favorable orientation in the ATP-site. This is the likely explanation of its reduced activity against the mutant compared to the wild-type LRRK2. We also mutated Ala2016 to other residues but found that these mutations markedly inhibited intrinsic LRRK2 activity (data not shown).

Evaluation of ROCK and LRRK2 inhibitors in cells. We next investigated the effect that sunitinib, H-1152 and Y-27632 had on phosphorylation of MYPT and ERM proteins in HEK 293 cells. We observed significant basal phosphorylation of MYPT at Thr850 and ERM proteins at site(s) equivalent to Thr567 on ezrin (FIG. 17A). In order to activate ROCK we induced stable expression of a constitutively activated G14V-Rho mutant which increased phosphorylation of both MYPT and ezrin ~3-fold (FIG. 17A). Treatment of cells with 10 µM sunitinib did not ablate phosphorylation of MYPT at Thr850 to a similar extent to H-1152 and Y-27632, consistent with ROCK mediating this phosphorylation. However, in the same extracts neither sunitinib, H-1152 nor Y-27632 inhibited ERM protein phosphorylation either in the presence or absence of G14V-Rho (FIG. 17A).

Figure 18:
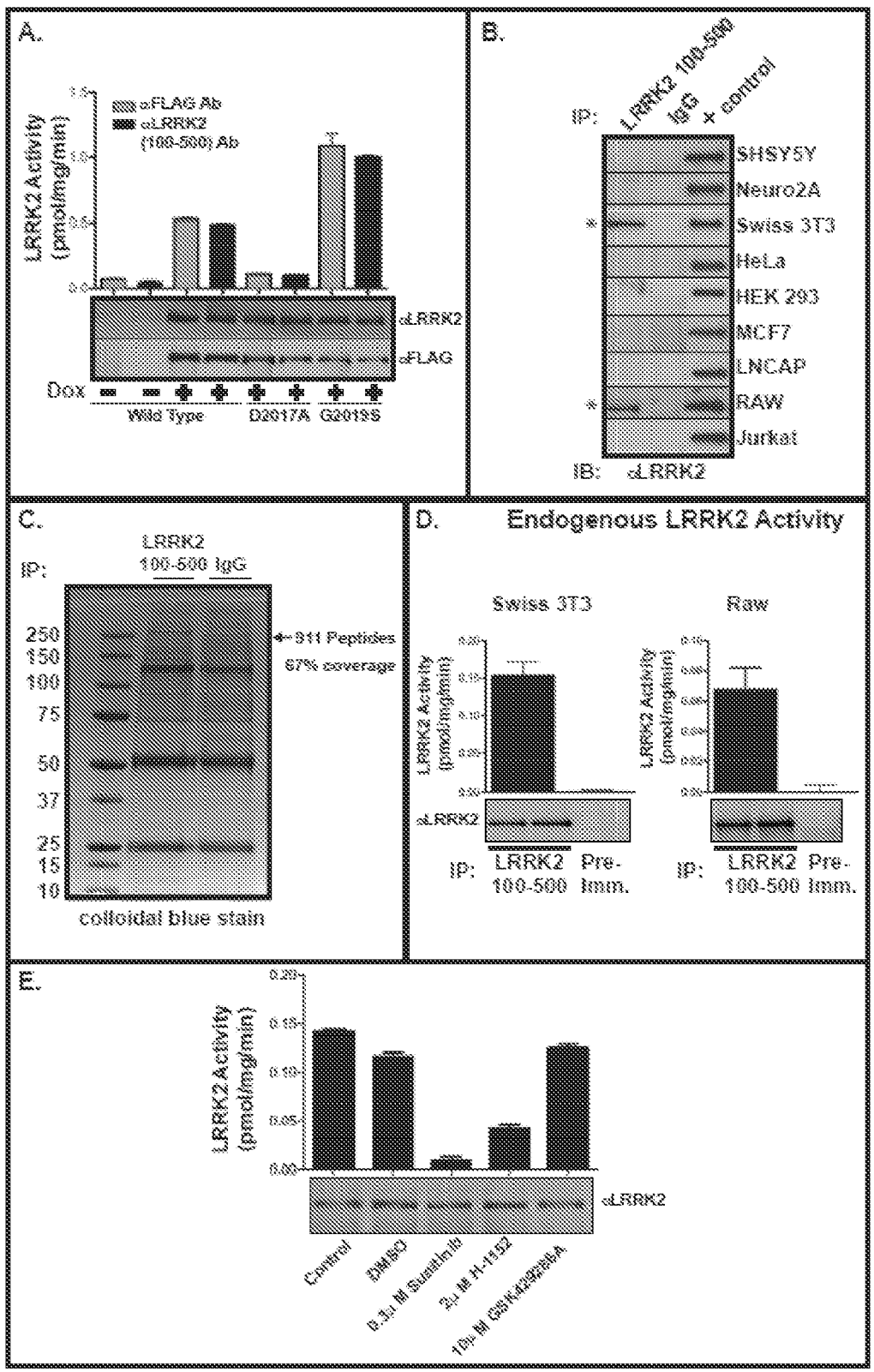
FIG. 18. Analysis of Endogenous LRRK2 (A) Doxycycline inducible HEK 293 cells overexpressing full length flag-tagged human LRRK2 and LRRK2 containing D2017A and G2019S mutations were generated as described in material and methods. Anti-LRRK2 [100-500] S348C antibody was used to retrieve recombinant protein. Precipitates were assayed for kinase activity using LRRKtide and were immunoblotted with anti-FLAG and S374C anti-LRRK2 (B)

Immunoprecipitation and assay of endogenous LRRK2. In order to measure protein kinase activity of endogenous LRRK2 (which to our knowledge has previously not been achieved), we generated numerous LRRK2 antibodies and evaluated their ability to immunoprecipitate and immunoblot recombinant full length Flag-LRRK2. This revealed that the antibody raised against a fragment of LRRK2 encompassing amino acids 100-500 immunoprecipitated and immunoblotted Flag-LRRK2 with similar efficiency as anti-Flag antibody (FIG. 18A). Moreover, overexpressed FLAG-LRRK2 was immunoprecipitated with the LRRK2 [100-500] antibody and possessed similar activity to enzyme immunoprecipitated with Flag-antibody, indicating that the LRRK2 [100-500] antibody is not inhibiting LRRK2 protein kinase activity (FIG. 18A). We next attempted to immunoprecipitate endogenous LRRK2 from extracts derived from a panel of cell lines using the LRRK2 [100-500] antibody. This revealed that Swiss3T3 fibroblasts and RAW macrophages express detectable levels of endogenous LRRK2 protein (FIG. 18B). The LRRK2 [100-500] immunoprecipitates derived from Swiss-3T3 cells were subjected to electrophoresis on a polyacrylamide gel. Staining with Colloidal blue revealed a protein migrating with a molecular weight of ~280 kDa which was confirmed to comprise LRRK2 by mass spectroscopy analysis (FIG. 18C). We next subjected LRRK2 and control immunoprecipitates derived from Swiss 3T3 and Raw cells to protein kinase assays employing Nictide as a substrate. This revealed significant protein activity with LRRK2 immunoprecipitates, but not with the control immunoprecipitate. Moreover, the protein kinase activity detected in the LRRK2 immunoprecipitate was suppressed by H-1152 and sunitinib.

Discussion

Figure 12:
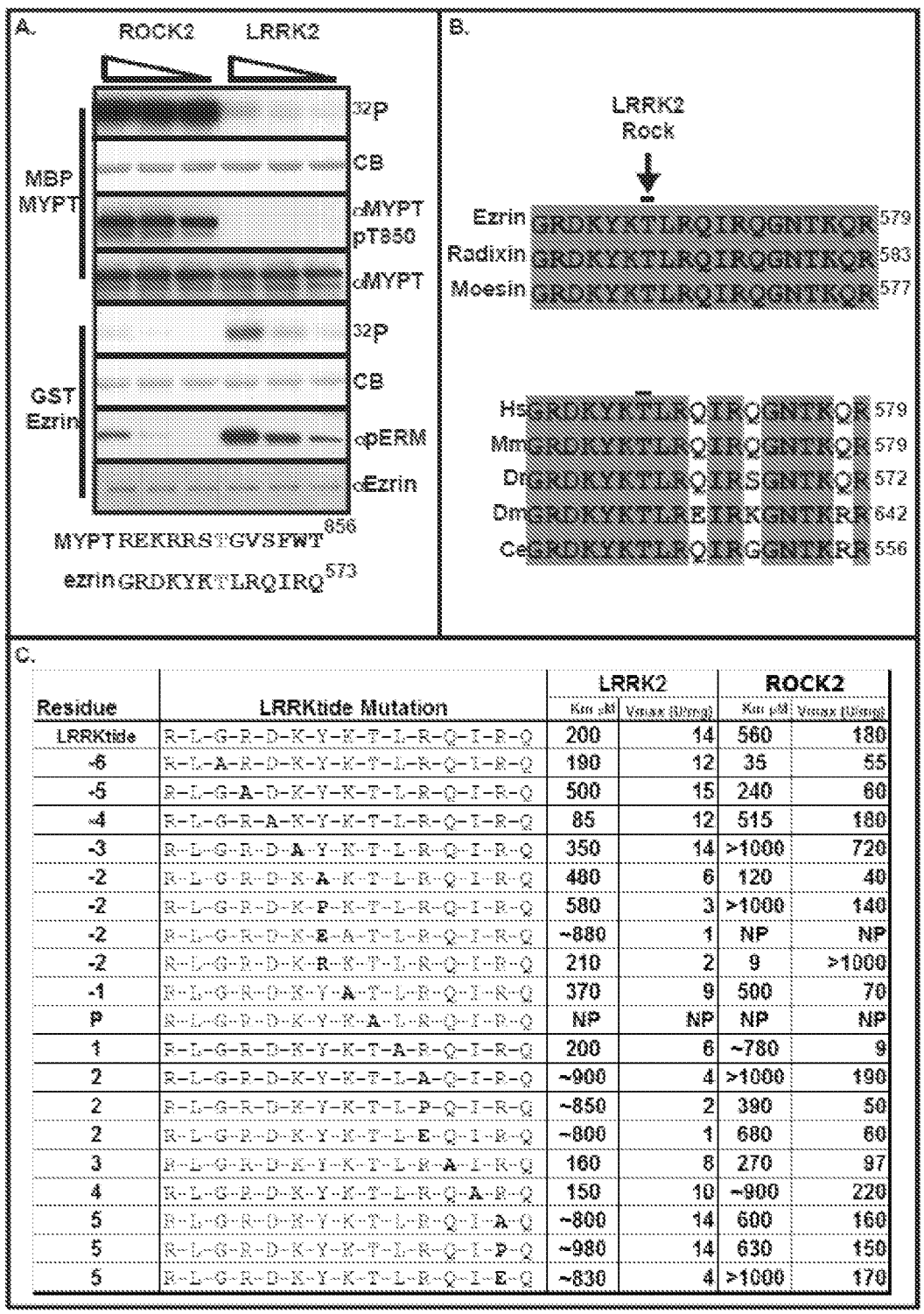
FIG. 12 Comparison of ROCK substrates as substrates for LRRK2 (A-upper panel) ROCK2 [2-543] and LRRK2 [1326-2527] were diluted to a concentration where they possessed identical activity towards LRRKtide and then incubated with 2 µM MBP-MYPT [714-1004] or heat treated GST-Ezrin [full-length] in the presence of Mg[γ-$^{32}$P]-ATP. Enzyme was decreased successively two fold, represented by decreasing slope in triangle. Reactions were terminated after 15 min by addition of sample buffer and products were subjected to SDS-PAGE. Gels were analysed by staining with colloidal blue (CB) and phosphorylation was monitored by autoradiography. Immunoblotting analysis was also undertaken with the indicated antibodies. (A-lower panel) Comparison of the amino acid sequences surrounding Thr850-MYPT and Thr567-ezrin showing little similarity between peptides. (B) Sequence alignments of the indicated species of ERM proteins surrounding the ROCK/LRRK2 phosphorylation site. Identical residues are shaded. The accession sequences used were: human moesin [accession no. NP_002435] human ezrin [accession no. NP_03370] human radixin [accession no. NP_002897]. *Mus musculus* [accession no. NP_034963], *Danio rerio* [accession no. NP_001004296], *Drosophila melanogaster* (Dm) [accession no. NP_727290], *Caenorhabditis elegans* (Ce) [accession no. NP491550]. (C) Analysis of substrate recognition determinants in LRRKtide. Residues from −6 to −5 of the LRRKtide substrate (RLGRDKYKTLRQIRQ; SEQ ID NO:1) were mutated to the residue indicated in bold lettering. These peptides were analyzed for their ability to be phosphorylated by GSTLRRK2 1326-2527 [G2019S] purified from HEK293 cells or ROCK2 (amino acids 2-543) purified from baculovirus. NP denotes that the peptide was phosphorylated so poorly that kinetic analysis was not feasible. For $K_m$ values above 500 µm an "~" sign is added to stress that these values were inferred from kinetic analysis undertaken at peptide concentrations of lower than 1 mM. Similar results were obtained in at least two experiments.
Figure 13C:
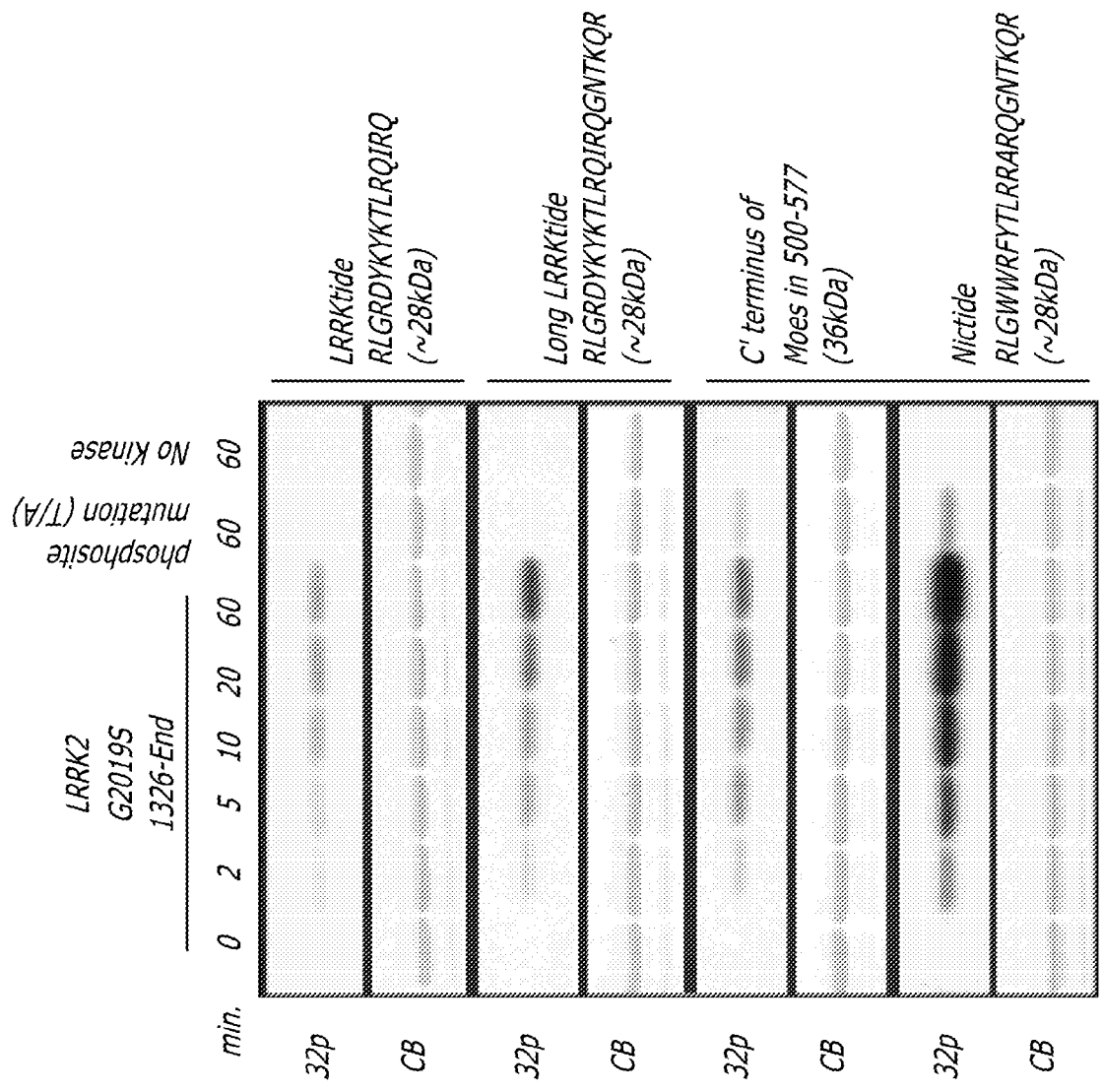

Our data reveal that LRRK2 tolerates a wider range of amino acids in its substrates compared to some other protein kinases that have strong requirements for specific amino acids within the substrates that they phosphorylate (FIGS. 12 and 13). Significant substrate specificity preferences are −5(Trp, Arg), −2(Phe, Tyr, His), −1(Tyr, Arg, Trp), +2 (Arg) and +3 (Arg) positions. Importantly, or data suggest that LRRK2 has a strong preference for phosphorylating Thr, as mutation of the phosphorylated Thr residue in Nictide to Ser virtually abolished phosphorylation of the peptide by LRRK2 (FIG. 14). Positional scanning peptide library analysis also suggested that LRRK2 poorly tolerated acidic Glu or Asp residues at all positions surrounding the phosphorylation site (FIG. 13A). LRRKtide only possesses a single acidic residue (−4Asp), and the only mutation we tested that improved LRRK2 phosphorylation, was mutation of this residue to Ala (FIG. 12C). It is possible that this knowledge of substrate specificity of LRRK2 may aid in the identification of LRRK2 substrates and/or potential phosphorylation sites within identified substrates. This analysis has also enabled us to generate the Nictide peptide, a much improved substrate compared to LRRKtide peptide that is widely deployed to assay LRRK2. A key advantage of Nictide is that it can be used at much lower concentrations in kinases assays. We have been able to assay the activity of endogenous LRRK2 using Nictide, with virtually no background activity observed in the control immunoprecipitate (FIG. 18E). To our knowledge this is the first time that activity of endogenous LRRK2 has been assessed. When trying to assay activity of endogenous LRRK2 employing LRRKtide at concentrations of 300 μM ($K_m$ value), we observed significant background activity in the pre-immune immunoprecipitation (ND data not shown). Assessment of activity of endogenous LRRK2 is important, as it paves the way to study LRRK2 activity in cells/tissues derived from PD patients. It will enable evaluation of whether LRRK2 protein kinase activity is controlled by extracellular agonists and may also help in the screening for inhibitors for LRRK2. We also observed that fusing Nictide to GST, yielded a highly expressed protein in E. coli (4 mg/liter) which was efficiently phosphorylated by LRRK2 in vitro at a greater initial rate than GSTezrin [505-586] or GST-LRRKtide (FIG. 13C). GST-Nictide would serve as a good positive control when evaluating efficiency of phosphorylation of LRRK2 substrates that are identified in future studies.

Our analysis reveals that the substrate specificity of LRRK2 is quite distinct from ROCK2. LRRK2 does not phosphorylate MYPT and ROCK2 poorly phosphorylates ezrin. Moreover, mutations in LRRKtide affected phosphorylation by LRRK2 and ROCK2 in different ways. For example, mutation of the +1 position of the LRRKtide peptide from a Leu to Ala abolished ROCK phosphorylation, without affecting LRRK2 phosphorylation. Many LRRKtide mutations enhanced phosphorylation by ROCK but inhibited phosphorylation by LRRK2. Consistent with ROCK2 phosphorylating ezrin poorly in vitro, we also found that in vivo various ROCK inhibitors failed to inhibit ERM phosphorylation under conditions which they suppressed MYPT phosphorylation. This is consistent with other studies where the Y-27632 ROCK inhibitor was found not to suppress ERM phosphorylation. Taken together this data casts doubt on earlier suggestions that ERM proteins are physiologically phosphorylated by ROCK isoforms. The finding that the H-1152, Y-27632 and sunitinib failed to suppress ERM phosphorylation indicates that either LRRK2 does not phosphorylate ERM in 293 cells or that LRRK2 is not the sole kinase that phosphorylates ERM proteins. As we were unable to detect significant levels of endogenous LRRK2 in 293 cells (FIG. 18), we overexpressed LRRK2 and LRRK2 [G2019S] in 293 cells, but this also failed to induce phosphorylation of ERM proteins (data not shown). Taken together, this suggests that although ERM proteins are efficiently phosphorylated by LRRK2 in vitro, there is no strong evidence that ERM proteins comprise physiological substrates for LRRK2. Recent studies in Drosophila and primary mouse lymphocytes have suggested that the SILK/LOK STE20 protein kinase might be a key player in controlling ERM phosphorylation. Consistent with this, ERM phosphorylation is reduced but not abolished in lymphocytes derived from SLK/LOK knockout mice. It was shown in 1994 that SILK has an optimal motif of R-R/K-F-G-S/T-L-R-R-F/I, which fits pretty well for the ERM site D-K-Y-K-T-L-R-Q-I and is also remarkably similar to the optimal substrate specificity of LRRK2, W-R-F-Y-T-L-R-R-A. It would also be interesting to test whether residual ERM phosphorylation observed in the SLK/LOK knockout cells was further reduced by treatment with sunitinib and Y-27632 LRRK2 inhibitors. Another recent study has indicated that another STE20 family kinase termed Mst4 kinase can phosphorylate ezrin in polarised epithelial cells in a pathway controlled by the LKB1 tumour suppressor. MST4 was present in our kinase profiling panel and was not inhibited by H-1152, Y-27632 or sunitinib (Table 1).

The finding that widely utilised ROCK inhibitors Y-27632 (used in >1400 papers) as well as H-1152 and hydroxyfasudil inhibit recombinant as well as endogenous LRRK2 with similar potency to that which they target ROCK2 was unexpected, as LRRK2 and ROCK2 are not closely related kinases. LRRK lies within the tyrosine-like kinases of the human kinome whilst ROCK2 belongs to the distinct AGC branch. It is therefore possible that some of the physiological effects observed with these ROCK inhibitors could result from inhibition of LRRK2 rather than ROCK isoforms. The finding that the LRRK2 [G2019S] mutant was 2 to 4-fold more sensitive H-1152, Y-27632 and sunitinib than the wild type LRRK2, also indicates that it may be possible to develop compounds that have greater potency towards the Parkinson's disease mutant. It has also been reported that the LRRK2 [G2019S] and LRRK2[I2020T] mutants that possess elevated activity were also moderately more sensitive to a panel of non-selective kinase inhibitors. If compounds that specifically inhibited Parkinson's disease mutant forms of LRRK2 could be elaborated, they might have lower side effects and not suppress the normal functions of wild type LRRK2. In drug discovery screens being undertaken to identify LRRK2 inhibitors, it could be beneficial to screen compounds against both mutant and wild type forms of LRRK2. Molecular modelling of the kinase domain of LRRK2 and comparing it with the structures of other kinases revealed a model of how LRRK2 might interact with H-1152. Several residues in the active site of ROCK that are key for binding to H-1152 are also conserved in LRRK2. These include Ala2016, the equivalent of Ala215 in ROCK2 that plays an important role in mediating binding to the inhibitor. Mutation of Ala2016 in LRRK2 to a Thr residue, equivalent to Thr182 in PKA that is weakly inhibited by H-1152, did not affect the basal LRRK2 activity, but markedly suppressed inhibition of LRRK2 by H-1152 and other ROCK kinase inhibitors. The inhibitor resistant LRRK2 [A2016T] mutant might aid in exploring the physiological roles of LRRK2. The wild type and the LRRK2 [A2016T] mutant could be overexpressed in cells and phosphorylation of any target should be less sensitive to inhibition by H-1152, Y-27632 or sunitinib in the cells overexpressing the drug resistant mutant.

Our findings also provide a pharmacological strategy in which phosphorylation of identified LRRK2 substrates could be validated. We suggest that phosphorylation of a LRRK2 substrate should be suppressed by Y-27632 and H-1152 (dual ROCK and LRRK2 inhibitors) as well as sunitinib (inhibits LRRK2 but not ROCK). In contrast, ROCK mediated processes should be sensitive to Y-27632 and H-1152, but should not be inhibited by sunitinib. Consistent with this, sunitinib does not inhibit the phosphorylation of MYPT at Thr850 under conditions where this phosphorylation is inhibited by Y-27632 and H-1152 (FIG. 17).

In conclusion, we have undertaken some basic analysis of the LRRK2 substrate specificity and developed improved assays to isolate and assess its activity. This will aid in assessing how LRRK2 is regulated and might also facilitate identification of LRRK2 inhibitors that might have potential for treatment of Parkinson's disease. We have also developed a strategy making use of Y-276332 or H-1152 and sunitinib to explore the roles of the LRRK2 kinase.

EXAMPLE 5

GST-Nictide

GST-Nictide and a plasmid useful in expressing GST-Nictide, as used in the preceding examples, are shown below.

| | |
|---|---|
| Plasmid Name | GEX6-LRKK2-TIDE (nic-tide) |
| Protein | GST-LRKK2-TIDE |
| Species | Artificial |
| Parental plasmid | Gex6-P1 |
| Insert Source | |
| Restriction sites used | Bamh1-Not1 |
| Protein sequence<br>GST italic<br>Precision site bold<br>Peptide underlined | MSPILGYWKIKGLVQPTRLLLEYLEEKYEEHLYERDEGDK<br>WRNKKFELGLEFPNLPYYIDGDVKLTQSMAIIRYIADKHN<br>MLGGCPKERAEISMLEGAVLDIRYGVSRIAYSKDFETLKV<br>DFLSKLPEMLKMFEDRLCHKTYLNGDHVTHPDFMLYDALD<br>VVLYMDPMCLDAFPKLVCFKKRIEAIPQIDKYLKSSKYIA<br>WPLQGWQATFGGGDHPPKSD*LEVLFQGPLGS*<u>RLGWWRFYT</u><br><u>LRRARQGNTKQR</u><br>(SEQ ID NO: 72) |
| DNA sequence of<br>GST-nictide | ATGTCCCCTATACTAGGTTATTGGAAAATTAAGGGCCTTG<br>TGCAACCCACTCGACTTCTTTTGGAATATCTTGAAGAAAA<br>ATATGAAGAGCATTTGTATGAGCGCGATGAAGGTGATAAA<br>TGGCGAAACAAAAAGTTTGAATTGGGTTTGGAGTTTCCCA<br>ATCTTCCTTATTATATTGATGGTGATGTTAAATTAACACA<br>GTCTATGGCCATCATACGTTATATAGCTGACAAGCACAAC<br>ATGTTGGGTGGTTGTCCAAAAGAGCGTGCAGAGATTTCAA<br>TGCTTGAAGGAGCGGTTTTGGATATTAGATACGGTGTTTC<br>GAGAATTGCATATAGTAAAGACTTTGAAACTCTCAAAGTT<br>GATTTTCTTAGCAAGCTACCTGAAATGCTGAAAATGTTCG<br>AAGATCGTTTATGTCATAAAACATATTTAAATG GTGATC<br>ATGTAACCCATCCTGACTTCATGTTGTATGACGCTCTTGA<br>TGTTGTTTTATACATGGACCCAATGTGCCTGGATGCGTTC<br>CCAAAATTAGTTTGTTTTAAAAAACGTATTGAAGCTATCC<br>CACAAATTGATAAGTACTTGAAATCCAGCAAGTATATAGC<br>ATGGCCTTTGCAGGGCTGGCAAGCCACGTTTGGTGGTGGC<br>GACCATCCTCCAAAATCGGATCTGGAAGTTCTGTTCCAGG<br>GGCCCCTGGGATCCAGACTAGGTTGGTGGAGATTTTATAC<br>ACTACGACGGGCCAGGCAGGGCAATACAAAGCAGAGATAG<br>CGGCCGC<br>SEQ ID NO: 73 |
| DNA sequence of the<br>Gex6-GST-Nictide<br>vector | ACGTTATCGACTGCACGGTGCACCAATGCTTCTGGCGTCA<br>GGCAGCCATCGGAAGCTGTGGTATGGCTGTGCAGGTCGTA<br>AATCACTGCATAATTCGTGTCGCTCAAGGCGCACTCCCGT<br>TCTGGATAATGTTTTTTGCGCCGACATCATAACGGTTCTG<br>GCAAATATTCTGAAATGAGCTGTTGACAATTAATCATCGG<br>CTCGTATAATGTGTGGAATTGTGAGCGGATAACAATTTCA<br>CACAGGAAACAGTATTCATGTCCCCTATACTAGGTTATTG<br>GAAAATTAAGGGCCTTGTGCAACCCACTCGACTTCTTTTG<br>GAATATCTTGAAGAAAATATGAAGAGCATTTGTATGAGC<br>GCGATGAAGGTGATAAATGGCGAAACAAAAAGTTTGAATT<br>GGGTTTGGAGTTTCCCAATCTTCCTTATTATATTGATGGT<br>GATGTTAAATTAACACAGTCTATGGCCATCATACGTTATA<br>TAGCTGACAAGCACAACATGTTGGGTGGTTGTCCAAAAGA<br>GCGTGCAGAGATTTCAATGCTTGAAGGAGCGGTTTTGGAT<br>ATTAGATACGGTGTTTCGAGAATTGCATATAGTAAAGACT<br>TTGAAACTCTCAAAGTTGATTTTCTTAGCAAGCTACCTGA<br>AATGCTGAAAATGTTCGAAGATCGTTTATGTCATAAAACA<br>TATTTAAATGGTGATCATGTAACCCATCCTGACTTCATGT<br>TGTATGACGCTCTTGATGTTGTTTTATACATGGACCCAAT<br>GTGCCTGGATGCGTTCCCAAAATTAGTTTGTTTTAAAAAA<br>CGTATTGAAGCTATCCCACAAATTGATAAGTACTTGAAAT<br>CCAGCAAGTATATAGCATGGCCTTTGCAGGGCTGGCAAGC |

-continued
CACGTTTGGTGGTGGCGACCATCCTCCAAAATCGGATCTG
GAAGTTCTGTTCCAGGGGCCCCTGGGATCCAGACTAGGTT
GGTGGAGATTTTATACACTACGACGGGCCAGGCAGGGCAA
TACAAAGCAGAGATAGCGGCCGCATCGTGACTGACTGACG
ATCTGCCTCGCGCGTTTCGGTGATGACGGTGAAAACCTCT
GACACATGCAGCTCCCGGAGACGGTCACAGCTTGTCTGTA
AGCGGATGCCGGGAGCAGACAAGCCCGTCAGGGCGCGTCA
GCGGGTGTTGGCGGGTGTCGGGGCGCAGCCATGACCCAGT
CACGTAGCGATAGCGGAGTGTATAATTCTTGAAGACGAAA
GGGCCTCGTGATACGCCTATTTTTATAGGTTAATGTCATG
ATAATAATGGTTTCTTAGACGTCAGGTGGCACTTTTCGGG
GAAATGTGCGCGGAACCCCTATTTGTTTATTTTTCTAAAT
ACATTCAAATATGTATCCGCTCATGAGACAATAACCCTGA
TAAATGCTTCAATAATATTGAAAAAGGAAGAGTATGAGTA
TTCAACATTTCCGTGTCGCCCTTATTCCCTTTTTTGCGGC
ATTTTGCCTTCCTGTTTTTGCTCACCCAGAAACGCTGGTG
AAAGTAAAAGATGCTGAAGATCAGTTGGGTGCACGAGTGG
GTTACATCGAACTGGATCTCAACAGCGGTAAGATCCTTGA
GAGTTTTCGCCCCGAAGAACGTTTTCCAATGATGAGCACT
TTTAAAGTTCTGCTATGTGGCGCGGTATTATCCCGTGTTG
ACGCCGGGCAAGAGCAACTCGGTCGCCGCATACACTATTC
TCAGAATGACTTGGTTGAGTACTCACCAGTCACAGAAAAG
CATCTTACGGATGGCATGACAGTAAGAGAATTATGCAGTG
CTGCCATAACCATGAGTGATAACACTGCGGCCAACTTACT
TCTGACAACGATCGGAGGACCGAAGGAGCTAACCGCTTTT
TTGCACAACATGGGGGATCATGTAACTCGCCTTGATCGTT
GGGAACCGGAGCTGAATGAAGCCATACCAAACGACGAGCG
TGACACCACGATGCCTGCAGCAATGGCAACAACGTTGCGC
AAACTATTAACTGGCGAACTACTTACTCTAGCTTCCCGGC
AACAATTAATAGACTGGATGGAGGCGGATAAAGTTGCAGG
ACCACTTCTGCGCTCGGCCCTTCCGGCTGGCTGGTTTATT
GCTGATAAATCTGGAGCCGGTGAGCGTGGGTCTCGCGGTA
TCATTGCAGCACTGGGGCCAGATGGTAAGCCCTCCCGTAT
CGTAGTTATCTACACGACGGGGAGTCAGGCAACTATGGAT
GAACGAAATAGACAGATCGCTGAGATAGGTGCCTCACTGA
TTAAGCATTGGTAACTGTCAGACCAAGTTTACTCATATAT
ACTTTAGATTGATTTAAAACTTCATTTTTAATTTAAAAGG
ATCTAGGTGAAGATCCTTTTTGATAATCTCATGACCAAAA
TCCCTTAACGTGAGTTTTCGTTCCACTGAGCGTCAGACCC
CGTAGAAAAGATCAAAGGATCTTCTTGAGATCCTTTTTTT
CTGCGCGTAATCTGCTGCTTGCAAACAAAAAAACCACCGC
TACCAGCGGTGGTTTGTTTGCCGGATCAAGAGCTACCAAC
TCTTTTTCCGAAGGTAACTGGCTTCAGCAGAGCGCAGATA
CCAAATACTGTCCTTCTAGTGTAGCCGTAGTTAGGCCACC
ACTTCAAGAACTCTGTAGCACCGCCTACATACCTCGCTCT
GCTAATCCTGTTACCAGTGGCTGCTGCCAGTGGCGATAAG
TCGTGTCTTACCGGGTTGGACTCAAGACGATAGTTACCGG
ATAAGGCGCAGCGGTCGGGCTGAACGGGGGGTTCGTGCAC
ACAGCCCAGCTTGGAGCGAACGACCTACACCGAACTGAGA
TACCTACAGCGTGAGCTATGAGAAAGCGCCACGCTTCCCG
AAGGGAGAAAGGCGGACAGGTATCCGGTAAGCGGCAGGGT
CGGAACAGGAGAGCGCACGAGGGAGCTTCCAGGGGGAAAC
GCCTGGTATCTTTATAGTCCTGTCGGGTTTCGCCACCTCT
GACTTGAGCGTCGATTTTTGTGATGCTCGTCAGGGGGGCG
GAGCCTATGGAAAAACGCCAGCAACGCGGCCTTTTTACGG
TTCCTGGCCTTTTGCTGGCCTTTTGCTCACATGTTCTTTC
CTGCGTTATCCCCTGATTCTGTGGATAACCGTATTACCGC
CTTTGAGTGAGCTGATACCGCTCGCCGCAGCCGAACGACC
GAGCGCAGCGAGTCAGTGAGCGAGGAAGCGGAAGAGCGCC
TGATGCGGTATTTTCTCCTTACGCATCTGTGCGGTATTTC
ACACCGCATAAATTCCGACACCATCGAATGGTGCAAAACC
TTTCGCGGTATGGCATGATAGCGCCCGGAAGAGAGTCAAT
TCAGGGTGGTGAATGTGAAACCAGTAACGTTATACGATGT
CGCAGAGTATGCCGGTGTCTCTTATCAGACCGTTTCCCGC
GTGGTGAACCAGGCCAGCCACGTTTCTGCGAAAACGCGGG
AAAAAGTGGAAGCGGCGATGGCGGAGCTGAATTACATTCC
CAACCGCGTGGCACAACAACTGGCGGGCAAACAGTCGTTG
CTGATTGGCGTTGCCACCTCCAGTCTGGCCCTGCACGCGC
CGTCGCAAATTGTCGCGGCGATTAAATCTCGCGCCGATCA
ACTGGGTGCCAGCGTGGTGGTGTCGATGGTAGAACGAAGC
GGCGTCGAAGCCTGTAAAGCGGCGGTGCACAATCTTCTCG
CGCAACGCGTCAGTGGGCTGATCATTAACTATCCGCTGGA
TGACCAGGATGCCATTGCTGTGGAAGCTGCCTGCACTAAT
GTTCCGGCGTTATTTCTTGATGTCTCTGACCAGACACCCA
TCAACAGTATTATTTTCTCCCATGAAGACGGTACGCGACT
GGGCGTGGAGCATCTGGTCGCATTGGGTCACCAGCAAATC
GCGCTGTTAGCGGGCCCATTAAGTTCTGTCTCGGCGCGTC
TGCGTCTGGCTGGCTGGCATAAATATCTCACTCGCAATCA
AATTCAGCCGATAGCGGAACGGGAAGGCGACTGGAGTGCC
ATGTCCGGTTTTCAACAAACCATGCAAATGCTGAATGAGG
GCATCGTTCCCACTGCGATGCTGGTTGCCAACGATCAGAT

```
                        -continued
GGCGCTGGGCGCAATGCGCGCCATTACCGAGTCCGGGCTG
CGCGTTGGTGCGGATATCTCGGTAGTGGGATACGACGATA
CCGAAGACAGCTCATGTTATATCCCGCCGTCAACCACCAT
CAAACAGGATTTTCGCCTGCTGGGGCAAACCAGCGTGGAC
CGCTTGCTGCAACTCTCTCAGGGCCAGGCGGTGAAGGGCA
ATCAGCTGTTGCCCGTCTCACTGGTGAAAAGAAAAACCAC
CCTGGCGCCCAATACGCAAACCGCCTCTCCCCGCGCGTTG
GCCGATTCATTAATGCAGCTGGCACGACAGGTTTCCCGAC
TGGAAAGCGGGCAGTGAGCGCAACGCAATTAATGTGAGTT
AGCTCACTCATTAGGCACCCCAGGCTTTACACTTTATGCT
TCCGGCTCGTATGTTGTGTGGAATTGTGAGCGGATAACAA
TTTCACACAGGAAACAGCTATGACCATGATTACGGATTCA
CTGGCCGTCGTTTTACAACGTCGTGACTGGGAAAACCCTG
GCGTTACCCAACTTAATCGCCTTGCAGCACATCCCCCTTT
CGCCAGCTGGCGTAATAGCGAAGAGGCCCGCACCGATCGC
CCTTCCCAACAGTTGCGCAGCCTGAATGGCGAATGGCGCT
TTGCCTGGTTTCCGGCACCAGAAGCGGTGCCGGAAAGCTG
GCTGGAGTGCGATCTTCCTGAGGCCGATACTGTCGTCGTC
CCCTCAAACTGGCAGATGCACGGTTACGATGCGCCCATCT
ACACCAACGTAACCTATCCCATTACGGTCAATCCGCCGTT
TGTTCCCACGGAGAATCCGACGGGTTGTTACTCGCTCACA
TTTAATGTTGATGAAAGCTGGCTACAGGAAGGCCAGACGC
GAATTATTTTTGATGGCGTTGGAATT
SEQ ID NO: 74
```

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A method for identifying a compound expected to be useful in inhibiting LRRK2 protein kinase activity, the method comprising the steps of:
   (1) determining whether the compound inhibits the protein kinase activity of a LRRK2 polypeptide on a substrate polypeptide wherein the LRRK2 polypeptide comprises a sequence having at least 85% identity to a wild type human LRRK2 (SEQ ID NO:69) or fragment thereof, and wherein the substrate polypeptide comprises the sequence (W/R)(X)(X)(F/Y/H/T)(Y/W/R)(T)(X)(R/T)(R)(X) (SEQ ID NO:71), where X represents any amino acid: and
   (2) selecting the compound that inhibits the protein kinase activity of the LRRK2 polypeptide.

2. The method of claim 1 wherein the LRRK2 polypeptide comprises at least residues 1326-2527 of wild type human LRRK2 (SEQ ID NO:69).

3. The method of claim 1 wherein the LRRK2 polypeptide comprises an amino acid sequence having a single mutation in the wild-type human LRRK2 protein (SEQ ID NO:69) selected from the group consisting of R1441C, R1441G, Y1699C, R1914H, I2012T, I2020T, T2356I, G2385R, K544E, P755L, R793M, Q930R, S973N, R1067Q, S1096C, I1122V, S1228T, I1371V, R1441H, A1442P, R1514Q, M1869T, and G2019S.

4. The method of claim 1 wherein the LRRK2 polypeptide is a GST fusion polypeptide and/or wherein the LRRK2 polypeptide is recombinant.

5. The method of claim 1 wherein the substrate polypeptide consists of or comprises the sequence WWKFYTLRRA (SEQ ID NO:67), WWRFYTLRKA (SEQ ID NO:48), RLGWWKFYTLRRARQGNTKQR (SEQ ID NO:49), RLGWRFYTLRKARQG NTKQR (SEQ ID NO:50) or RLGWRFYTLRRARQGNTKQR (SEQ ID NO:51) and/or wherein the substrate polypeptide is a GST fusion polypeptide.

6. A method for identifying a compound expected to be useful in treating Parkinson's Disease (PD) or Parkinsonism, the method comprising the steps of
 (1) determining whether the compound inhibits the phosphorylation of a substrate polypeptide by a LRRK2 polypeptide, and
 (2) selecting the compound which inhibits the phosphorylation of the substrate polypeptide by the LRRK2 polypeptide, wherein the substrate polypeptide is as defined in claim 1.

7. The method of claim 3, further comprising selecting a compound that inhibits the protein kinase activity of a LRRK2 polypeptide, wherein the LRRK2 polypeptide is a wild type LRRK2 polypeptide.

8. The method of claim 4, wherein the GST fusion polypeptide is GST-LRRK2[1326-2527, G2019S].

9. The method of claim 5, wherein the GST fusion polypeptide is GST-RLGWWRFYTLRRARQGNTKQR.

* * * * *